US007060850B2

(12) United States Patent
Zhang et al.

(10) Patent No.: US 7,060,850 B2
(45) Date of Patent: Jun. 13, 2006

(54) FLUOROUS TAGGING AND SCAVENGING REACTANTS AND METHODS OF SYNTHESIS AND USE THEREOF

(75) Inventors: Wei Zhang, Mars, PA (US); Zhiyong Luo, San Diego, CA (US); Tadamichi Nagashima, Allison Park, PA (US); Christine Hiu-Tung Chen, Pittsburgh, PA (US); Marvin S. Yu, Pittsburgh, PA (US)

(73) Assignee: Fluorous Technologies Incorporated, Pittsburgh, PA (US)

( * ) Notice: Subject to any disclaimer, the term of this patent is extended or adjusted under 35 U.S.C. 154(b) by 71 days.

(21) Appl. No.: 10/617,431

(22) Filed: Jul. 11, 2003

(65) Prior Publication Data

US 2004/0073054 A1  Apr. 15, 2004

Related U.S. Application Data

(60) Provisional application No. 60/442,840, filed on Jan. 27, 2003, provisional application No. 60/442,762, filed on Jan. 27, 2003, provisional application No. 60/442,712, filed on Jan. 27, 2003, provisional application No. 60/396,952, filed on Jul. 18, 2002, provisional application No. 60/395,067, filed on Jul. 11, 2002.

(51) Int. Cl.
  *C07F 7/08* (2006.01)
(52) U.S. Cl. .................. 556/465; 564/510; 568/683
(58) Field of Classification Search ............... 556/465; 564/510; 568/683
  See application file for complete search history.

(56) References Cited

U.S. PATENT DOCUMENTS

| 4,022,897 | A | 5/1977 | Yale et al. |
| 4,098,894 | A | 7/1978 | Buchel et al. |
| 4,745,191 | A | 5/1988 | Husbands |
| 5,236,923 | A | 8/1993 | Kirsten et al. |
| 5,463,082 | A | 10/1995 | Horvath et al. |
| 5,777,121 | A | 7/1998 | Curran et al. |
| 5,859,247 | A | 1/1999 | Curran et al. |
| 6,156,896 | A | 12/2000 | Curran et al. |
| 6,600,074 | B1 * | 7/2003 | Onishi et al. ............... 564/442 |
| 6,749,756 | B1 * | 6/2004 | Curran et al. ............... 210/668 |
| 2002/0183521 | A1 | 12/2002 | Curran et al. |
| 2003/0078444 | A1 | 4/2003 | Curran et al. |
| 2003/0125590 | A1 | 7/2003 | Curran et al. |

FOREIGN PATENT DOCUMENTS

| DE | 1925555 | 1/1971 |
| EP | 0 248 697 A1 | 12/1987 |
| EP | 0328111 A2 | 8/1989 |
| EP | 0 354 297 A1 | 2/1990 |
| EP | 0 468 531 A1 | 1/1992 |
| EP | 0628316 A1 | 12/1994 |
| GB | 1143481 | 2/1969 |
| GB | 1269096 | 3/1972 |
| JP | 58-057325 | 4/1983 |
| JP | 62205350 | 9/1987 |
| JP | 62278551 | 12/1987 |
| JP | 63-239254 | 10/1988 |
| JP | 07207021 | 8/1995 |
| WO | WO 97/01562 | 1/1997 |
| WO | WO 98/25916 | 6/1998 |
| WO | WO 00/18774 | 4/2000 |
| WO | WO 01/61332 A1 | 8/2001 |

OTHER PUBLICATIONS

Schwinn et al., 2002, Helvetica Chimica Acta, 85(1): 255-264.*
Schwinn et al., 2002, CAS: 137:32933.*
International Search Report from PCT/US03/21686, International Filing Date Nov. 7, 2003, Fluorous Technologies.
Kiss, et al., "An improved design of fluorophilic molecules: prediction of the In P fluorous partition coefficient, fluorophilicity, using 3D QSAR descriptors and neural networks"; Journal of Fluorine Chemistry, 108 (2001) 95-109.
Kleijn, et al., "Synthesis of Arylzinc Thiolates Containing Perfluoroalkyl Chains. Model Catalyst Precursors for the Enantioselective Zinc-Mediated 1,2-Addition of Dialkylzincs to Aldehydes in Fluorous Biphase Systems"; Organic Letters, (1999), vol. 1(6), 853-855.

(Continued)

*Primary Examiner*—Kamal A. Saeed
*Assistant Examiner*—Robert Shiao
(74) *Attorney, Agent, or Firm*—Kirkpatrick & Lockhart Nicholson Graham LLP

(57) ABSTRACT

The present invention includes methods and compositions for increasing the fluorous nature of an organic compound by reacting it with at least one fluorous compound to produce a fluorous tagged organic compound. The increased fluorous nature of the fluorous tagged organic compound can then be utilized to separate the fluorous organic compound from untagged reagents, reactants, catalysts and/or products derived therefrom. The resultant fluorous tagged organic compound can be subjected to subsequent chemical transformations, wherein the fluorous nature of the tagged compound is utilized to increase the ease of separation of the fluorous tagged organic compound from untagged reagents, reactants, catalysts and/or products derived therefrom, after each chemical transformation. The chemical transformations result in a second fluorous tagged organic compound wherein the fluorous nature of the second fluorous tagged organic compound can then be reduced by removing the fluorous group therefrom, thereby producing a second organic compound that may be employed as a pharmaceutical compound or intermediate, or a combinatorial library component.

23 Claims, No Drawings

OTHER PUBLICATIONS

Schwinn, et al., "Perfluoro-Tagged Benzyloxycarbonyl Protecting Group and Its Application in Fluorous Biphasic Systems"; Helvetica Chimica Acta, vol. 85 (2002), 255-264.

Filippov, et al., "Use of benzyloxycarbonyl (Z)-based fluorophillic tagging reagents in the purification of synthetic peptides"; Tetrahedron Letters, 43 (2002) 7809-7812.

Curran, et al., "Synthesis and Reactions of Fluorous Carbobenzyloxy ($^F$Cbz) Derivatives of α-Amino Acids"; Journal of Organic Chemistry, (2003), 68, 4643-4647.

Brown, et al., "Preparation of N-1, 1-dl-H-perfluoroalkyl Amines"; Journal of Organic Chemistry, (1957), 22, 454.

Allouch, et al., "Synthèses et réactivité avec des nucléophiles de sels de perfluoroalkylméthylèneoxy(trisdiméthylamino) phosphonium"; Journal of Fluorine Chemistry, 66 (1994) 31-38.

Billard, et al., "Reactivity of Stable Trifuoroacetaldehyde Hemiaminals. 2. Generation and Synthetic Potentialities of Fluorinated Iminiums"; J. Org. Chem., (2002), 67, 997-1000.

Lindsley, et al., "Fluorous-tethered quenching reagents for solution phase parallel synthesis"; Tetrahedron Letters, 43 (2002) 4225-4228.

Trabelsi, et al., "Synthèse de glycosides et de nucléosides F-alkylés"; Journal of Fluorine Chemistry, 56 (1992) 105-107.

Jouani, et al., "Synthèse des isocyanates de 2-F-alkyléthyle"; Journal of Fluorine Chemistry, 56 (1992) 85-92.

Lindsley, et al., "Fluorous-tethered amine bases for organic and parallel synthesis: scope and limitations", Tetrahedron Letters, 43 (2002) 6319-6323.

Zhang, et al., "Fluorous elecctrophilic scavengers for solution-phase parallel synthesis", Tetrahedron Letters, 44 (2003) 2065-2068.

U.S. Appl. No. 09/506,779, Curran et al.
U.S. Appl. No. 09/565,087, Curran et al.
U.S. Appl. No. 09/583,247, Wipf et al.
U.S. Appl. No. 09/602,105, Curran et al.
U.S. Appl. No. 09/932,903, Curran et al.

Curran, Strategy-Level Separations in Organic Synthesis: From Planning to Practice, Angew. Chem., Int. Ed. Eng., 1998, 37, 1175-1196.

Flynn, Phase-Trafficking Reagents and Phase-Switching Strategies for Parallel Synthesis, Med. Res. Rev., 1999, 19, 408-431, John Wiley & Sons, Inc.

Kaldor et al., Combinatorial chemistry using polymer-supported reagents, Curr. Opin. Chem. Bio., 1997, 1, 101-106.

Shuttleworth et al., Functionalised Polymers: Recent Developments and New Applications in Synthetic Organic Chemistry, Synthesis, 1997, 1217-1239.

Ley et al., Multi-step organic synthesis using solid-supported reagents and scavengers: a new paradigm in chemical library generation, J. Chem. Soc., Perkin Trans. 1, 2000, 3815-4195.

Eames et al., Polymeric Scavenger Reagents in Organic Synthesis, Eur. J. Org. Chem., 2001, 1213-1224.

Danielson et al., Fluoropolymers and fluorocarbon bonded phases as column packings for liquid chromatography, J. Chromat., 1991, 544, 187-199, Elsevier Science Publishers B.V.

Curran, Fluorous Reverse Phase Silica Gel. A New Tool for Preparative Separations in Synthetic Organic and Organofluorine Chemistry, Synlett, 2001, 9, 1488-1496.

Zhang, Fluorous Synthesis of Disubstituted Pyrimidines, Org. Lett., 2003, 5, 1011-1013.

Chen et al., FluoMar, a Fluorous Version of the Marshall Resin for Solution-Phase Library Synthesis, Org. Lett., 2003, 5, 1015-1017.

Zhang et al., Fluorous electrophilic scavengers for solution-phase parallel synthesis, Tet. Lett., 2003, 44, 2065-2068.

Orain et al., Protecting Groups in Solid-Phase Organic Synthesis, J. Combinatorial Chem., 2002, 4, 1-16.

Studer et al., Fluorous Synthesis: A Fluorous-Phase Strategy for Improving Separation Efficiency in Organic Synthesis, Science, 1997, 275, 823-826.

Studer et al., A Strategic Alternative to Solid Phase Synthesis: Preparation of a Small Isoxazoline Library by "Fluorous Synthesis", Tetrahedron, 1997, 53, 6681-6696.

Studer et al., Fluorous Synthesis: Fluorous Protocols for the Ugi and Biginelli Multicomponent Condensations, J. Org. Chem., 1997, 62,-2917-2924.

Curran et al., Preparation of a Fluorous Benzyl Protecting Group and Its Use in a Fluorous Synthesis Approach to a Disaccharide, Tet. Lett., 1998, 39, 4937-4940.

Curran et al., Fluorous Synthesis with Fewer Fluorines (Light Fluorous Synthesis): Separation of Tagged from Untagged Products by Solid-Phase Extraction with Fluorous Reverse-Phase Silica Gel, J. Am. Chem. Soc., 1999, 121, 9069-9072.

Zhang et al., Separation of "Light Fluorous" Reagents and Catalysts by Fluorous Solid-Phase Extraction: Synthesis and Study of a Family of Triarylphosphines Bearing Linear and Branched Fluorous Tags, J. Org. Chem., 2000, 65, 8866-8873.

Luo et al., Fluorous Boc ($^F$Boc) Carbamates: New Amine Protecting Groups for Use in Fluorous Synthesis, J. Org. Chem., 2001, 66, 4261-4266.

Luo et al., Fluorous Mixture Synthesis: A Fluorous-Tagging Strategy for the Synthesis and Sepration of Mixtures of Organic Compounds, Science, 2001, 291, 1766-1769.

Curran et al., Thiol additions to acrylates by fluorous mixture synthesis: relative control of elution order in demixing by the fluorous tag and the thiol substituent, Tetrahedron, 2001, 57, 5243-5253.

Chen et al., "Analogous" Organic Synthesis of Small-Compound Libraries: Validation of Combinatorial Chemistry in Small-Molecule Synthesis, J. Am. Chem. Soc. 1994, 116, 2661-2662.

Bauer et al., A Novel Linkage for the Solid-Phase Synthesis of Hydroxamic Acids, Tet. Lett., 1997, 38, 7233-7236.

Matthews et al., Parallel Synthesis of Alkyl Tetrazole Derivatives Using Solid Support Chemistry, J. Combinatorial Chem., 2000, 2, 19-23.

Findeis et al., Nitrobenzophenone Oxime Based Resins for the Solid-Phase Synthesis of Protected Peptide Segments, J. Org. Chem., 1989, 54, 3478-3482.

Booth et al., Solid-Supported Reagent Strategies for Rapid Purification of Combinatorial Synthesis Products, Acc. Chem. Res., 1999, 32, 18-26.

Hodges, Covalent Scavengers for Primary and Secondary Amines, Synlett, 1999, 1, 152-158.

Shuttleworth et al., Functionalised Polymers in Organic Chemistry; Part 2, Synthesis 2000, 8, 1035-1074.

Linclau et al., Organic-Fluorous Phase Switches: A Fluorous Amine Scavenger for Purification in Solution Phase Parallel Synthesis, J. Org. Chem, 1999, 64, 2835-2842.

Zhang et al., Use of fluorous silica gel to separate fluorous thiol quenching derivatives in solution-phase parallel synthesis, Tetrahedron, 2002, 58, 3871-3875.

Gooding et al., Enantioselective Synthesis of 2-Substituted Pyrrolidines From 4-Hydroxynitriles. Application to the Synthesis of the Dopamine Agonist RS-59022, Synth.. Commun., 1995, 25, 1155-1166.

Booth et al., Polymer-Supported Quenching Reagents for Parallel Purification, J. Am. Chem. Soc., 1997, 119, 4882-4886.

Blackburn et al., Parallel Synthesis of 3-Aminoimidazo[1,2-a]pyridines and pyrazines by a New Three-Component Condensation, Tet. Lett., 1998, 39, 3635-3638.

Creswell et al., Combinatorial Synthesis of Dihydropyridone Libraries and their Derivatives, Tetrahedron, 1998, 54, 3983-3998.

Tamura et al., Polymer-Supported Bases. XII. Regioselective Synthesis of Lysophospholipids Using Polymer-Supported Bicyclic Amidines or Guanidines, Synth.. Commun., 1994, 24, 2907-2914.

Xu et al., Polymer Supported Bases in Combinatorial Chemistry: Synthesis of Aryl Ethers from Phenols and Alkyl Halides and Aryl Halides, Tet. Lett., 1997, 38, 7737-7340.

Simoni et al., 1,5,7-Triazabicyclo[4.4.0]dec-1-ene(TBD), 7-methyl-TBD (MTBD) and the polymer-supported TBD (P-TBD): three efficient catalysts for the nitroaldol (Henry) reaction and for the addition of dialkyl phospites to unsaturated systems, Tet. Lett., 2000, 41, 1607-1610.

Weidner et al., Polymer-assisted solution phase synthesis: a general method for sequestration of byproducts formed from activated acyl-transfer reactants, Tet. Lett., 1999, 40, 239-242.

Keay et al., Polymer-Bound Dialkylaminopyridine Catalysts: Synthesis and Applications, Chem. Ind., 1994, 53, 339-350.

Guendouz et al., Polymer Bound 4-Dialkylamino Pyridines: Synthesis, Characterization And Catalytic Efficiency, Tetrahedron, 1988, 44, 7095-7108.

Tomoi et al., Polymer-Supported Bases, 1 Synthesis and Catalytic Activity of Polymer-Bound 4-(N-Benzyl-N-methylamino)pyridine, Makromol. Chem., Rapid Commun., 1982, 3, 537-542.

Shai et al., "Mediator Methodology" for the Synthesis of Peptides in a Two-Polymeric System, J. Am. Chem. Soc., 1985, 107, 4249-4252.

Flynn et al., Chemical Library Purification Strategies Based on Principles of Complementary Molecular Reactivity and Molecular Recognition, J. Am. Chem. Soc., 1997, 119, 4874-4881.

Chen et al., Protocols for amide high-speed analoging. Preparation of novel, small molecule cathepsin D inhibitors, Tet. Lett., 1999, 40, 9195-9199.

Kaldor et al., Use of Solid Supported Nucleophiles and Electrophiles for the Purification of Non-Peptide Small Molecule Libraries, Tet. Lett., 1996, 37, 7193-7196.

Parlow et al., In Situ Chemical Tagging: Tetrafluorophthalic Anhydride as a "Sequestration Enabling Reagent" (SER) in the Purification of Solution-Phase Combinatorial Libraries, Tet. Lett., 1997, 38, 7959-7962.

Barco et al., Polymer-bound 4-Benzylsulfonyl-1-triphenylphosphoranylidene-2-butanone as a Tool for the Solid-Phase Synthesis of Substituted Piperidin-4-one Derivatives, Tet. Lett., 1998, 39, 7591-7594.

Kobayashi et al., Efficient Synthesis of Diverse Monosaccharide Derivatives in the Solid Phase, J. Org. Chem., 1998, 63, 4868-4869.

Shapiro, Alkenes From Tosylhydrazones, Org. React., 1979, 23, 405-507.

Gravel et al., Universal Solid-Phase Approach for the Immobilization, Derivatization, and Resin-to-Resin Transfer Reactions of Boronic Acids, J. Org. Chem., 2002, 67, 3-15.

Gravel et al., Resin-to-Resin Suzuki Coupling of Solid Supported Arylboronic Acids, J. Comb. Chem., 2000, 2, 228-231.

Hall et al., $N,N$-Diethanolaminomethyl Polystyrene: An Efficient Solid Support to Immobilize Boronic Acids, Angew. Chem., Int. Ed. Eng., 1999, 38, 3064-3067.

Dressman et al., Solid Phase Synthesis of Urea Libraries Using a Diversifiable Thiophenoxy Carbonyl Linker, Tet. Lett., 1998, 39, 3631-3634.

Coppola, A New Scavenger Resin for Amines, Tet. Lett., 1998, 39, 8233-8236.

Yu et al., Acetoacetoxy ethyl methacrylate (AAEM) resin, a new scavenger for primary amines in the presence of secondary amines, Tet. Lett., 2000, 41, 8963-8967.

Hu et al., Asymmetric Borane Reduction of Prochiral Ketones by Polymer-Supported Chiral Sulfonamides, J. Org. Chem., 2001, 66, 303-304.

Pirrung et al., Oxazoline Synthesis from Hydroxyamides by Resin Capture and Ring-Forming Release, J. Comb. Chem., 2000, 2, 675-680.

Nizi et al., Solid Phase Synthesis of 2,6-Disubstituted-4($3H$)-pyrimidinones Targeting HIV-1 Reverse Transcriptase, Tet. Lett., 1998, 39, 3307-3310.

Curran, "Fluorous Techniques for the Synthesis of Organic Molecules: A Unified Strategy for Reaction and Separation," in *Stimulating Concepts in Chemistry*, Shibasaki, Fraser-Stoddart and Vogtle, eds., Wiley-VCH, Weinheim, 2000, 25-37.

Curran et al., "Experimental techniques in fluorous synthesis: a user's guide," in *Combinatorial Chemistry: A Practical Approach*, Oxford University Press, Oxford, 2001, 327-352.

Seneci, "Solid-Phase Synthesis: Small Organic Molecules" in Solid-Phase Synthesis and Combinatorial Techniques, J. Wiley & Sons, New York, NY 2000, 91-135.

Greene et al., Protective Groups in Organic Synthesis, 3rd ed., Wiley Interscience, New York, NY, 1999, 36-39, 74-99, 102-107, 180-181, 266-271,506-509, 526-537, 484-485,642-645.

Kocienski, Protecting Groups, Thieme, Stuttgart, 1994, 46-69, 78-79, 136-139, 194-199, 202-205, 220-231.

Robertson, Protecting Group Chemistry, Oxford University Press, Oxford, 2000, 18-95.

Gladysz, Are Teflon "Ponytails" the Coming Fashion for Catalysts?, Science, 1994, 266, 55-56.

Horvath et al., Facile Catalyst Separation Without Water: Fluorous Biphase Hydroformylation of Olefins, Science, 1994, 266, 72-75.

Zhu, A Novel Reaction Medium: Perfluorocarbon Fluids, Synthesis, 1993, 953-954.

Berendsen et al., (Heptadecafluorodecyl)dimethylsilyl Bonded Phase for Reversed-Phase Liquid Chromatography, Anal. Chem., 1980, 52, 1990-1993.

Billiet et al., Retention And Selectivity Characteristics Of A Non-Polar Perfluorinated Stationary Phase For Liquid Chromatography, J. of Chromatography, 1981, 218, 443-454.

Hudlicky, "Properties of Organic Compounds of Fluorine", Chemistry of Organic Fluorine Compounds, PTR Prentice Hall, New York, 1992, 542-545.

Boutevin et al., Study of the alkylation of chlorosilanes. Part I. Synthesis of tetra(1$H$,1$H$,2$H$,2$H$-polyfluoroalkyl)silanes, J. of Fluorine Chemistry, 1993, 60, 211-223.

Kolycheva et al., Fluorinated benzaldehydes in Leuckart and Rodinov reactions, Zhumal Organicheskoi Khimii, 1989, 25, 2367-72, Abstract from CAPLUS Database.

Nakamura et al., Enantioselective addition of diethylzinc to aldehydes catalyzed by fluorous β-aminoalcohols, Tetrahedron, 2001, 57, 5565-5571.

Gaunt et al., Rational Design of Benzyl-Type Protecting Groups Allows Sequential Deprotection of Hydroxyl Groups by Catalytic Hydrogenolysis, J. Org. Chem., 1998, 63, 4172-4173.

Dünnebacke et al., Stabile 4,4',4"-trisubstituierte Triphenylmethyl-Radikale, Chem. Ber. 1989, 122, 533-535.

Neumann et al., Sterically Hindered Free Radicals. 14. Substituent-Dependent Stabilization of Para-Substituted Triphenylmethyl Radicals, J. Am. Chem. Soc., 1986, 108, 3762-3770.

\* cited by examiner

FLUOROUS TAGGING AND SCAVENGING REACTANTS AND METHODS OF SYNTHESIS AND USE THEREOF

CROSS-REFERENCE TO RELATED APPLICATIONS

This application claims priority to U.S. Provisional Patent Application Ser. No. 60/395,067, entitled "New Fluorous Tagging (Scavenging) Reactants and Methods of Synthesis and Use Thereof", filed Jul. 11, 2002; U.S. Provisional Patent Application Ser. No. 60/396,952, entitled "New Fluorous Tagging Reagents and Methods of Synthesis and Use Thereof", filed Jul. 18, 2002; U.S. Provisional Patent Application Ser. No. 60/442,712, entitled "Fluorous Synthesis of Disubstituted Pyrimidines", filed Jan. 27, 2003; U.S. Provisional Patent Application Ser. No. 60/442,762, entitled "FluoMar™, A Fluorous Version of the Marshall Resin for Solution-phase Library Synthesis", filed Jan. 27, 2003; and U.S. Provisional Patent Application Ser. No. 60/442,840, entitled "Fluorous Electrophilic Scavengers for Solution Phase Parallel Synthesis", filed Jan. 27, 2003, which are incorporated by reference herein in their entirety.

GOVERNMENTAL INTEREST

This invention was made with Government support under grants 1 R44 GM67326-01 and 1 R43 GM066415-01 awarded by the National Institutes of Health. The Government may have certain rights in the invention.

FIELD OF THE INVENTION

The present invention relates to fluorous tagging compounds and fluorous scavenging compounds and to methods of increasing the fluorous nature of organic compounds by reacting them with a fluorous tagging or scavenging compound.

BACKGROUND OF THE INVENTION

It is generally the case that organic compounds must be synthesized as pure substances through well-planned reactions and scrupulous separation/purification. In fields such as drug discovery, catalyst design and new material development, tens of thousands of organic compounds must be synthesized and tested to discover a few active ones. In the pharmaceutical industry, for example, synthesizing large numbers of compounds in the traditional way is ineffective relative to the rapid emergence of new biological targets. A major factor limiting the productivity of orthodox solution (liquid) phase organic synthesis is the time consuming process of purification. High throughput organic synthesis, therefore, preferably integrates organic reactions with rapid purification/separation procedures.

The attachment of "tags" to organic reaction components has become commonplace in combinatorial and parallel high throughput syntheses to facilitate the separation process. See, for example, Curran, D. P. "Strategy-level Separations in Organic Synthesis; From Planning to Practice," *Angew. Chem., Int. Ed. Eng.* 1998, 37, 1175–1196; Flynn, D. "Phase-trafficking Reagents and Phase-switching Strategies for Parallel Synthesis," *Med. Res. Rev.* 1999, 19, 408–432. The process of tagging excess reagents, reactants, catalysts or byproducts for their separation from the desired products is often called "scavenging" or "quenching". In a common embodiment of tagging, a substrate, for example a small organic molecule, is tagged with a separation tag typically comprised of a polymeric bead in a technique known as "solid phase synthesis". See, for example, Seneci, P. "*Solid-phase Synthesis and Combinatorial Technologies*," John Wiley and Sons New York, 2000. Conducting one or more reactions on the tagged substrate (or subsequent intermediates) with untagged reagents, reactants, catalysts, etc. then provides a tagged product. The presence of the separation tag allows easy separation of the tagged intermediates and/or product from untagged reagents, reactants, catalysts and/or products derived therefrom. For example, simple filtration is usually used to separate the polymer bead tagged intermediate or product from solvent, byproduct and/or any unreacted reagent.

Because reactions with polymer-bound substrates and intermediates are typically heterogeneous, large excesses of reagents are often needed to drive reactions to completion. This adds to the expense of a reaction and can also lead to unwanted tagged byproducts. Even when using excesses of reagents, solid phase synthesis methods often do not match their solution phase counterparts in terms of speed, yield, scope and cleanliness of products. Furthermore, other than by filtration, it is not usually possible to further purify polymer-bound intermediates and products. In other words, polymer bound intermediates or products cannot be separated from bound byproducts without removal from the polymer and subsequent purification. Accordingly reactions on the solid phase that occur with broad scope in quantitative yield (so that no polymer-bound byproducts are formed) are the target of much research.

In a common embodiment of scavenging, a solution phase reaction is conducted under standard conditions, and then a scavenger or quencher is added and allowed to react with one or more reaction components that have been targeted for separation from the desired products. The most commonly used scavengers are solid-phase materials such as polymers or bonded phases of silica. See, for example, Kaldor, S. W., Siegel, M. G. "*Combinatorial Chemistry Using Polymer Supported Reagents,*" *Curr. Opin. Chem. Bio.* 1997, 1, 101–106; Shuttleworth, S. J., Allin, S. M., Sharma, P. K. "*Functionalised Polymers: Recent Developments and New Applications in Synthetic Organic Chemistry,*" *Synthesis* 1997, 1217–1239; Ley, S. V., et al. "*Multi-step Organic Synthesis Using Solid-supported Reagents and Scavengers: A New Paradigm in Chemical Library Generation,*" *J. Chem. Soc., Perkin Trans.* 1 2000, 3815–4195; Eames, J., Watkinson, M. "*Polymeric Scavenger Reagents in Organic Synthesis,*" *Eur. J. Org. Chem.* 2001, 1213–1224.

Like reactions with polymer-bound substrates, reactions with solid phase scavengers are almost always heterogeneous. Large excesses of solid phase scavengers are often used to facilitate the scavenging reaction, yet the speed and cleanliness of solution phase reactions still often cannot be duplicated. Solution phase scavengers with appropriate acid or basic functionality can be used, but this approach requires that the desired products be acid or base stable (or both) and limits the functionality that can be present.

Recently, fluorous synthetic and separation techniques have attracted the interests of organic chemists. In fluorous synthetic techniques, reaction components are typically attached to fluorous groups such as perfluoroalkyl groups to facilitate the separation of products. Reactions are carried out in the solution phase, so solubility and reaction problems inherent with solid phase synthetic techniques do not arise. In general, fluorous tagged or scavenged molecules partition preferentially into a fluorous phase while non-tagged/non-scavenged molecules partition into an organic phase.

Although fluorous synthetic and/or separation techniques are promising, such techniques are currently limited by a lack of available and suitable fluorous tags and scavengers.

Accordingly, further improvements would be a welcome addition to the art, wherein fluorous tagging and scavenging compounds, and methods for their synthesis and use in increasing the fluorous nature of organic compounds are developed.

SUMMARY OF THE INVENTION

The present invention includes methods and compositions for increasing the fluorous nature of an organic compound by reacting it with at least one fluorous compound to produce a fluorous tagged organic compound. The increased fluorous nature of the fluorous tagged organic compound can then be utilized to separate the fluorous organic compound from untagged reagents, reactants, catalysts and/or products derived therefrom. The resultant fluorous tagged organic compound can be subjected to subsequent chemical transformations, wherein the fluorous nature of the tagged compound is utilized to increase the ease of separation of the fluorous tagged organic compound from untagged reagents, reactants, catalysts and/or products derived therefrom, after each chemical transformation. The chemical transformations result in a second fluorous tagged organic compound wherein the fluorous nature of the second fluorous tagged organic compound can then be reduced by removing the fluorous group therefrom, thereby producing a second organic compound that may be employed as a pharmaceutical compound or intermediate, or a combinatorial library component.

In one embodiment, the present invention provides a method for increasing the fluorous nature of an organic compound by reacting the organic compound with at least one second compound having the formula:

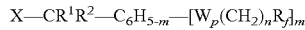
$$X\text{---}CR^1R^2\text{---}C_6H_{5-m}\text{---}[W_p(CH_2)_nR_f]_m \quad \text{(I)}$$

$R_f$ is a fluorous group. The group X on fluorous compound (I) is either a leaving group, a nucleophilic group or an electrophilic group. The substitutents $R^1$ and $R^2$ are independently, the same or different, either hydrogen, a linear alkyl group, a branched alkyl group, a phenyl group, a substituted phenyl group having the structure $C_6H_{5-q}(W')_q$, or fluorous substituted phenyl groups having the structure of either $C_6H_{5-m'}[W_{p'}(CH_2)_{n'}R_f]_{m'}$ or $C_6H_{5-m''}[W_{p''}(CH_2)_{n''}R_f]_{m''}$. The integer values for m, m' and m" are from 1 to 5; the integer values for n, n', and n" are from 0 to 5; p, p', and p" have values of either 0 or 1; and q has an integer value from 0 to 5. W is an atom or a grouping of atoms having the structure O, S, $NR^3$, $CR^4R^5$, or $SiR^6R^7$, wherein when W is $SiR^6R^7$ and $R^1$ and $R^2$ are each hydrogen, X is not one of Br, N-imidazolyl or —OH. W' is a grouping of atoms having the structure $OR^8$, $SR^9$, $NR^{10}R^{11}$, $CR^{12}R^{13}R^{14}$, or $SiR^{15}R^{16}R^{17}$. The substituents $R^3$, $R^4$, $R^5$, $R^8$, $R^9$, $R^{10}$, $R^{11}$, $R^{12}$, $R^{13}$, and $R^{14}$ are independently, the same or different, either hydrogen, linear alkyl, branched alkyl, aryl, benzyl or —$(CH_2)_{n'''}R_f$, and the substituents $R^6$, $R^7$, $R^{15}$, $R^{16}$, and $R^{17}$ are independently, the same or different, either linear alkyl, branched alkyl, aryl, benzyl or —$(CH_2)_{n'''}R_f$, wherein n''' in an integer from 0 to 5.

The organic compound has at least one functional group that reacts with group X on at least one second fluorous compound (I) to form at least one chemical bond between the organic compound and at least one second compound. The chemical reaction results in a first fluorous tagged organic compound with an increased fluorous nature relative to the fluorous nature of the organic compound. The increased fluorous nature of the first fluorous tagged organic compound enables separating the first fluorous tagged organic compound from other compounds by use of a fluorous separation technique.

In a second embodiment, the present invention provides a method for increasing the fluorous nature of an organic compound by reacting the organic compound with at least one second compound having the formula:

$$XCO_2CH_2R_d \quad \text{(II)}$$

wherein X is a leaving group and $R_d$ has one of the following substructures:

a) 
—CH=CH—$(CH_2)_nR_f$, b) 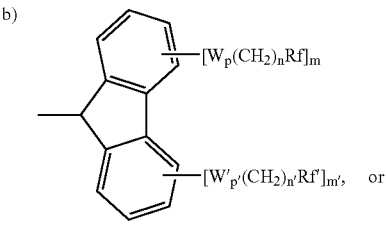

c) 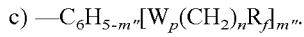
—$C_6H_{5-m''}[W_p(CH_2)_nR_f]_{m''}$.

$R_f$ and $R_{f'}$ are each fluorous groups. The integer value for m is from 1 to 4, m' is an integer from 0 to 4, and m" is an integer from 1 to 5. The integer values for n and n' are each from 0 to 5 and p and p' each has a value of either 0 or 1. W and W' are atoms or groupings of atoms each having the possible structure of O, S, $NR^{25}$, $CR^{26}R^{27}$, or $SiR^{28}R^{29}$. The substituents $R^{25}$, $R^{26}$ and $R^{27}$ are independently, the same or different, either hydrogen, linear alkyl, branched alkyl, aryl, benzyl or —$(CH_2)_nR_f$, and the substituents $R^{28}$ and $R^{29}$ are independently, the same or different, either linear alkyl, branched alkyl, aryl, benzyl or —$(CH_2)_nR_f$.

The organic compound has at least one functional group that reacts with leaving group X on at least one second fluorous compound (II) to form at least one chemical bond between the organic compound and at least one second compound. The chemical reaction results in a first fluorous tagged organic compound with an increased fluorous nature relative to the fluorous nature of the organic compound. The increased fluorous nature of the first fluorous tagged organic compound enables separating the first fluorous tagged organic compound from other compounds by use of a fluorous separation technique.

In another embodiment, the present invention provides a method for increasing the fluorous nature of an organic compound by reacting the organic compound with at least one second compound having the formula:

$$R^{31}R^{32}N(CH_2)_nR_f \quad \text{(III)}$$

wherein $R_f$ is a fluorous group and n is an integer with a value from 0 to 5. $R^{31}R^{32}$, when taken together, can comprise any of the groups:

a) $-(CH_2)_mW(CH_2)_{m'}-$, b) 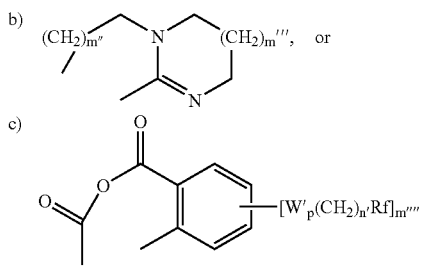

c) 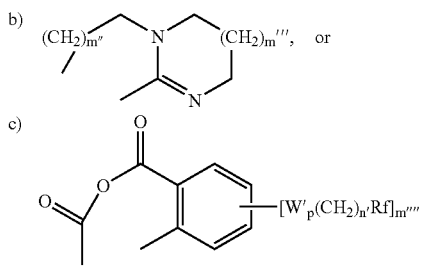

forming a cyclic amine. Alternatively, $R^{31}$ and $R^{32}$ can independently comprise any of the following groups: alkyl and pyridyl, hydrogen and $-(CH_2)_{n''}NH_2$, hydrogen and $-(CH_2)_{n''}N[(CH_2)_{n''}NH_2]_2$, or $-(CH_2)_{n'''}OH$, and $-(CH_2)_{n'''}OH$ forming an acyclic amine. The integer values for m and m' are each from 2 to 4, m'' and m''' each have integer values from 0 to 3, and m'''' is an integer from 0 to 4. The integer value for n' is from 0 to 5 and n'', n''' and n'''' each have integer values from 1 to 5. The value of p is either 0 or 1. W is an atom or grouping of atoms having the structure of $CH_2$, O, S, NH, or $NR^{33}$, wherein $R^{33}$ is either a linear alkyl, a branched alkyl or a benzyl group, and W' is an atom or grouping of atoms having the structure O, S, $NR^{34}$, $CR^{35}R^{36}$, or $SiR^{37}R^{38}$, wherein $R^{34}$, $R^{35}$, and $R^{36}$ are independently, the same or different, either hydrogen, linear alkyl, branched alkyl, aryl, benzyl or $-(CH_2)_nR_f$, and $R^{37}$ and $R^{38}$ are independently, the same or different, either linear alkyl, branched alkyl, aryl, benzyl or $-(CH_2)_nR_f$.

The organic compound has at least one functional group that reacts with at least one N or —OH group on at least one second compound (III) to form at least one chemical bond between the organic compound and at least one second compound, where the chemical bond may be either ionic or covalent. The chemical reaction results in a first fluorous tagged organic compound with an increased fluorous nature relative to the fluorous nature of the organic compound. The increased fluorous nature of the first fluorous tagged organic compound enables separating the first fluorous tagged organic compound from other compounds by use of a fluorous separation technique.

In still another embodiment, the present invention provides a method for increasing the fluorous nature of an organic compound by reacting the organic compound with at least one second compound having the formula:

$$X-C_6H_{5-m}-[W_p(CH_2)_nR_f]_m \quad (IV)$$

wherein $R_f$ is a fluorous group, m has an integer value from 1 to 5, n has an integer value from 0 to 5, p is either 0 or 1 and W is an atom or grouping of atoms having the structure of O, S, $NR^{39}$, $CR^{40}R^{41}$, or $SiR^{42}R^{43}$. When W is O, then X can have the structure $-SO_2NHNH_2$, $-CHO$ when p is 1, $-SH$, $-(CH_2)_nSH$, $-C(=NR^B)C_6H_4Y$, $-C(=O)CH_2C(=O)R^{44}$, $-COCl$, $-SO_2Cl$, $-OH$, $-NCZ$, or $-SO_3H$. When W is S, $NR^{39}$, $CR^{40}R^{41}$, or $SiR^{42}R^{43}$, then X can have the structure $-SO_2NH_2$, $-SO_2NHNH_2$, $-CHO$ when p is 1, $-SH$, $-(CH_2)_nSH$, $-C(=NR^B)C_6H_4Y$, $-C(=O)CH_2C(=O)R^{44}$, $-COCl$, $-SO_2Cl$, $-OH$, $-NCZ$, or $-SO_3H$. Z is either oxygen or sulfur. Y is either an electron withdrawing group, a hydrogen or an alkyl group and $R^B$ is either hydrogen, an alkyl group, an aryl group or a hydroxyl group. The integer value of n' is from 2 to 5. $R^{39}$, $R^{40}$ and $R^{41}$ are independently, the same or different, either hydrogen, linear alkyl, branched alkyl, aryl, benzyl or $-(CH_2)_nR_f$, and $R^{42}$ and $R^{43}$ are independently, the same or different, either linear alkyl, branched alkyl, aryl, benzyl or $-(CH_2)_nR_f$. $R^{44}$ is either linear alkyl, branched alkyl or benzyl.

The organic compound has at least one functional group that reacts with group X on at least one second compound (IV) to form at least one chemical bond between the organic compound and at least one second compound. The chemical reaction results in a first fluorous tagged organic compound with an increased fluorous nature relative to the fluorous nature of the organic compound. The increased fluorous nature of the first fluorous tagged organic compound enables separating the first fluorous tagged organic compound from other compounds by use of a fluorous separation technique.

In a further embodiment, the present invention provides a method for increasing the fluorous nature of an organic compound by reacting the organic compound with at least one second compound having the formula:

$$X-(CH_2)_nR_f \quad (V)$$

wherein $R_f$ is a fluorous group and n is an integer from 0 to 5. X is a grouping of atoms having the substructure of either $-C(CH_3)_2COCl$, $-CR^{45}R^{46}SH$, $-CR^{45}R^{46}SR^{47}$, $-SO_2Cl$, $-OC(=O)NHNH_2$, $-NHC(=NH)NH_2$, $-SO_2NH_2$, $-SO_2NHNH_2$, $-NCZ$, -maleimide, -α-succinic anhydride, or $-COCH_2COR^{48}$. $R^{45}$, $R^{46}$, $R^{47}$, and $R^{48}$ are independently, the same or different, either hydrogen, linear alkyl, branched alkyl, benzyl, or $-(CH_2)_nR_f$ and Z is either oxygen or sulfur.

The organic compound has at least one functional group that reacts with group X on at least one second compound (V) to form at least one chemical bond between the organic compound and at least one second compound. The chemical reaction results in a first fluorous tagged organic compound with an increased fluorous nature relative to the fluorous nature of the organic compound. The increased fluorous nature of the first fluorous tagged organic compound enables separating the first fluorous tagged organic compound from other compounds by use of a fluorous separation technique.

In still a further embodiment, the present invention provides a compound having the formula:

$$X-CR^1R^2-C_6H_{5-m}-[W_p(CH_2)_nR_f]_m \quad (I)$$

$R_f$ is a fluorous group. The group X is either a leaving group, a nucleophilic group or an Electrophilic group. The substitutents $R^1$ and $R^2$ are independently, the same or different, either hydrogen, a linear alkyl group, a branched alkyl group, a phenyl group, a substituted phenyl group having the structure $C_6H_{5-q}(W')_q$, or fluorous substituted phenyl groups having the structure of either $C_6H_{5-m'}[W_{p'}(CH_2)_{n'}R_f]_{m'}$ or $C_6H_{5-m''}[W_{p''}(CH_2)_{n''}R_f]_{m''}$. The integer values for m, m' and m'' are from 1 to 5; the integer values for n, n', and n'' are from 0 to 5; p, p', and p'' have values of either 0 or 1; and q has an integer value from 0 to 5. W is an atom or a grouping of atoms having the structure O, S, $NR^3$, $CR^4R^5$, or $SiR^6R^7$, wherein when W is $SiR^6R^7$ and $R^1$ and $R^2$ are each hydrogen, X is not one of Br, N-imidazolyl or —OH. W' is a grouping of atoms having the structure $OR^8$, $SR^9$, $NR^{10}R^{11}$, $CR^{12}R^{13}R^{14}$, or $SiR^{15}R^{16}R^{17}$. The substituents $R^3$, $R^4$, $R^5$, $R^8$, $R^9$, $R^{10}$, $R^{11}$, $R^{12}$, $R^{13}$, and $R^{14}$ are independently, the same or different, either hydrogen, linear alkyl, branched alkyl, aryl, benzyl or $-(CH_2)_{n'''}R_f$, and the substituents $R^6$, $R^7$, $R^{15}$, $R^{16}$, and $R^{17}$ are independently, the same or different, either linear alkyl, branched alkyl, aryl, benzyl or $-(CH_2)_{n'''}R_f$, wherein n''' in an integer from 0 to 5.

In yet a further embodiment, the present invention provides a compound having the formula:

$$XCO_2CH_2R_d \qquad (II)$$

wherein X is a leaving group and $R_d$ has one of the following substructures:

a) $-CH=CH-(CH_2)_nR_f$, b) 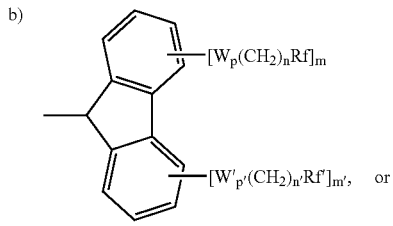

c) $-C_6H_{5-m''}[W_p(CH_2)_nR_f]_{m''}$.

$R_f$ and $R_{f'}$ are each fluorous groups. The integer value for m is from 1 to 4, m' is an integer from 0 to 4, and m'' is an integer from 1 to 5. The integer values for n and n' are each from 0 to 5 and p and p' each has a value of either 0 or 1. W and W' are atoms or groupings of atoms each having the possible structure of O, S, $NR^{25}$, $CR^{26}R^{27}$, or $SiR^{28}R^{29}$. The substituents $R^{25}$, $R^{26}$ and $R^{27}$ are independently, the same or different, either hydrogen, linear alkyl, branched alkyl, aryl, benzyl or $-(CH_2)_nR_f$, and the substituents $R^{28}$ and $R^{29}$ are independently, the same or different, either linear alkyl, branched alkyl, aryl, benzyl or $-(CH_2)_nR_f$.

In yet another embodiment, the present invention provides a compound having the formula:

$$R^{31}R^{32}N(CH_2)_nR_f \qquad (III)$$

wherein $R_f$ is a fluorous group and n is an integer with a value from 0 to 5. $R^{31}R^{32}$, when taken together, comprise any of the groups:

a) $-(CH_2)_mW(CH_2)_{m'}-$, b) 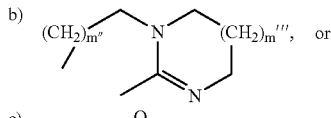

c) 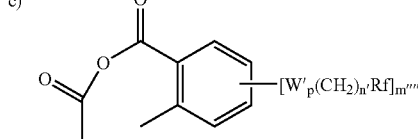

forming a cyclic amine. Alternatively, $R^{31}$ and $R^{32}$, independently, can comprise any of the following groups: alkyl and pyridyl, hydrogen and $-(CH_2)_{n''}NH_2$, hydrogen and $-(CH_2)_{n''}N[(CH_2)_{n''}NH_2]_2$, or $-(CH_2)_{n'''}OH$, and $-(CH_2)_{n''''}OH$ forming an acyclic amine. The integer values for m and m' are each from 2 to 4, m'' and m''' each have integer values from 0 to 3, and m'''' is an integer from 0 to 4. The integer value for n' is from 0 to 5 and n'', n''' and n'''' each have integer values from 1 to 5. The value of p is either 0 or 1. W is an atom or grouping of atoms having the structure of $CH_2$, O, S, NH, or $NR^{33}$, wherein $R^{33}$ is either a linear alkyl, branched alkyl or a benzyl group, and W' is an atom or grouping of atoms having the structure O, S, $NR^{34}$, $CR^{35}R^{36}$, or $SiR^{37}R^{38}$, wherein $R^{34}$, $R^{35}$, and $R^{36}$ are independently, the same or different, either hydrogen, linear alkyl, branched alkyl, aryl, benzyl or $-(CH_2)_nR_f$, and $R^{37}$ and $R^{38}$ are independently, the same or different, either linear alkyl, branched alkyl, aryl, benzyl or $-(CH_2)_nR_f$.

In another embodiment, the present invention provides a compound having the formula:

$$X-C_6H_{5-m}-[W_p(CH_2)_nR_f]_m \qquad (IV)$$

wherein $R_f$ is a fluorous group, m has an integer value from 1 to 5, n has an integer value from 0 to 5, p is either 0 or 1 and W is an atom or grouping of atoms having the structure of O, S, $NR^{39}$, $CR^{40}R^{41}$, or $SiR^{42}R^{43}$. When W is O, then X has the structure $-SO_2NHNH_2$, $-CHO$ when p is 1, $-SH$, $-(CH_2)_nSH$, $-C(=NR^B)C_6H_4Y$, or $-C(=O)CH_2C(=O)R^{44}$. When W is S, $NR^{39}$, $CR^{40}R^{41}$, or $SiR^{42}R^{43}$, then X has the structure $-SO_2NH_2$, $-SO_2NHNH_2$, $-CHO$ when p is 1, $-SH$, $-(CH_2)_nSH$, $-C(=NR^B)C_6H_4Y$, or $-C(=O)CH_2C(=O)R^{44}$. Z is either oxygen or sulfur. Y is either an electron withdrawing group, a hydrogen or an alkyl group and $R^B$ is a hydrogen, an alkyl group, an aryl group or a hydroxyl group. The integer value of n' is from 2 to 5. $R^{39}$, $R^{40}$ and $R^{41}$ are independently, the same or different, either hydrogen, linear alkyl, branched alkyl, aryl, benzyl or $-(CH_2)_nR_f$, and $R^{42}$ and $R^{43}$ are independently, the same or different, either linear alkyl, branched alkyl, aryl, benzyl or $-(CH_2)_nR_f$. $R^{44}$ is linear alkyl, branched alkyl or benzyl.

In a further embodiment, the present invention provides a compound having the formula:

$$X-(CH_2)_nR_f \qquad (V)$$

wherein $R_f$ is a fluorous group and n is an integer from 0 to 5. X is a grouping of atoms having the substructure of $-C(CH_3)_2COCl$.

In yet another embodiment, the present invention provides for a compound having a formula:

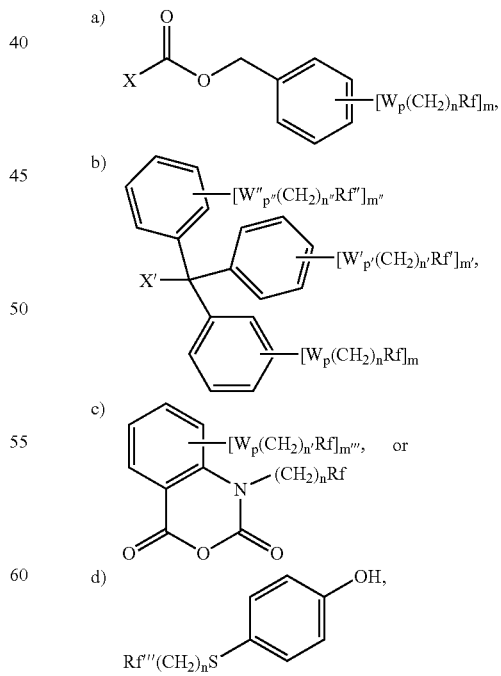

wherein $R_f$, $R_f'$, and $R_f''$ are each fluorous groups, $R_f'''$ is a perfluoroalkyl group of 8 to 16 carbon atoms, X and X' are leaving groups, m is an integer from 1 to 5, m', m", n, n', and n" are each integers from 0 to 5, m'" is an integer from 0 to 4, and p, p', and p" are each either 0 or 1. W, W' and W" are each an atom or grouping atoms having the formula O, S, $NR^{49}$, $CR^{50}R^{51}$, or $SiR^{52}R^{53}$. $R^{49}$, $R^{50}$, and $R^{51}$ are independently, the same or different, either hydrogen, linear alkyl, branched alkyl, aryl, benzyl or —$(CH_2)_{n'''}R_f$. $R^{52}$ and $R^{53}$ are independently, the same or different, either hydrogen, linear alkyl, branched alkyl, aryl, benzyl or —$(CH_2)_{n'''}R_f$ and n'" is an integer from 0 to 5.

DETAILED DESCRIPTION OF THE INVENTION

Other than in the operating examples, or where otherwise indicated, all numbers expressing quantities of ingredients, reaction conditions and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons or perfluorocarbons, fluorohydrocarbons, fluorinated ethers, fluorinated amines and fluorinated adamantyl groups). For example, perfluorinated ether groups can have the general formula —$[(CF_2)_xO(CF_2)_y]_zCF_3$, wherein x, y and z are integers. Perfluorinated amine groups can, for example, have the general formula —$[(CF_2)_x(NR^a)CF_2)_y]_zCF_3$, wherein $R^a$ can, for example, be $(CF_2)_nCF_3$, wherein n is an integer. Fluorous ether groups and fluorous amine groups suitable for use in the present invention need not be perfluorinated, however. The term "fluorous compound," thus refers, generally, to a compound comprising a portion rich in carbon-fluorine bonds. As used herein, the term "perfluorocarbons" refers, generally, to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. A few examples of suitable fluorous groups, $R_f$, for use in the present invention include, but are not limited to, —$C_4F_9$, —$C_6F_{13}$, —$C_8F_{17}$, —$C_{10}F_{21}$, —$C(CF_3)_2C_3F_7$, —$C_4F_8CF(CF_3)_2$, —$CF_2CF_2OCF_2CF_2OCF_3$, —$CF_2CF_2(NCF_2CF_3)CF_2CF_2CF_3$, fluorous adamantly groups, and/or mixtures thereof.

Perfluoroalkyl groups and hydrofluoroalkyl groups are well suited for use in the present invention. For example, $R_f$ can be a linear perfluoroalkyl group of 3 to 20 carbons, a branched perfluoroalkyl group of 3 to 20 carbons, and a hydrofluoroalkyl group of 3 to 20 carbons. Hydrofluoroalkyl groups may typically include up to one hydrogen atom for each two fluorine atoms. In the case of perfluoroalkyl groups and hydrofluoroalkyl groups, $R_f$ may be a linear perfluoroalkyl group of 6 to 12 carbons, a branched perfluoroalkyl group of 6 to 12 carbons, and a hydrofluoroalkyl group of 6 to 12 carbons.

The molecular weight of the fluorous tag of the present invention typically does not exceed about 2,500 g/mole, may be such as to not exceed 2,000 g/mole, and may be such as to not exceed 1,500 g/mole. In addition, compounds subject to the present invention may bear more than one fluorous tag, each of which have the molecular weight as provided herein.

As used herein, the terms "tagging" and "scavenging" refer, generally, to attaching a fluorous moiety or group (referred to as a "fluorous tagging moiety", "tagging group" or "fluorous tag") to a compound to create a "fluorous tagged compound". Separation of the tagged compounds of the present invention is achieved by using fluorous separation techniques that are based upon differences between/among the fluorous nature of a mixture of compounds. As used herein, the term "fluorous separation technique" refers generally to a method that is used to separate mixtures containing fluorous molecules or organic molecules bearing fluorous domains or tags from each other and/or from non-fluorous compounds based predominantly on differences in the fluorous nature of molecules (for example, size and/or structure of a fluorous molecule or domain or the absence thereof). Fluorous separation techniques include, but are not limited to, fluorous liquid-liquid extraction, fluorous solid phase extraction, and fluorous chromatography. See, for example, Danielson, N. D. et al., "*Fluoropolymers and Fluorocarbon Bonded Phases as Column Packings for Liquid Chromatography,*" J. Chromat., 1991, 544, 187–199; Curran, D. P. "*Fluorous Reverse Phase Silica Gel. A New Tool for Preparative Separations in Synthetic Organic and Organofluorine Chemistry,*" Synlett, 2001, 9, 1488; Curran D. P., "Fluorous Techniques for the Synthesis of Organic Molecules: A Unified Strategy for Reaction and Separation." In: *Stimulating Concepts in Chemistry* (M. Shibasaki, J. Fraser Stoddart and F. Vögtle, eds.), Wiley-VCH, Weinheim, 2000, 25. Examples of suitable fluorocarbon bonded phases include, but are not limited to, FluoroFlash® columns commercially available from Fluorous Technologies Inc.

(Pittsburgh, Pa.), Fluofix® and Fluophase™ columns commercially available from Keystone Scientific, Inc. (Bellefonte, Pa.), and FluoroSep™-RP-Octyl commercially available from ES Industries (Berlin, N.J.). Other fluorous separation techniques suitable for the present invention include liquid-liquid based separation methods such as liquid-liquid extraction or countercurrent distribution with a fluorous solvent and an organic solvent. Several fluorous reaction and separation techniques are disclosed, for example, in U.S. Pat. Nos. 6,156,896; 5,859,247 and 5,777,121, the disclosures of which are incorporated herein by reference in their entirety. In addition, several fluorous reaction and separation techniques are disclosed in U.S. patent application Ser. Nos. 09/506,779; 09/565,087; 09/583,247; 09/932,903; 09/977,944 and 10/094,345, the disclosures of which are incorporated by reference herein in their entirety. As used herein, the term "catch and release" refers, generally, to the process of tagging (catching) a compound with a tag and then later detagging (releasing) the tagged compound.

As used herein, the terms "alkyl", "aryl" and other groups refer, generally, to both unsubstituted and substituted groups, unless specified to the contrary. Unless otherwise specified, alkyl groups are hydrocarbon groups, and are typically $C_1$–$C_{15}$ (that is, having 1 to 15 carbon atoms) alkyl groups, and may be $C_1$–$C_{10}$ alkyl groups, and can be branched or unbranched, acyclic or cyclic. The above definition of an alkyl group and other definitions apply also when the group is a substituent on another group. The term "aryl" refers to phenyl (Ph) or naphthyl, substituted or unsubstituted.

The groups set forth above, can be substituted with a wide variety of substituents. For example, alkyl groups may be substituted with a group or groups including, but not limited to, halide(s). As used herein, the terms "halide" or "halo" refer to fluoro, chloro, bromo and iodo. Aryl groups may be substituted with a group or groups including, but not limited to, halide(s), alkyl group(s), cyano group(s), and/or nitro group(s) and/or mixtures thereof. Halide substituents, for both alkyl and aryl groups, are typically F and Cl.

As used herein, the term "functional group" refers, generally, to an atom or a group of atoms that has similar chemical properties whenever it occurs in different compounds and confers a specific reactivity to the molecule in which it is contained. For example, functional groups include, but are not limited to, alcohols, thiols, amines, aldehydes, ketones, sulfonic acids, aryl halides, phenols, hydrazines, amino esters, acid chlorides, sulfonyl chlorides, acid anhydrides, chloroformates, isocyanates, isothiocyanates, imines, halides, boronic acids, hydroxylamines, organometallic reagents, carboxylic acids, esters, amides and other derivatives of carboxylic acids. The term "scaffold", as used herein, refers, generally, to a skeletal framework of carbon atoms, in certain cases interspersed with heteroatoms such as, but not limited to, nitrogen, oxygen, sulfur or phosphorous, which is common to all compounds within a specific class of reagents. As used herein, the term "protecting group" refers, generally, to a grouping of atoms that can be readily attached to an organic functional group, such that the organic functional group is rendered less reactive to subsequent chemical transformations. It is a necessary aspect of a protecting group that the grouping of atoms can be readily removed from the substrate after the subsequent chemical transformations to reveal the organic functional group.

As used herein, the term "nucleophilic group" refers generally to an electron rich ion, atom, or group of atoms that can donate a pair of electrons to another atomic nucleus to form a covalent bond or forms an ionic bond with a positively charged ion. The term "electrophilic group" refers generally to an electron deficient ion, atom or group of atoms that accepts a pair of electrons from a nucleophile to form a covalent bond or forms an ionic bond with a negatively charged ion.

As used herein, the term "leaving group" refers generally to an atom or a group of atoms that have the potential to leave a reacting molecule as a relatively stable, weakly basic molecule or ion, when the reacting molecule is attacked by a nucleophile. Attack by the nucleophile results in the formation of a new carbon-nucleophile bond and cleavage of the carbon-leaving group bond. Examples of leaving groups include, but are not limited to, halide, —$N_3$, —CN, —OR, —$ONH_2$, —ONHR, —$ONR_2$, —$O_2CR$, —$O_2COR$, —$O_2CNR_2$, —SR, —OC(S)R, —$S_2CR$, —SC(O)SR, —$S_2CSR$, —$O_2CSR$, —OC(S)OR, —$S_2COR$, $RSO_2$—, $RSO_3$—, $ROSO_2$—, $ROSO_3$—, $RPO_3$—, $ROPO_3$—, an N-imidazolyl group, an N-triazolyl group, an N-benzotriazolyl group, a benzotriazolyloxy group, an imidazolyloxy group, an N-imidazolinone group, an N-imidazolone group, an N-imidazolinethione group, an N-succinimidyl group, an N-phthalimidyl group, an N-succinimidyloxy group, an N-phthalimidyloxy group, —ON=C(CN)R, and a 2-pyridyloxy group, where R is an alkyl, aryl, benzyl or perfluoroalkyl substitutent.

As used herein, the term "electron withdrawing group" refers generally to an electron deficient atom or group of atoms that, when attached to an aromatic ring, withdraws electron density from the aromatic electron system. Examples of electron withdrawing groups include, but are not limited to, halides, nitro group(s), cyano group(s), carbonyl group(s), and sulfonate group(s). Electron withdrawing groups may typically be a chloro, fluoro, nitro and cyano group.

The present invention includes methods and compositions for increasing the fluorous nature of an organic compound by reacting it with at least one fluorous compound to produce a fluorous tagged organic compound. The increased fluorous nature of the fluorous tagged organic compound can then be utilized to separate the fluorous tagged organic compound from untagged reagents, reactants, catalysts and/or products derived therefrom. The resultant fluorous tagged organic compound may be subjected to subsequent chemical transformations, wherein the fluorous nature of the tagged products is utilized to increase the ease of separation of the fluorous tagged organic compound from untagged reagents, reactants, catalysts and/or products derived therefrom, after each chemical transformation. The chemical transformations produce a second fluorous tagged organic compound wherein the fluorous nature of the second fluorous tagged organic compound can then be reduced by removing the fluorous group therefrom, thereby producing a second organic compound whose uses include, but are not limited to, as pharmaceutical compounds or intermediates, and combinatorial library components.

For the further development of fluorous chemistry into a practical strategy in, for example, combinatorial and parallel synthesis, a variety of fluorous tags must be made available. The present invention provides fluorous tags and scavengers that can be prepared in large quantity, can be installed and removed, if necessary, from a substrate using mild reaction conditions, and can be recyclable after cleavage. In addition, the fluorous tags of the present invention are tolerant, as a group, to a wide range of reaction conditions, such that an appropriate tag can be chosen which is amenable to substantially any given sequence of reactions.

The resulting fluorous "tagged" compound can be used in a wide variety of fluorous reaction and can be easily separated from untagged reagents, reactants, catalysts and/or products derived therefrom, using separation techniques that may include standard or fluorous separation techniques known to those of ordinary skill in the art. The tagging compounds of the present invention are particularly suitable for tagging or scavenging of compounds bearing a variety of functional groups.

In a first embodiment, the present invention provides compounds for increasing the fluorous nature of an organic compound having the general structure of:

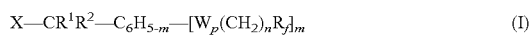

$$X-CR^1R^2-C_6H_{5-m}-[W_p(CH_2)_nR_f]_m \quad (I)$$

that possesses a fluorous substituted benzyl scaffold in which X can be a leaving group, a nucleophilic group or an electrophilic group, wherein the benzylic carbon can be substituted by a variety of potential substituents, $R^1$ and $R^2$. The fluorous compounds are useful for the tagging a variety of functional groups in either tagging or scavenging processes. Functionality reactive with fluorous compound (I) include, but are not limited to, alcohols, amines, thiols carboxylic acids, sufonic acids, aryl halides, acid halides, acid anhydrides, chloroformates, aldehydes, isocyanates, isothiocyanates, sulfonylchlorides, acidic phenols, activated esters, imines, benzyl halides, allyl halides, metals (such as Ni, Pd, etc.), oxidation agents, carbocations, excess acid, hydrazines and/or mixtures thereof.

The phenyl ring of fluorous compound (I) may have up to 5 substitutions, more typically 1 to 3 substitutions, wherein the substituent(s) on the phenyl ring have an increased fluorous nature. The substituent(s) consist of a fluorous group, $R_f$, as defined above which may be attached to the phenyl ring by an methylene spacer consisting of n carbon atoms where n is an integer from 0 to 5 and a possible substituent W (when p is 1) situated between the phenyl ring and the methylene spacer. W may be either carbon or a heteroatom, having the structure O, S, $NR^3$, $CR^4R^5$, or $SiR^6R^7$, wherein $R^3$, $R^4$, and $R^5$ are independently, the same or different, either hydrogen, linear alkyl, branched alkyl, aryl, benzyl or $-(CH_2)_{n'''}R_f$ and $R^6$ and $R^7$ are independently, the same or different, either linear alkyl, branched alkyl, aryl, benzyl and $-(CH_2)_{n'''}R_f$, wherein n''' in an integer from 0 to 5.

Where component X in fluorous compound (I) is a leaving group, then at least one fluorous compound (I) reacts with at least one nucleophilic organic compound via an organic reaction mechanism potentially of the $S_N1$ or $S_N2$ type. The nucleophilic atom of the organic compound replaces the leaving group X, forming at least one covalent bond between the organic compound and $-CR^1R^2-C_6H_{5-m}-[W_p(CH_2)_nR_f]_m$.

Component X in fluorous compound (I) may be a leaving group that is a halide, methane sulfonate, p-toluenesulfonate, trifluoromethanesulfonate or perfluoroalkylsulfonate.

When X is a leaving group, the groups $R^1$ and $R^2$ in fluorous compound (I) may be both hydrogen (except for when both X is bromine and W is silicon) or one or both of $R^1$ and $R^2$ can be alkyl. The resultant compounds are fluorous benzyl-tagging reagents. Like traditional benzyl reagents, the present compound can react with alcohols, thiols, amines, carboxylic acids, sulfonic acids and other nucleophiles. For a general discussion of the use of non-fluorous benzyl reagents, see Greene, T. W.; Wuts, P. G. M. "*Protective Groups in Organic Synthesis,*" 3rd ed., Wiley-Interscience, New York, 1999 and Kocienski, P. "*Protecting Groups,*" Thieme, Stuttgart, 1994. However, the fluorous benzyl tagging reagents of the present aspect have advantages over other traditional non-fluorous benzyl reagents, in that they facilitate separation of the tagged products from each other and from non-tagged reaction components.

Both the groups $R^1$ and $R^2$ in fluorous compound (I), where X is a leaving group, may be phenyl or substituted phenyl. The substituent on the phenyl group may be up to 5 groups, more typically 1 to 3 groups, each independently, the same or different, having the structure, $OR^8$, $SR^9$, $NR^{10}R^{11}$, $CR^{12}R^{13}R^{14}$, $SiR^{15}R^{16}R^{17}$, $[W_{p'}(CH_2)_{n'}R_f]_{m'}$ or $[W_{p''}(CH_2)_{n''}R_f]_{m''}$, where $R^8$, $R^9$, $R^{10}$, $R^{11}$, $R^{12}$, $R^{13}$, and $R^{14}$ are independently, the same or different, either hydrogen, linear alkyl, branched alkyl, aryl, benzyl or $-(CH_2)_{n'''}R_f$, and $R^{15}$, $R^{16}$, and $R^{17}$ are independently, the same or different, either linear alkyl, branched alkyl, aryl, benzyl and $-(CH_2)_{n'''}R_f$, wherein n''' in an integer from 0 to 5. When the substituent is $[W_{p'}(CH_2)_{n'}R_f]_{m'}$ or $[W_{p''}(CH_2)_{n''}R_f]_{m''}$, the substituent(s) consist of a fluorous group, $R_f$, as defined above which may be attached to the phenyl ring by an methylene spacer consisting of n carbon atoms where n' and n'' are each integers from 0 to 5 and a possible substituent W (when p' or p'' is 1) situated between the phenyl ring and the methylene spacer. W may be either carbon or a heteroatom, having the structure O, S, $NR^3$, $CR^4R^5$, or $SiR^6R^7$, wherein $R^3$, $R^4$, and $R^5$ are independently, the same or different, either hydrogen, linear alkyl, branched alkyl, aryl, benzyl or $-(CH_2)_{n'''}R_f$ or $R^6$ and $R^7$ are independently, the same or different, either linear alkyl, branched alkyl, aryl, benzyl and $-(CH_2)_{n'''}R_f$, wherein n''' in an integer from 0 to 5. The resultant compounds are fluorous trityl-tagging reagents. Like traditional trityl tagging reagents, the present compound can react with alcohols, thiols, amines, carboxylic acids, sulfonic acids and other nucleophiles, and/or mixtures thereof. For a general discussion of the use of non-fluorous trityl reagents, see Greene, T. W.; Wuts, P. G. M. "*Protective Groups in Organic Synthesis,*" 3rd ed., Wiley-Interscience, New York, 1999 and Kocienski, P. "*Protecting Groups,*" Thieme, Stuttgart, 1994. However, the fluorous trityl-tagging reagents of the present aspect have advantages over other traditional non-fluorous trityl reagents, in that they facilitate separation of the tagged products from each other and from non-tagged reaction components.

Fluorous benzylating reagents such as fluorous compound (I), where X is a leaving group as defined above, may be prepared by one of various schemes that employ a combination of organic techniques. For example, one possible scheme for the preparation of fluorous benzyl halide is disclosed in Scheme 1.

Scheme 1

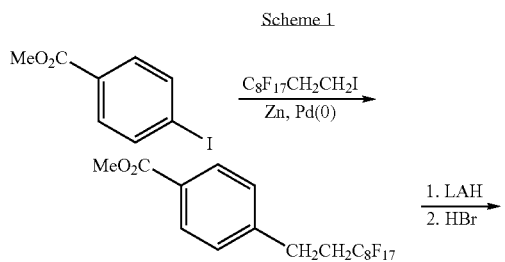

-continued

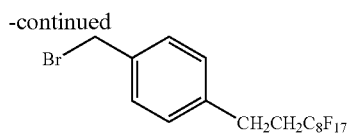

A scheme for the preparation of a fluorous trityl reagent is disclosed in Scheme 2.

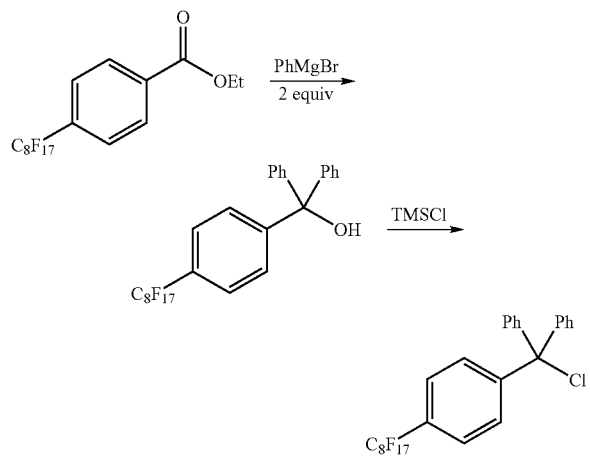

Where component X in fluorous compound (I) is a nucleophilic group, at least one fluorous compound (I) reacts with at least one electrophilic organic compound via an organic reaction mechanism. The chemical reaction results in a chemical bond, either covalent or ionic, between the organic compound and the compound of the present aspect of the invention. Component X in fluorous compound (I) may be a nucleophilic group that is —OH, —NH, —NHR$^{19}$, —NR$^{19}$R$^{20}$, —NHC(=NH)NH$_2$, —SH, —SR$^{19}$, —NH(CH$_2$)$_{n''''}$NH$_2$, or —NH(CH$_2$)$_{n''''}$N((CH$_2$)$_{n''''}$NH$_2$)$_2$, wherein n'''' is an integer from 1 to 5, and R$^{19}$ and R$^{20}$ are independently, the same or different, either a linear alkyl, a branched alkyl, an aryl or a benzyl group.

Where nucleophilic component X in fluorous compound (I) is —SH, the groups R$^1$ and R$^2$ can both be hydrogen, both alkyl or both benzyl groups. In an alternative structure, one of R$^1$ and R$^2$ can be hydrogen and the other alkyl or benzyl. The resultant compounds are fluorous benzyl thiol reagents. Fluorous benzyl thiol reagents can react with numerous electrophilic components, for example, but not limited to, aryl halides, bromomethylcarbonyl compounds, benzyl halides, allyl halides and other electrophiles and/or mixtures thereof. They can also be used in the scavenging of metals including Ni, Pd, and the like.

Where nucleophilic component X in fluorous compound (I) is —SR$^{19}$, the groups R$^1$ and R$^2$ can both be hydrogen, both alkyl or both benzyl groups. In an alternative structure, one of R$^1$ and R$^2$ can be hydrogen and the other alkyl or benzyl. R$^{19}$ can be alkyl, aryl or benzyl. The resultant compounds are fluorous benzyl sulfide reagents. Fluorous benzyl sulfide reagents have potential application including, but not limited to, scavenging oxidation agents and carbocations, for example, carbocations produced in peptide deprotection reactions.

Where nucleophilic component X in fluorous compound (I) is a substituted nitrogen having the structure: —NH$_2$, —NHR$^{21}$, —NR$^{21}$R$^{22}$ or —NR$^{21}$R$^{22}$R$^{23+}$Y$^-$, the groups R$^1$ and R$^2$ can both be hydrogen, both alkyl or both benzyl groups. In an alternative structure, one of R$^1$ and R$^2$ can be hydrogen and the other alkyl or benzyl. R$^{21}$, R$^{22}$ and R$^{23}$ are independently, the same or different, a linear alkyl, a branched alkyl or a benzyl group and Y$^-$ is a counter anion such as, but not limited to, Cl$^-$, Br$^-$, I$^-$ and CO$_3^{2-}$. The resultant compounds are fluorous primary benzylamines, fluorous secondary benzylamines, fluorous tertiary benzylamines and fluorous quaternary benzylammonium salts. Fluorous primary benzylamines, fluorous secondary benzylamines, and fluorous tertiary benzylamines have potential applications including, but not limited to, scavenging excess acid from a reaction or reacting with carboxylic acids, sulfonic acids, acid halides, acid anhydrides, chloroformates, aldehydes, isocyanates, isothiocyanates sulfonylchlorides and other electrophiles and/or mixtures thereof. Fluorous tertiary benzylamines also have the potential application as a base, for example, in combination with other fluorous reagents such as F-Trisamine, F-isocyanate, or F-thiol scavengers (the prefix "F-", as used herein, is an abbreviation of "fluorous"), or in the mesylation reaction of alcohols. Fluorous quaternary benzylammonium salts uses include, but are not limited to, scavenging acids, acidic phenols, activated ester electrophiles and/or mixtures thereof, and having the potential utility to quench reactions and neutralize ammonium salts.

Nucleophilic component X in fluorous compound (I) may be a hydroxyl group, wherein the groups R$^1$ is hydrogen and R$^2$ has the structure C$_6$H$_{5-q}$(W')$_q$. The integer value of q is from 0 to 5, more typically from 0 to 3. W' can be the grouping of atoms OR$^8$, SR$^9$, NR$^{10}$R$^{11}$, CR$^{12}$R$^{13}$R$^{14}$, or SiR$^{15}$R$^{16}$R$^{17}$, wherein R$^8$, R$^9$, R$^{10}$, R$^{11}$, R$^{12}$, R$^{13}$, and R$^{14}$ are independently, the same or different, either hydrogen, linear alkyl, branched alkyl, aryl, benzyl or —(CH$_2$)$_{n'''}$R$_f$ or R$^{15}$, R$^{16}$, and R$^{17}$ are independently, the same or different, either linear alkyl, branched alkyl, aryl, benzyl or —(CH$_2$)$_{n'''}$R$_f$, wherein n''' in an integer from 0 to 5. The resultant compounds are fluorous bisbenzyl alcohols. Fluorous bisbenzyl alcohols uses include, but are not limited to, reacting with alcohols and carboxylic acids and/or mixtures thereof, thereby tagging the compound and simplifying separation/purification.

Nucleophilic component X in fluorous compound (I) may be an amino group, wherein R$^1$ is hydrogen and R$^2$ has the structure C$_6$H$_{5-q}$(W')$_q$. The integer value of q is from 0 to 5, more typically from 0 to 3. W' can be the grouping of atoms OR$^8$, SR$^9$, NR$^{10}$R$^{11}$, CR$^{12}$R$^{13}$R$^{14}$, or SiR$^{15}$R$^{16}$R$^{17}$, wherein R$^8$, R$^9$, R$^{10}$, R$^{11}$, R$^{12}$, R$^{13}$, and R$^{14}$ are independently, the same or different, either hydrogen, linear alkyl, branched alkyl, aryl, benzyl or —(CH$_2$)$_{n'''}$R$_f$ and R$^{15}$, R$^{16}$, and R$^{17}$ are independently, the same or different, either linear alkyl, branched alkyl, aryl, benzyl or —(CH$_2$)$_{n'''}$R$_f$, wherein n''' in an integer from 0 to 5. The resultant compounds are fluorous bisbenzyl amines. Fluorous bisbenzyl amines uses include, but are not limited to, their reaction with carboxylic acids and sulfonic acids and/or mixtures thereof, thereby tagging the compound and simplifying separation/purification.

Where nucleophilic component X in fluorous compound (I) is —NH(CH$_2$)$_{n''''}$NH$_2$, the groups R$^1$ and R$^2$ can both be hydrogen, both alkyl or both benzyl groups. In an alternative structure, one of R$^1$ and R$^2$ can be hydrogen and the other alkyl or benzyl. The integer value for n'''' is 1 to 5. The resultant compounds are fluorous benzyl diamines. Fluorous benzyl diamines have uses including, but not limited to, quenching activated carbonyl acids, sulfonyl halides, isocyanates, isothiocyanates and other electrophiles or mixtures thereof, and also scavenging excess acid. Subsequent to reaction, the tagged compound can be easily removed from the reaction mixture.

Where nucleophilic component X in fluorous compound (I) is —NH(CH$_2$)$_{n''''}$N((CH$_2$)$_{n''''}$NH$_2$)$_2$, the groups R$^1$ and R$^2$ can both be hydrogen, both alkyl or both benzyl groups. In an alternative structure, one of R$^1$ and R$^2$ can be hydrogen and the other alkyl or benzyl. The integer value for n'''' is 1 to 5. The resultant compounds are fluorous benzyl trisamines. Fluorous benzyl trisamines uses include, but are not limited to, their reaction with carboxylic acids, acid chlorides, sulfonyl halides, isocyanates, isothiocyanates, imines and other electrophiles of mixtures thereof, and scavenging excess acid. Subsequent to reaction, the tagged compound can be easily removed from the reaction mixture.

Where nucleophilic component X in fluorous compound (I) is —NHC(=N)NH$_2$, the groups R$^1$ and R$^2$ can both be hydrogen, both alkyl or both benzyl groups. In an alternative structure, one of R$^1$ and R$^2$ can be hydrogen and the other alkyl or benzyl. The resultant compounds are fluorous benzyl guanidines. Fluorous benzyl guanidines have the potential use including, but not limited to, acting as strong organic bases.

Fluorous reagents such as fluorous compound (I), where X is a nucleophilic group as defined above, may be prepared by one of various schemes that employ a combination of organic techniques. For example, one possible scheme for the preparation of fluorous benzyl thiol reagents is disclosed in Scheme 3.

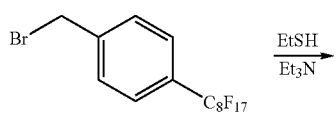

One possible scheme for the preparation of a fluorous benzyl sulfide reagent is disclosed in Scheme 4.

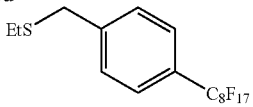

Two possible routes for preparing of fluorous benzylamine reagents are shown in Scheme 5.

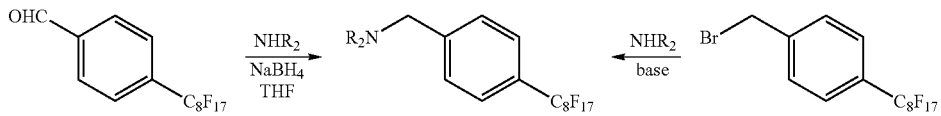

Fluorous quaternary benzylammonium salts can be prepared as set forth in Scheme 6.

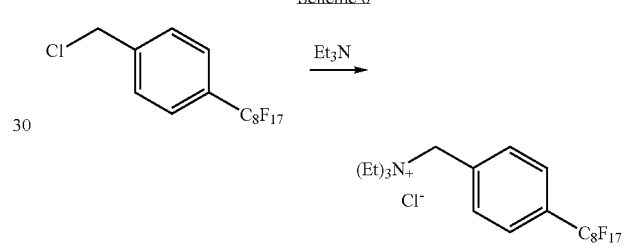

Fluorous bisbenzyl alcohols may be prepared by addition of a substituted phenyl Grignard reagent to a fluorous benzaldehyde as shown in Scheme 7.

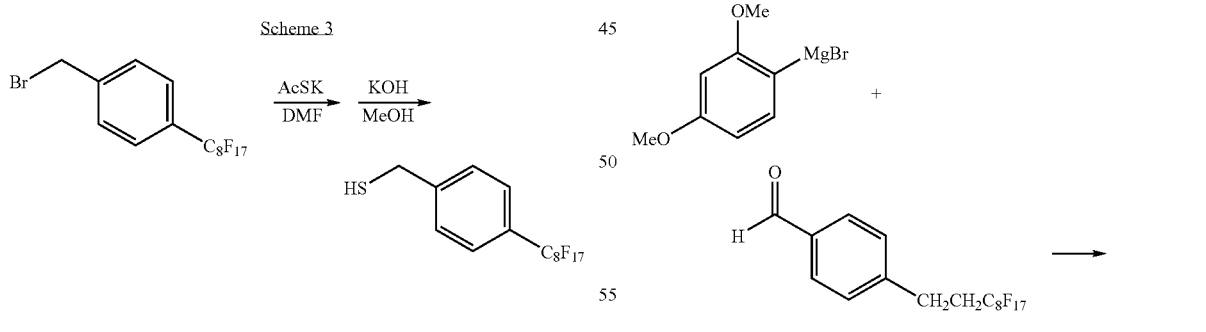

Fluorous bisbenzyl amines may be prepared from fluorous bisbenzyl alcohols through the chemical transformations shown in Scheme 8.

Scheme 8

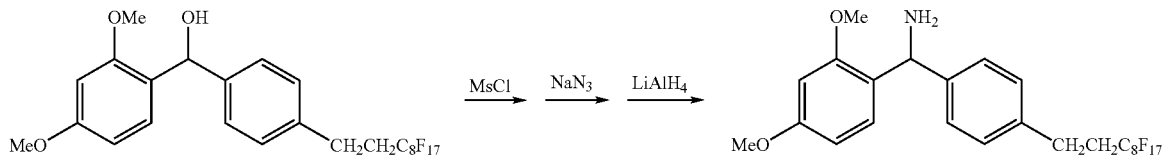

A route to a fluorous benzyl diamine is shown in Scheme 9 and an analogous route to a fluorous benzyl trisamine is depicted in Scheme 10.

Scheme 9

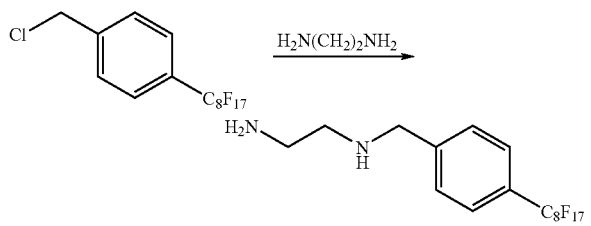

Scheme 10

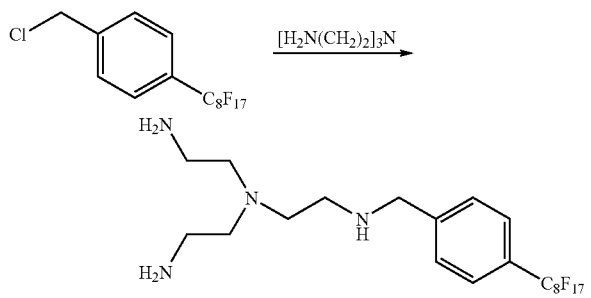

An approach to a fluorous benzyl guanidine is depicted in Scheme 11.

Scheme 11

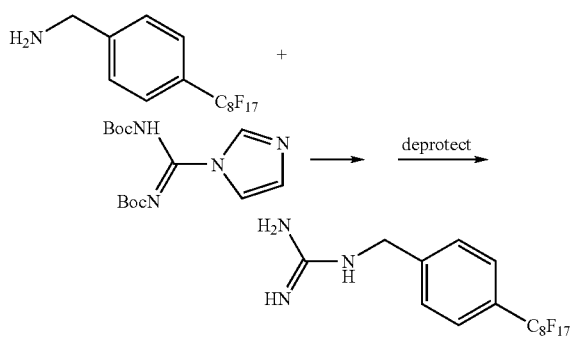

The fluorous nucleophilic benzyl tags and scavengers discussed above may be synthesized using one or more of the synthetic approaches set forth in Schemes 1–11.

Where component X in fluorous compound (I) is an electrophilic group, at least one fluorous compound (I) reacts with at least one nucleophilic organic compound via an organic reaction mechanism. The chemical reaction results in a chemical bond, either covalent or ionic, between the organic compound and the compound of the present aspect of the invention.

Where electrophilic component X in fluorous compound (I) is the electrophilic group comprising either an isocyanate group or an isothiocyanate group, the groups $R^1$ and $R^2$ can both be hydrogen, both alkyl or both benzyl groups. In an alternative structure, one of $R^1$ and $R^2$ can be hydrogen and the other alkyl or benzyl. The resultant compounds are fluorous benzyl isocyanates and isothiocyanates. Fluorous benzyl isocyanates and isothiocyanates have uses including, but not limited to, their reaction with amines, hydrazines and other nucleophiles or mixtures thereof, for the purpose of tagging/scavenging those compounds for separation from the reaction mixture.

Fluorous reagents such as fluorous compound (I), where X is an electrophilic group, may be prepared by one of various schemes that employ a combination of organic techniques. For example, one possible scheme for the preparation of fluorous isocyanate and isothiocyanate reagents is disclosed in Scheme 12.

Scheme 12

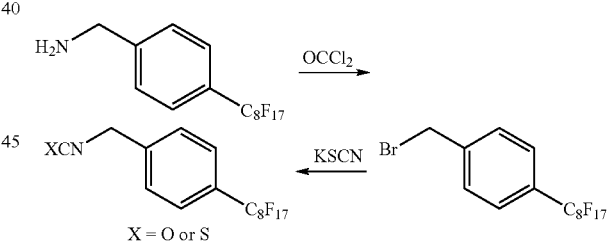

X = O or S

In an alternative structure to the structures comprising fluorous compound (I), $R_f$ is a fluorous group selected from a perfluorocarbon, a fluorohydrocarbon, a fluorinated ether or a fluorinated amine.

The present invention also provides a method for increasing the fluorous nature of an organic compound, including reacting the organic compound with at least one second compound having the general structure of fluorous compound (I) as described above, to create a first fluorous tagged organic compound. The organic compound will have at least one functional group reactive with group X on the fluorous second compound (I) forming at least one chemical bond between the organic compound and the fluorous second compound (I), resulting in the first fluorous tagged organic compound. The fluorous nature of the first fluorous tagged organic compound is increased relative to the organic compound to enable separation of the first fluorous tagged organic compound from at least one other compound by using separation techniques that may include standard or fluorous separation techniques known to those of ordinary skill in the art.

In the method for increasing the fluorous nature of an organic compound by reacting it with at least one second compound having the structure of fluorous compound (I), described above, wherein X is a leaving group, the leaving group X in fluorous compound (I) may be those leaving groups defined above. Where fluorous compound (I) is a benzyl tagging reagent, as described above, the resultant fluorous benzyl-tagging reagents have uses including, but not limited to, tagging alcohols, thiols, amines, carboxylic acids, sulfonic acids and other nucleophilic organic compounds and/or mixtures thereof, wherein the fluorous benzyl tagged compounds can be separated from other reaction components through separation techniques that may include standard or fluorous separation techniques known to those of ordinary skill in the art. Where fluorous compound (I) is a trityl tagging reagent, as described above, the resultant fluorous trityl-tagging reagents have uses including, but not limited to, the tagging of alcohols, thiols, amines, carboxylic acids, sulfonic acids and other nucleophiles and/or mixtures thereof, wherein the fluorous trityl tagged compounds can be separated from other reaction components through separation techniques that may include standard or fluorous separation techniques known to those of ordinary skill in the art.

In the method for increasing the fluorous nature of an organic compound by reacting it with at least one second compound having the structure of fluorous compound (I), described above, wherein X is a nucleophilic group, the nucleophilic group X in fluorous compound (I) may be those nucleophilic groups defined above, and at least one fluorous compound (I) reacts with at least one electrophilic organic compound via an organic reaction mechanism. The chemical reaction results in a chemical bond, either covalent or ionic, between the organic compound and the compound of the present aspect of the invention. In the above method of the present invention, the fluorous tagged or scavenged organic compounds can then be separated from the reaction mixture by a separation technique that may include a standard or fluorous separation technique known to those skilled in the art. The tagged compounds may then be subjected to subsequent chemical transformations.

In the method for increasing the fluorous nature of an organic compound by reacting it with at least one second compound having the structure (I) where component X in fluorous compound (I) may be an electrophilic group as defined above, at least one fluorous compound (I) reacts with at least one nucleophilic organic compound via an organic reaction mechanism. The chemical reaction results in a chemical bond, either covalent or ionic, between the organic compound and the compound of the present aspect of the invention. Where electrophilic component X in fluorous compound (I) is the electrophilic group comprising either an isocyanate group or an isothiocyanate group, the resultant compounds are fluorous benzyl isocyanates and isothiocyanates. Fluorous benzyl isocyanates and isothiocyanates have uses including, but not limited to, reacting with amines, hydrazines and other nucleophilic reagents and/or mixtures thereof, wherein the fluorous tagged compounds can be separated from other reaction components through separation techniques that may include standard or fluorous separation techniques known to those of ordinary skill in the art.

In addition, the method of the present invention may further include reducing the fluorous content of a second fluorous-tagged organic compound that is tagged with fluorous compound (I). In this aspect of the invention, the first fluorous-tagged organic compound, in which the tag is from fluorous compound (I), is subjected to at least one chemical reaction and potentially at least one purification process. The chemical reaction(s) produces the second fluorous-tagged organic compound, in which the tag is from fluorous compound (I), which is isolated and subjected to the fluorous content reducing step. The resultant molecules may have uses that include, but are not limited to, pharmaceutical compounds or intermediates, and combinatorial library components.

The fluorous nature of the second fluorous-tagged organic compound may be reduced by removing at least one grouping of atoms having the possible structure: $-CR^1R^2-C_6H_{5-m}-[W_p(CH_2)_nR_f]_m$, $-C_6H_{5-m}-[W_p(CH_2)_nR_f]_m$, $-[W_p(CH_2)_nR_f]_m$, $(CH_2)_nR_f$, or $R_f$ from the second fluorous tagged organic compound.

In another embodiment, the present invention provides compounds for increasing the fluorous nature of an organic compound having the general structure of:

$$XCO_2CH_2R_d \quad (II)$$

wherein X is a leaving group and $R_d$ has the structure selected from:

a) $-CH=CH-(CH_2)_nR_f$, b)

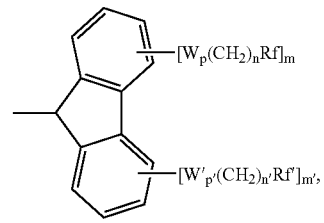

or c) $-C_6H_{5-m''}[W_p(CH_2)_nR_f]_{m''}$. $R_f$ and $R_{f'}$ are each fluorous groups. The integer value for m is from 1 to 4, m' is an integer from 0 to 4, and m" is an integer from 1 to 5, more typically from 1 to 3. The integer values for n and n' are each from 0 to 5 and p and p' each has a value of either 0 or 1. W and W' are atoms or groupings of atoms each having the possible structure of O, S, $NR^{25}$, $CR^{26}R^{27}$, or $SiR^{28}R^{29}$. The substituents $R^{25}$, $R^{26}$ and $R^{27}$ are independently, the same or different, either hydrogen, linear alkyl, branched alkyl, aryl, benzyl or $(CH_2)_nR_f$ and the substituents $R^{28}$ and $R^{29}$ are independently, the same or different, either linear alkyl, branched alkyl, aryl, benzyl or $-(CH_2)_nR_f$.

Component X in fluorous compound (II) may be various leaving groups suitable for use in the present invention and known to those skilled in the art. X may be a leaving group with a structure consisting of a halide, $-N_3$, $-CN$, $-OR^{30}$, $-ONH_2$, $-ONHR^{30}$, $ONR^{30}_2$, $-O_2CR^{30}$, $-O_2COR^{30}$, $-O_2CNR^{30}_2$, $-SR^{30}$, $-OC(S)R^{30}$, $R^{30}CS_2-$, $-SC(O)SR^{30}$, $-SCS_2R^{30}$, $-OC(O)SR^{30}$, $-OC(S)OR^{30}$, $-SC(S)OR^{30}$, $R^{30}SO_2-$, $R^{30}SO_3-$, $R^{30}OSO_2-$, $R^{30}OSO_3-$, $R^{30}PO_3-$, $R^{30}OPO_3-$, an N-imidazolyl group, an N-triazolyl group, an N-benzotriazolyl group, a benzotriazolyloxy group, an imidazolyloxy group, an N-imidazolinone group, an N-imidazolone group, an N-imidazolinethione group, an N-succinimidyl group, an N-phthalimidyl group, an N-succinimidyloxy group, an N-phthalimidyloxy group, $-ON=C(CN)R^{30}$, or a 2-pyridyloxy group, wherein $R^{30}$ is one of linear alkyl, branched alkyl, aryl, benzyl, or $-(CH_2)_{n''}R_f$, wherein n" in an integer from 0 to 5.

For the purpose of this embodiment, $R_f$ and $R_f'$ may be independently, the same or different, selected from a perfluorocarbon, a fluorohydrocarbon, a fluorinated ether or a fluorinated amine.

Where $R_d$ of fluorous compound (II) has the structure —CH=CH—(CH$_2$)$_n$R$_f$ (i.e. group (a)), the resultant compounds are fluorous allyloxycarbonyl reagents (F-Alloc). Where $R_d$ in fluorous compound (II) has the structure:

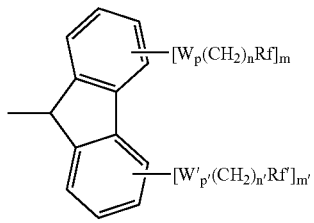

(i.e. group (b)), the resultant compounds are fluorous 9-fluorenylmethoxycarbonyl reagents (F-Fmoc). Where $R_d$ in fluorous compound (II) has the structure —C$_6$H$_{5-m''}$[W$_p$(CH$_2$)$_n$R$_f$]$_{m''}$ (i.e. group (c)), the resultant compounds are fluorous carboxybenzyl reagents (F-Cbz). Like traditional allyloxycarbonyl, 9-fluorenylmethoxycarbonyl, and carboxybenzyl reagents, the present compounds can react with amines. For a general discussion of the use of non-fluorous allyloxycarbonyl, 9-fluorenylmethoxycarbonyl, and carboxybenzyl reagents, see Greene, T. W.; Wuts, P. G. M. "*Protective Groups in Organic Synthesis,*" 3rd ed., Wiley-Interscience, New York, 1999 and Kocienski, P. "*Protecting Groups,*" Thieme, Stuttgart, 1994. However, the fluorous allyloxycarbonyl, fluorous 9-fluorenylmethoxycarbonyl, and fluorous carboxybenzyl tagging reagents of the present invention have advantages over other traditional non-fluorous allyloxycarbonyl, 9-fluorenylmethoxycarbonyl, and carboxybenzyl reagents, respectively, in that the fluorous tagging reagents of the present invention tag the organic compound and facilitate separation of the tagged products from each other and from non-tagged reaction components.

Fluorous reagents such as fluorous compound (II), where $R_d$ may have the structures as described, may be prepared by one of various schemes that employ a combination of organic techniques. For example, one possible scheme for the preparation of fluorous allyloxycarbonyl reagents is disclosed in Scheme 13.

Scheme 13

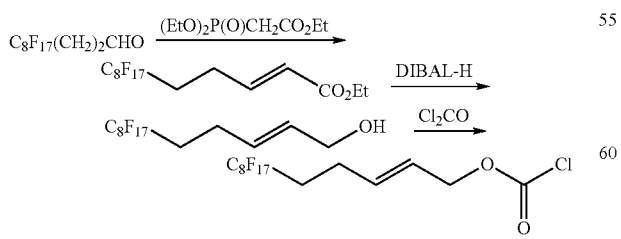

A synthetic approach to fluorous fluorenylmethoxycarbonyl (F-Fmoc) reagents is depicted in Scheme 14.

Scheme 14

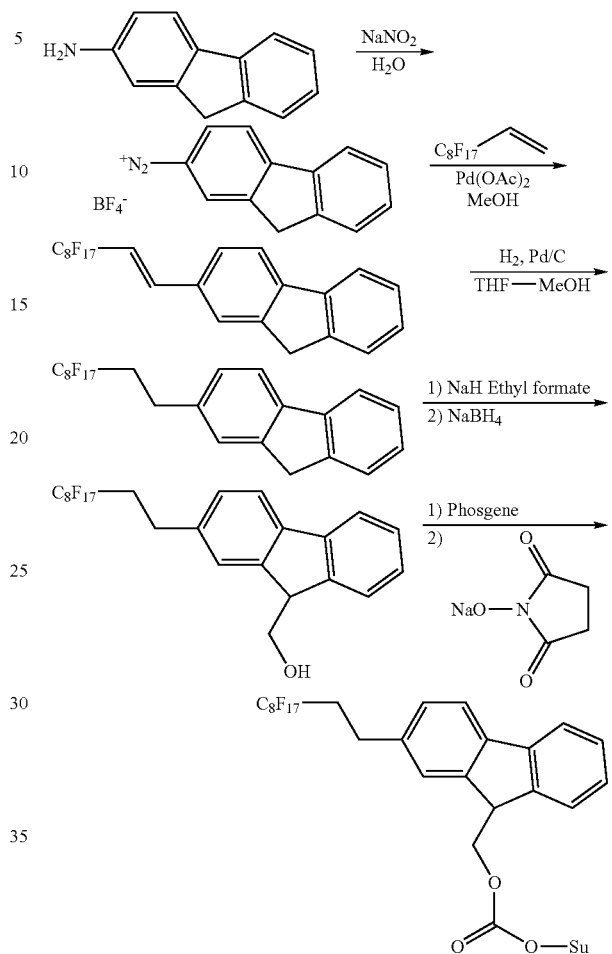

Fluorous carboxybenzyl reagents may be prepared using the approach as depicted in Scheme 15.

Scheme 15

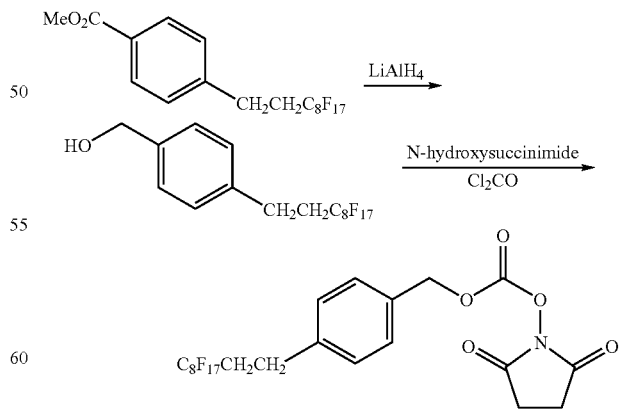

The present invention also provides a method for increasing the fluorous nature of an organic compound that includes reacting the organic compound with at least one second compound having the general structure of fluorous compound (II), described above. The organic compound will have at least one functional group reactive with leaving group X on the second compound forming at least one chemical bond between the organic compound and the second compound resulting in the first fluorous tagged organic compound. The fluorous nature of the first fluorous tagged organic compound is increased relative to the organic compound to enable separation of the first fluorous tagged organic compound from at least one other compound by using separation techniques that may include standard or fluorous separation techniques known to those of ordinary skill in the art.

In the method for increasing the fluorous nature of an organic compound by reacting it with at least one second compound having the structure (II), described above, wherein component X is a leaving group, the leaving group X in fluorous compound (II) may be those leaving groups defined above. Where fluorous compound (II) is F-Alloc, F-Fmoc or F-Cbz reagent described above, the resultant F-Alloc, F-Fmoc, or F-Cbz reagents, respectively, have uses that include, but are not limited to, reacting with amines such that the fluorous tagged amines may be readily separated from other fluorous or non-fluorous reaction components.

In addition, the method of the present invention may further include reducing the fluorous content of a second fluorous-tagged organic compound that is tagged with fluorous compound (II). In this aspect of the invention, the first fluorous-tagged organic compound, in which the tag is from fluorous compound (II), is subjected to at least one chemical reaction and potentially at least one purification process. The chemical reaction(s) produces the second fluorous-tagged organic compound, in which the tag is from fluorous compound (II), which is isolated and subjected to the fluorous content reducing step. The resultant molecules may have uses that include, but are not limited to, pharmaceutical compounds or intermediates, and combinatorial library components.

The fluorous nature of the second fluorous-tagged organic compound may be reduced by removing at least one grouping of atoms having the possible structure: —$CO_2CH_2R_d$, —$OCH_2R_d$, $R_d$, and $R_f$ from the second fluorous tagged organic compound.

In yet another embodiment, the present invention provides compounds for increasing the fluorous nature of an organic compound having the general structure of:

$$R^{31}R^{32}N(CH_2)_nR_f \qquad (III)$$

wherein n is an integer from 0 to 5, $R_f$ is a fluorous group, and $R^{31}R^{32}$ is selected from:

a) —$(CH_2)_mW(CH_2)_{m'}$—, wherein m and m' are each integers between 2 and 4, W is one of $CH_2$, O, S, NH, and $NR^{33}$, wherein $R^{33}$ is one of a linear alkyl, a branched alkyl and a benzyl group, b) 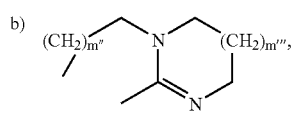

wherein m" and m'" are each integers from 0 to 3, c) 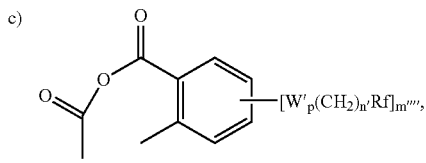

wherein W' is a grouping of atoms selected from the group consisting of O, S, $NR^{34}$, $CR^{35}R^{36}$, $SiR^{37}R^{38}$, p has a value of 0 or 1, n' is an integer from 0 to 5, m"" is an integer from 0 to 4, more typically from 0 to 2, $R^{34}$, $R^{35}$, and $R^{36}$ are independently, the same or different, one of hydrogen, linear alkyl, branched alkyl, aryl, benzyl and —$(CH_2)_nR_f$, and $R^{37}$ and $R^{38}$ are independently, the same or different, one of linear alkyl, branched alkyl, aryl, benzyl and —$(CH_2)_nR_f$, d) alkyl and pyridyl, e) hydrogen and —$(CH_2)_{n"}NH_2$, wherein n" is an integer from 1 to 5, f) hydrogen and —$(CH_2)_{n"}N[(CH_2)_{n"}NH_2]_2$, or g) —$(CH_2)_{n'"}OH$, and —$(CH_2)_{n""}OH$, wherein n'" and n"" are each integers between 1 and 5.

For the purpose of this embodiment, $R_f$ may be a perfluorocarbon, a fluorohydrocarbon, a fluorinated ether or a fluorinated amine.

In fluorous compound (III), the groups $R^{31}R^{32}$, taken together, may be —$(CH_2)_mW(CH_2)_{m'}$—, forming a cyclic amine, where W, m and m' are as defined above. The resultant compounds are fluorous cyclic amines that have various applications including, but not limited to, acting as a tertiary amine to catalyze reactions, as a catalyst in the functionalization of secondary amines with acid chlorides and as a scavenger to remove excess acid.

For fluorous compound (III), the groups, $R^{31}R^{32}$, taken together, may have the structure:

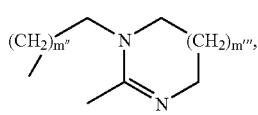

forming a bicyclic amine, wherein m" and m'" are each integers from 0 to 3. The resultant compounds are fluorous bicyclic amines that have potential utility as, but not limited to, a fluorous basic catalyst for regioselective acylation, as both a base for the deprotonation of phenols and as a scavenger of excess phenol in the synthesis of aryl ethers, in the addition of dialkyl phosphates to a variety of carbonyl compounds, as a catalyst in the nitroaldol reaction and as a scavenger of activated ester electrophiles.

For fluorous compound (III), the groups $R^{31}R^{32}$, taken together, may have the structure:

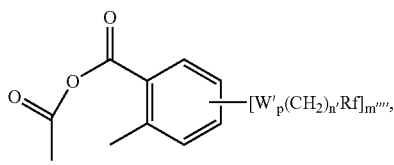

forming a cyclic isatoic anhydride, wherein W', p, n', and m'''' are as defined above. The resultant compounds are fluorous isatoic anhydrides that have potential applications including, but not limited to, the scavenging of primary and secondary amines, and/or mixtures thereof, wherein the scavenged amines may be removed from the reaction mixture through separation techniques that may include standard or fluorous separation techniques known to those of ordinary skill in the art.

In fluorous compound (III), the nitrogen may be substituted where $R^{31}$ is one of linear alkyl and branched alkyl, and $R^{32}$ is a pyridyl ring, wherein the nitrogen may be attached to the pyridyl ring at the 2, 3, or 4 position. The resultant compounds are fluorous aminopyridines. Uses of fluorous aminopyridines include, but are not limited to, as an equivalent to dimethylaminopyridine for the catalysis of acylation or esterification reactions, and as a reagent for the "catch and release" of acid chlorides and sulfonyl chlorides in the synthesis of acyl and sulfonyl derivatives, including esters, amides, sulfonamides and/or mixtures thereof.

The nitrogen of fluorous compound (III) may also be substituted where $R^{31}$ is hydrogen and $R^{32}$ is $CH_2)_{n''}NH_2$, wherein n'' is an integer from 1 to 5. The resultant compounds are fluorous alkyldiamines. Fluorous alkyldiamines have uses including, but not limited to, quenching activated carbonyl acids, sulfonyl halides, isocyanates, isothiocyanates and other electrophiles and/or mixtures thereof, and also the scavenging of excess acid.

The nitrogen of fluorous compound (III) may also be substituted where $R^{31}$ is hydrogen and $R^{32}$ is $-(CH_2)_{n''}N[(CH_2)_{n''}NH_2]_2$, wherein n'' is an integer from 1 to 5. The resultant compounds are fluorous alkyl(trisaminoalkyl) amines. Fluorous alkyl(trisaminoalkyl) amines have uses including, but not limited to, quenching activated carbonyl acids, sulfonyl halides, isocyanates, isothiocyanates and other electrophiles and/or mixtures thereof. The compounds can also be useful in the scavenging of excess acid.

The nitrogen of fluorous compound (III) may also be substituted wherein $R^{31}$ is $-(CH_2)_{n'''}OH$, and $R^{32}$ is $-(CH_2)_{n''''}OH$, wherein n''' and n'''' are each integers between 1 and 5. The resultant compounds are fluorous N,N-dihydroxyalkylamines. Fluorous N,N-dihydroxyalkylamines have uses including, but not limited to, quenching of boronic acids. The quenched boronic acids may then be readily removed from the reaction mixture through separation techniques that may include standard or fluorous separation techniques known to those of ordinary skill in the art.

Fluorous reagents such as (III), where the groups $R^{31}R^{32}$ have the structures as described, may be prepared by one of various schemes that employ a combination of organic techniques. For example, one possible scheme for the preparation of fluorous cyclic amine reagents is disclosed in Scheme 16.

Scheme 16

An approach to fluorous reagent (III), wherein compound (III) is a bicyclic amine, is depicted in Scheme 17.

Scheme 17

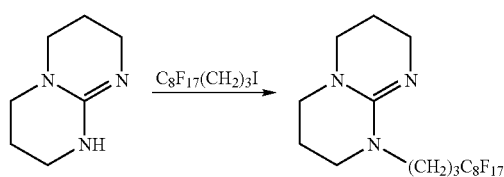

Where fluorous compound (III) is a fluorous isatoic anhydride, the present embodiment may be prepared as shown in Scheme 18.

Scheme 18

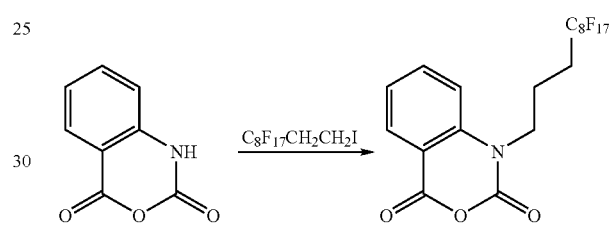

Fluorous aminopyridine reagents may be prepared as shown in Scheme 19.

Scheme 19

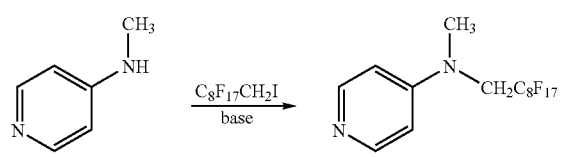

Where fluorous compound (III) is a fluorous alkyl diamine (Scheme 20) or a fluorous alkyl(trisaminoalkyl) amines (Scheme 21), the present embodiment may be prepared as shown below.

Scheme 20

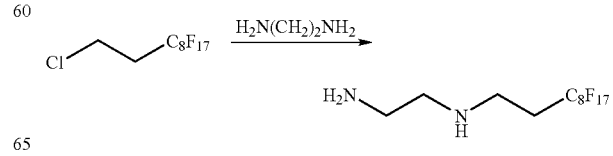

Scheme 21

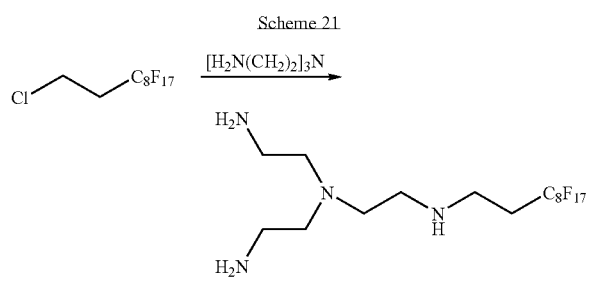

Fluorous N,N-dihydroxyalkylamines may be prepared as shown in Scheme 22.

Scheme 22

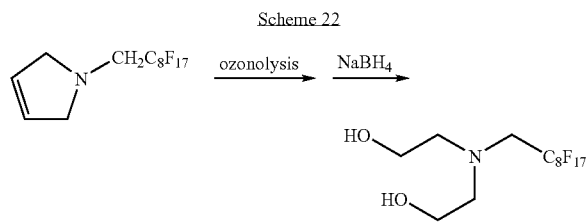

The present invention also provides a method for increasing the fluorous nature of an organic compound, including the step of reacting the organic compound with at least one second compound having the structure of fluorous compound (III), wherein the groups $R^{31}R^{32}$ may be as described above, to create a first fluorous tagged organic compound. The organic compound having at least one functional group reactive with at least one N or —OH group on the second compound (III) forming at least one chemical bond between the organic compound and the second compound (III) resulting in the first fluorous tagged organic compound. The fluorous nature of the first fluorous tagged organic compound is increased relative to the organic compound to enable separation of the first fluorous tagged organic compound from at least one other compound by using separation techniques that may include standard or fluorous separation techniques known to those of ordinary skill in the art. The tagged compounds may then be subjected to subsequent chemical transformations.

In addition, the method of the present invention may further include reducing the fluorous content of a second fluorous-tagged organic compound that is tagged with fluorous compound (III). In this aspect of the invention, the first fluorous-tagged organic compound, in which the tag is from fluorous compound (III), is subjected to at least one chemical reaction and potentially at least one purification process. The chemical reaction(s) produces the second fluorous-tagged organic compound, in which the tag is from fluorous compound (III), which is isolated and subjected to the fluorous content reducing step. The resultant molecules may have uses that include, but are not limited to, pharmaceutical compounds or intermediates, and combinatorial library components.

The fluorous nature of the second fluorous-tagged organic compound may be reduced by removing at least one grouping of atoms having the possible structure: $R^{31}R^{32}N(CH_2)_nR_f$, —$N(CH_2)_nR_f$, —$(CH_2)_nR_f$ or $R_f$ from the second fluorous tagged organic compound.

In a further embodiment, the present invention provides compounds for increasing the fluorous nature of an organic compound having the general structure of:

$$X-C_6H_{5-m}-[W_p(CH_2)_nR_f]_m \qquad (IV)$$

wherein $R_f$ is a fluorous group, m has an integer value from 1 to 5, more typically from 1 to 3, n has an integer value from 0 to 5, p is either 0 or 1 and W is an atom or grouping of atoms having the structure of O, S, $NR^{39}$, $CR^{40}R^{41}$, or $SiR^{42}R^{43}$. When W is O, then X has the structure —$SO_2NHNH_2$, —CHO when p is 1, —SH, $(CH_2)_{n'}SH$, —$C(=NOH)C_6H_4Y$, or —$C(=O)CH_2C(=O)R^{44}$. When W is S, $NR^{39}$, $CR^{40}R^{41}$, or $SiR^{42}R^{43}$, then X has the structure —$SO_2NH_2$, —$SO_2NHNH_2$, —CHO when p is 1, —SH, —$(CH_2)_{n'}SH$, —$C(=NR^B)C_6H_4Y$, or —$C(=O)CH_2C(=O)R^{44}$. Z is either oxygen or sulfur. Y is either an electron withdrawing group, a hydrogen or an alkyl group and $R^B$ is either a hydrogen, an alkyl, an aryl or a hydroxyl group. The integer value of n' is from 2 to 5. $R^{39}$, $R^{40}$ and $R^{41}$ are independently, the same or different, either hydrogen, linear alkyl, branched alkyl, aryl, benzyl or —$(CH_2)_nR_f$, and $R^{42}$ and $R^{43}$ are independently, the same or different, either linear alkyl, branched alkyl, aryl, benzyl or —$(CH_2)_nR_f$. $R^{44}$ is linear alkyl, branched alkyl or benzyl.

For the purpose of this embodiment, $R_f$ may be a perfluorocarbon, a fluorohydrocarbon, a fluorinated ether or a fluorinated amine.

Where component X in fluorous compound (IV) is —$SO_2NH_2$, the structure of W may be S, $NR^{39}$, $CR^{40}R^{41}$, or $SiR^{42}R^{43}$. The resultant compounds are fluorous benzenesulfonamides. Fluorous benzenesulfonamides have uses including, but not limited to, scavenging acids, acid chlorides, anhydrides, aldehydes, isocyanates, isothiocyanates chloroformates and other electrophiles and/or mixtures thereof. The scavenged compounds can be separated from the reaction mixture using separation techniques that may include standard or fluorous separation techniques known to those of ordinary skill in the art.

Where component X in fluorous compound (IV) is —$SO_2NHNH_2$, the resultant structures are fluorous sulfonylhydrazides. Fluorous sulfonylhydrazides have uses including, but not limited to, scavenging aldehydes and ketones and/or mixtures thereof. The scavenged compounds can be separated from the reaction mixture using separation techniques that may include standard or fluorous separation techniques known to those of ordinary skill in the art.

Where component X in fluorous compound (IV) is —CHO, the value of p is 1. The resultant structures are fluorous benzaldehydes. Fluorous benzaldehydes have uses including, but not limited to, selectively scavenging primary amines, hydrazines, hydroxylamines, 1,2-aminothiols, Grignard reagents, other organometallic reagents and/or mixtures thereof. The scavenged compounds can be separated from the reaction mixture using separation techniques that may include standard or fluorous separation techniques known to those of ordinary skill in the art.

Where component X in fluorous compound (IV) is —SH or —$(CH_2)_{n'}SH$, where the integer value of n' is from 2 to 5, the resultant structures are fluorous benzenethiols or fluorous arylalkylthiols, respectively. Fluorous benzenethiols and fluorous arylalkylthiols have uses including, but not limited to, reacting with numerous electrophilic components, for example, aryl halides, bromomethylcarbonyl compounds, benzyl halides, allyl halides and other electrophiles, and/or mixtures thereof. They can also be used in the scavenging of metals such as Ni, Pd, and the like. The scavenged or tagged compounds can be separated from the reaction mixture using separation techniques that may include standard or fluorous separation techniques known to those of ordinary skill in the art.

Component X in fluorous compound (IV) may be —C(=NR$^B$)C$_6$H$_4$Y, where Y is an electron withdrawing group, a hydrogen or an alkyl group and R$^B$ is a hydrogen, an alkyl group, and aryl group or a hydroxyl group. Where Y is an electron withdrawing group, it may be selected from nitro, cyano, fluoro, or chloro. The resultant compounds are fluorous benzylimines (when R$^B$ is hydrogen, alkyl or aryl), or benzyloximes (when R$^B$ is hydroxyl), which have uses including, but not limited to, tagging of carboxylic acids. The tagged compounds can be separated from the reaction mixture using separation techniques that may include standard or fluorous separation techniques known to those of ordinary skill in the art.

Component X in fluorous compound (IV) may also be —C(=O)CH$_2$C(=O)R$^{44}$, where R$^{44}$ is linear alkyl, branched alkyl or benzyl. The resultant compounds are fluorous aryl-1,3-diketones. Fluorous aryl-1,3-diketones have uses including, but not limited to, scavenging primary amines in the presence of secondary amines. The scavenged compounds can be separated from the reaction mixture using separation techniques that may include standard or fluorous separation techniques known to those of ordinary skill in the art.

Fluorous reagents such as (IV), where component X is as described above, may be prepared by one of various schemes that employ a combination of organic techniques. For example, one possible scheme for the preparation of fluorous benzenesulfonamide reagents is disclosed in Scheme 23.

Scheme 23

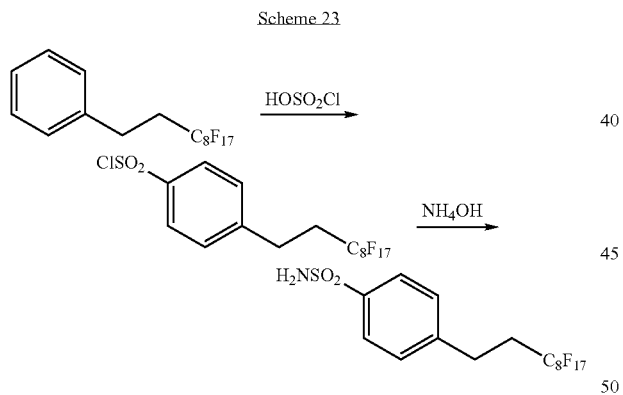

A possible route for the synthesis of fluorous benzenesulfonylhydrazide is depicted in Scheme 24.

Scheme 24

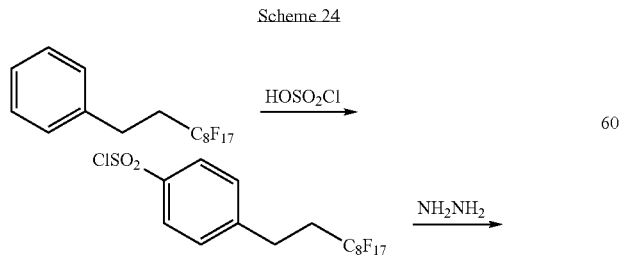

-continued

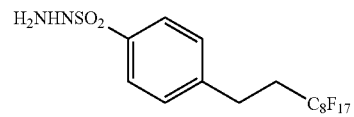

Scheme 25 provides a route to fluorous benzaldehydes.

Scheme 25

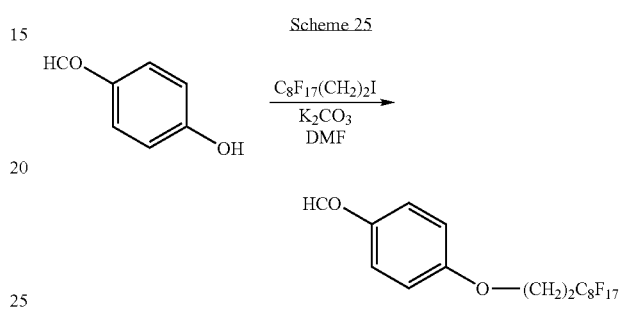

Fluorous arylalkylthiols may be synthesized using the approach depicted in Scheme 26.

Scheme 26

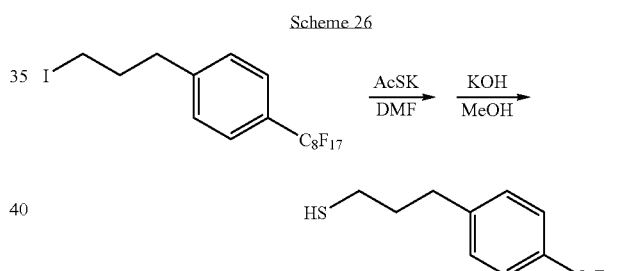

One possible approach to fluorous benzyloximes is shown in Scheme 27.

Scheme 27

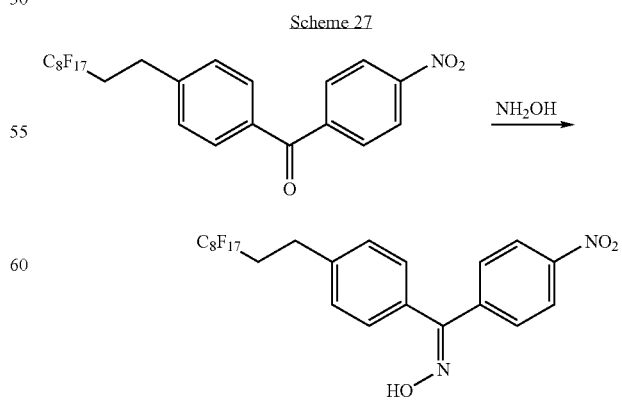

Fluorous aryl-1,3-diketones may be synthesized using an approach as shown in Scheme 28.

Scheme 28

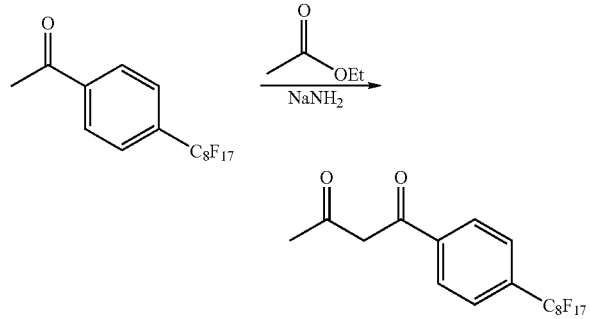

The present invention also provides a method for increasing the fluorous nature of an organic compound, including the step of reacting the organic compound with at least one second compound having the structure of fluorous compound (IV), where component X is as described above and also including where component X of fluorous compound (IV) may be the group —COCl, —SO$_2$Cl, —OH, —NCZ, or —SO$_3$H, to create a first fluorous tagged organic compound. The organic compound has at least one functional group that reacts with group X on at least one second fluorous compound (IV) to form at least one chemical bond between the organic compound and at least one second fluorous compound (IV). The chemical reaction results in a first fluorous tagged organic compound with an increased fluorous nature relative to the fluorous nature of the organic compound. The increased fluorous nature of the first fluorous tagged organic compound enables separating the first fluorous tagged organic compound from other compounds by use of separation techniques that may include separation techniques that may include standard or fluorous separation techniques known to those of ordinary skill in the art. The tagged compounds may then be subjected to subsequent chemical transformations.

The present invention may also provide a method for increasing the fluorous nature of an organic compound by reacting it with at least one second compound (IV), where component X in fluorous compound (IV) may be —COCl. The resultant compounds are fluorous benzoyl chlorides. Fluorous benzoyl chlorides react alcohols, amines, thiols, and other nucleophiles, and/or mixtures thereof, through a nucleophilic acyl substitution process to produce a fluorous tagged organic compound.

The present invention may also provide a method for increasing the fluorous nature of an organic compound by reacting it with at least one second compound (IV), where component X in fluorous compound (IV) may be —SO$_2$Cl. The resultant compounds are fluorous benzenesulfonyl chlorides that have uses including, but not limited to, tagging and scavenging alcohols, amines, thiols and other nucleophiles, and/or mixtures thereof.

The present invention may further provide a method for increasing the fluorous nature of an organic compound by reacting it with at least one second compound (IV), where component X in fluorous compound (IV) may be —OH. The resultant compounds are fluorous phenols that have uses including, but not limited to, tagging carboxylic acids.

The present invention may also provide a method for increasing the fluorous nature of an organic compound by reacting it with at least one second compound (IV), where component X in fluorous compound (IV) may be —NCZ, where Z is either oxygen or sulfur. The resultant compounds are fluorous phenyl isocyanates or fluorous phenyl isothiocyanates that have uses including, but not limited to, scavenging amines, hydrazines and other nucleophiles, and/or mixtures thereof.

The present invention may further provide a method for increasing the fluorous nature of an organic compound by reacting it with at least one second compound (IV), where component X in fluorous compound (IV) may be —SO$_3$H. The resultant compounds are fluorous benzene sulfonic acids that have uses including, but not limited to, scavenging amines, alcohols and other nucleophiles, and/or mixtures thereof.

In the present method, when component X of fluorous compound (IV) is as described above, the organic compounds that are reacted with fluorous compound (IV) can be separated from the reaction mixture by a separation technique that may include a standard or fluorous separation technique known to those skilled in the art. In the method where fluorous compound (IV) is to be used as a fluorous tagging reagent, for example fluorous benzyloximes, fluorous benzoyl chlorides, fluorous benzenesulfonyl chlorides, or fluorous phenols, then the tagged organic compound may be subjected to subsequent chemical transformations.

In addition, the method of the present invention may further include reducing the fluorous content of a second fluorous-tagged organic compound that is tagged with fluorous compound (IV). In this aspect of the invention, the first fluorous-tagged organic compound, in which the tag is from fluorous compound (IV), is subjected to at least one chemical reaction and potentially at least one purification process. The chemical reaction(s) produces the second fluorous-tagged organic compound, in which the tag is from fluorous compound (IV), which is isolated and subjected to the fluorous content reducing step. The resultant molecules may have uses that include, but are not limited to, pharmaceutical compounds or intermediates, and combinatorial library components.

The fluorous nature of the second fluorous-tagged organic compound may be reduced by removing at least one grouping of atoms having the possible structure: —C$_6$H$_{5-m}$—[W$_p$(CH$_2$)$_n$R$_f$]$_m$, —[W$_p$(CH$_2$)$_n$R$_f$]$_m$, —(CH$_2$)$_n$R$_f$ and R$_f$ from the second fluorous tagged organic compound.

In still a further embodiment, the present invention provides compounds for increasing the fluorous nature of an organic compound having the general structure of:

X—(CH$_2$)$_n$R$_f$     (V)

wherein R$_f$ is a fluorous group and n is an integer from 0 to 5. X may be a grouping of atoms having the substructure of —C(CH$_3$)$_2$COCl. The resultant compounds are fluorous pivaloyl chlorides. Fluorous pivaloyl chlorides have uses including, but not limited to, the tagging of alcohols and amines, and/or mixtures thereof. The fluorous tagged organic compound can then be separated from the reaction mixture by a separation technique that may include a standard or fluorous separation technique known to those skilled in the art. The tagged compound may then be subjected to subsequent chemical transformations.

Fluorous reagents such as (V), where component X is —C(CH$_3$)$_2$COCl, may be prepared by one of various schemes that employ a combination of organic techniques. For example, one possible scheme for the preparation of fluorous pivaloyl chlorides is disclosed in Scheme 29.

Scheme 29

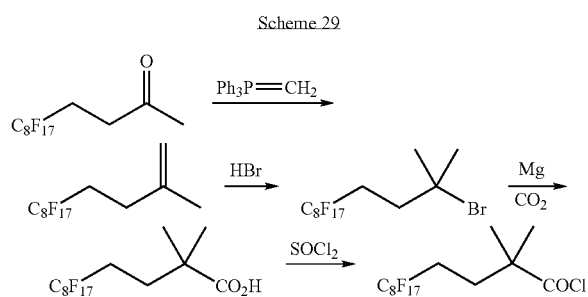

The present invention also provides a method for increasing the fluorous nature of an organic compound, including the step of reacting the organic compound with at least one second compound having the general structure of fluorous compound (V), as described above and also including where component X of fluorous compound (V) may be the group —$CR^{45}R^{46}SH$, —$CR^{45}R^{46}SR^{47}$, —$SO_2Cl$, —$OC(=O)NHNH_2$, —$NHC(=NH)NH_2$, —$SO_2NH_2$, —$SO_2NHNH_2$, —NCZ, -maleimide, -α-succinic anhydride, or —$COCH_2COR^{48}$. $R^{45}$, $R^{46}$, $R^{47}$, and $R^{48}$ are independently, the same or different, hydrogen, linear alkyl, branched alkyl, benzyl, or —$(CH_2)_nR_f$ and Z is either oxygen or sulfur. The organic compound has at least one functional group that reacts with group X on at least one second fluorous compound (V) to form at least one chemical bond between the organic compound and at least one second compound (V). The chemical reaction results in a first fluorous tagged organic compound with an increased fluorous nature relative to the fluorous nature of the organic compound. The increased fluorous nature of the first fluorous tagged organic compound enables separating the first fluorous tagged organic compound from other compounds by use of separation techniques that may include standard or fluorous separation techniques known to those of ordinary skill in the art. The tagged compound may then be subjected to subsequent chemical transformations.

The present invention may also provide a method for increasing the fluorous nature of an organic compound by reacting it with at least one second compound (V), where component X in fluorous compound (V) is —$CR^{45}R^{46}SH$ where the groups $R^{45}$ and $R^{46}$ are defined above. The resultant structures are fluorous alkylthiols. Fluorous alkylthiols have uses including, but not limited to, tagging/scavenging numerous electrophilic components, for example, aryl halides, bromomethylcarbonyl compounds, benzyl halides, allyl halides and other electrophiles, and/or mixtures thereof. They can also be used in the scavenging of metals such as Ni, Pd, and the like.

The present invention may also provide a method for increasing the fluorous nature of an organic compound by reacting it with at least one second compound (V), where component X in fluorous compound (V) is —$CR^{45}R^{46}SR^{47}$, where the groups $R^{45}$, $R^{46}$ and $R^{47}$ are defined above. The resultant compounds are fluorous alkyl sulfide reagents. Fluorous alkyl sulfide reagents have potential application including, but not limited to, scavenging oxidation agents and carbocations, for example, carbocations produced in peptide deprotection reactions.

The present invention may also provide a method for increasing the fluorous nature of an organic compound by reacting it with at least one second compound (V), where component X in fluorous compound (V) is —$SO_2Cl$. The resultant compounds are fluorous alkylsulfonyl chlorides that have uses including, but not limited to, tagging and scavenging alcohols, amines, thiols and other nucleophiles, and/or mixtures thereof.

The present invention may further provide a method for increasing the fluorous nature of an organic compound by reacting it with at least one second compound (V), where component X in fluorous compound (V) is —$OC(=O)NHNH_2$. The resultant compounds are fluorous alkylcarbazates that have uses including, but not limited to, tagging ketones.

The present invention may also provide a method for increasing the fluorous nature of an organic compound by reacting it with at least one second compound (V), where component X in fluorous compound (V) is —$NHC(=NH)NH_2$. The resultant compounds are fluorous alkylguanidines that have uses including, but not limited to, acting as strong organic bases which can scavenge acid.

The present invention may further provide a method for increasing the fluorous nature of an organic compound by reacting it with at least one second compound (V), where component X in fluorous compound (V) is —$SO_2NH_2$. The resultant structures are fluorous alkyl sulfonamides that have uses including, but not limited to, scavenging acids, acid chlorides, anhydrides, isocyanates, isothiocyanates, chloroformates and other electrophiles, and/or mixtures thereof.

The present invention may also provide a method for increasing the fluorous nature of an organic compound by reacting it with at least one second compound (V), where component X in fluorous compound (V) is —$SO_2NHNH_2$. The resultant structures are fluorous alkyl sulfonylhydrazides. Fluorous alkyl sulfonylhydrazides have uses including, but not limited to, scavenging aldehydes and ketones and/or mixtures thereof.

The present invention may further provide a method for increasing the fluorous nature of an organic compound by reacting it with at least one second compound (V), where component X in fluorous compound (V) is —NCZ, where Z is either oxygen or sulfur. The resultant compounds are fluorous alkyl isocyanates or fluorous alkyl isothiocyanates that have uses including, but not limited to, scavenging amines, hydrazines and other nucleophiles, and/or mixtures thereof.

The present invention may also provide a method for increasing the fluorous nature of an organic compound by reacting it with at least one second compound (V), where component X in fluorous compound (V) is -maleimide. The resultant compounds are fluorous maleimides that has the uses including, but not limited to, scavenging primary and secondary amines and thiols, and/or mixtures thereof.

The present invention may further provide a method for increasing the fluorous nature of an organic compound by reacting it with at least one second compound (V), where component X in fluorous compound (V) is -α-succinic anhydride. The resultant fluorous succinic anhydride has uses including, but not limited to, scavenging amines.

The present invention may also provide a method for increasing the fluorous nature of an organic compound by reacting it with at least one second compound (V), where component X in fluorous compound (V) is —$COCH_2COR^{48}$, wherein $R^{48}$ is defined above. The resultant fluorous alkyl-1,3-diketone has uses including, but not limited to, scavenging primary amines in the presence of secondary amines.

In the present method, when component X of fluorous compound (V) is as described above, the organic compounds that are reacted with fluorous compound (V) can be separated from the reaction mixture by a separation technique that may include a standard or fluorous separation technique known to those skilled in the art. In the method where fluorous compound (V) is to be used as a fluorous tagging reagent, for example fluorous pivaloyl chlorides, fluorous alkylthiols, fluorous alkylsulfonyl chlorides, or fluorous alkylcarbazates, then the tagged organic compound may be subjected to subsequent chemical transformations.

In addition, the method of the present invention may further include reducing the fluorous content of a second fluorous-tagged organic compound that is tagged with fluorous compound (V). In this aspect of the invention, the first fluorous-tagged organic compound, in which the tag is from fluorous compound (V), is subjected to at least one chemical reaction and potentially at least one purification process. The chemical reaction(s) produces the second fluorous-tagged organic compound, in which the tag is from fluorous compound (V), which is isolated and subjected to the fluorous content reducing step. The resultant molecules may have uses that include, but are not limited to, pharmaceutical compounds or intermediates, and combinatorial library components.

The fluorous nature of the second fluorous-tagged organic compound may be reduced by removing at least one grouping of atoms having the possible structure: $-C_6H_{5-m}-[W_p(CH_2)_nR_f]_m$, $-[W_p(CH_2)_nR_f]_m$, $-(CH_2)_nR_f$, and $R_f$ from the second fluorous tagged organic compound.

In still another embodiment, the present invention provides compounds for increasing the fluorous nature of an organic compound having the general structure of:

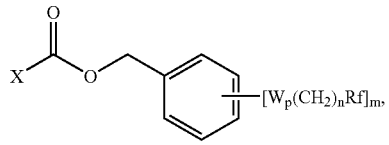
(VI)

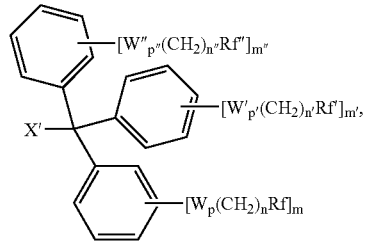
(VII)

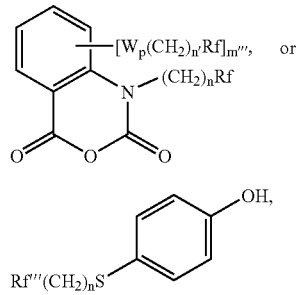
(VIII)

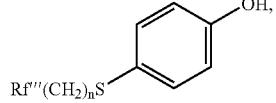
(IX)

wherein $R_f$, $R_f'$, and $R_f''$ are each fluorous groups, $R_f'''$ is a perfluoroalkyl group of 8 to 16 carbon atoms, X and X' are leaving groups, m is an integer from 1 to 5, m', m'', n, n', and n'' are each integers from 0 to 5, m''' is an integer from 0 to 4, and p, p', and p'' are each either 0 or 1. W, W' and W'' are each an atom or grouping atoms having the formula O, S, $NR^{49}$, $CR^{50}R^{51}$, or $SiR^{52}R^{53}$. $R^{49}$, $R^{50}$, and $R^{51}$ are independently, the same or different, either hydrogen, linear alkyl, branched alkyl, aryl, benzyl or $-(CH_2)_{n'''}R_f$. $R^{52}$ and $R^{53}$ are independently, the same or different, either hydrogen, linear alkyl, branched alkyl, aryl, benzyl or $-(CH_2)_{n'''}R_f$ and n''' is an integer from 0 to 5.

In the present invention, the leaving group X in structure (VI) may be various leaving groups suitable for use in the present invention and known to those skilled in the art. X may be a leaving group with a structure consisting of a halide, $-N_3$, $-CN$, $-OR^{30}$, $-ONH_2$, $-ONHR^{30}$, $-ONR^{30}_2$, $-O_2CR^{30}$, $-O_2COR^{30}$, $-O_2CNR^{30}_2$, $-SR^{30}$, $-OC(S)R^{30}$, $R^{30}CS_2-$, $-SC(O)SR^{30}$, $-SCS_2R^{30}$, $-OC(O)SR^{30}$, $-OC(S)OR^{30}$, $-SC(S)OR^{30}$, $R^{30}SO_2-$, $R^{30}SO_3-$, $R^{30}OSO_2-$, $R^{30}OSO_3-$, $R^{30}PO_3-$, $R^{30}OPO_3-$, an N-imidazolyl group, an N-triazolyl group, an N-benzotriazolyl group, a benzotriazolyloxy group, an imidazolyloxy group, an N-imidazolinone group, an N-imidazolone group, an N-imidazolinethione group, an N-succinimidyl group, an N-phthalimidyl group, an N-succinimidyloxy group, an N-phthalimidyloxy group, $-ON=C(CN)R^{30}$, or a 2-pyridyloxy group, wherein $R^{30}$ is one of linear alkyl, branched alkyl, aryl, benzyl, or $-(CH_2)_{n''}R_f$, wherein n'' in an integer from 0 to 5.

In the present invention, the leaving group X' in structure (VII) may be a leaving group that is a halide, methane sulfonate, p-toluenesulfonate, trifluoromethanesulfonate or perfluoroalkylsulfonate.

The present invention also provides a method for increasing the fluorous nature of an organic compound, including the step of reacting the organic compound with at least one second compound having the general structure of fluorous compound (VI), (VII), (VIII), or (IX) as described above, to create a first fluorous tagged organic compound. The organic compound having at least one functional group reactive with the functionality on the second fluorous compound (VI), (VII), (VIII), or (IX) forming at least one chemical bond between the organic compound and the second fluorous compound (VI), (VII), (VIII), or (IX) resulting in the first fluorous tagged organic compound. The fluorous nature of the first fluorous tagged organic compound is increased relative to the organic compound to enable separation of the first fluorous tagged organic compound from at least one other compound by using separation techniques that may include standard or fluorous separation techniques known to those of ordinary skill in the art.

In addition, the method of the present invention may further include reducing the fluorous content of a second fluorous-tagged organic compound that is tagged with fluorous compound (VI), (VII), (VIII), or (IX). In this aspect of the invention, the first fluorous-tagged organic compound, in which the tag is from fluorous compound (VI), (VII), (VIII), or (IX), is subjected to at least one chemical reaction and potentially at least one purification process. The chemical reaction(s) produces the second fluorous-tagged organic compound, in which the tag is from fluorous compound (VI), (VII), (VIII), or (IX), which is isolated and subjected to the fluorous content reducing step. The resultant molecules may have uses that include, but are not limited to, pharmaceutical compounds or intermediates, and combinatorial library components.

Fluorous Compounds and Their Use as Fluorous Tags

In the method of the present invention, the fluorous compounds described above may be used as fluorous tags to increase the fluorous nature of an organic compound. The tagged organic compound can then be subjected to subsequent chemical transformations and separations/purifications. Representative demonstrations of the fluorous tagging process is described below.

In one demonstration of its utility as a tag in fluorous synthesis, a fluorous thiol 1H,1H,2H,2H-perfluorodecanethiol was attached to the electron deficient 2,4-dichloro-6-methylpyrimidine by a nucleophilic substitution in the presence of diisopropylethylamine (DIPEA) (Scheme 30).

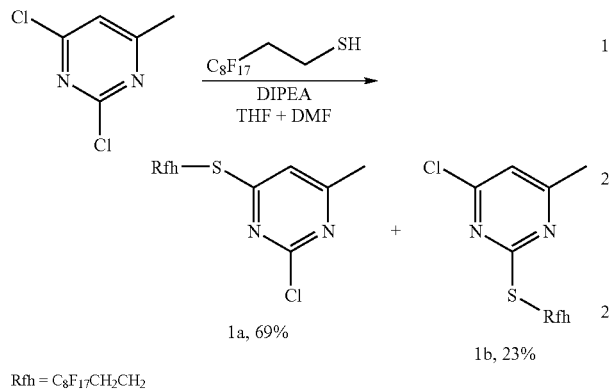

Two regioisomers 1a and 1b were generated in a ratio of 3:1 by HPLC analysis. If polymeric tags were used, regioisomers like 1a and 1b could not be separated. However, fluorous compounds 1a and 1b were readily separated by flash column chromatography on normal silica gel based on their different polarity. The major isomer 1a was used for further nucleophilic substitution with 3-(trifluoromethyl)-pyrazole to give 2 (Scheme 31). The fluorous sulfur tag was then activated by oxidation with Oxone® followed by the displacement with ten assorted nucleophiles including primary and secondary amines and thiols to yield disubstituted pyrimidines 4 (Table 1). Oxone® is commercially available from E. I. du Pont de Nemours and Company. Results were excellent: yields of 4a–j ranged from 74–96% and purities were usually above 90%.

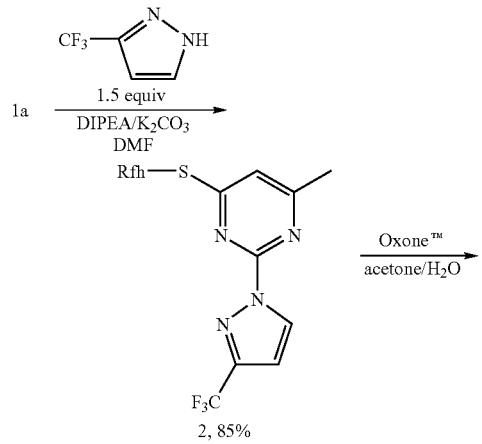

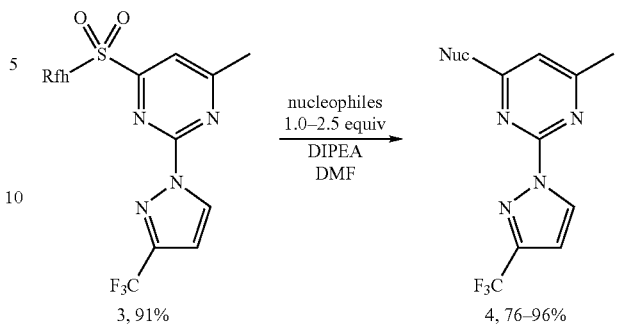

An important feature of fluorous synthesis is the employment of simple solid-phase extraction (SPE) over FluoroFlash® cartridges charged with fluorous silica that has a perfluorocarbon bonded-phase to selectively retain fluorous molecules while organic compounds pass through as fast as the solvent front. Only two fractions need to be collected from the SPE; a MeOH/H$_2$O (80/20) fraction containing non-fluorous compounds and a MeOH fraction containing fluorous compounds. The strong fluorine-fluorine interaction retains small molecules tagged with a light fluorous tag (C$_8$F$_{17}$) on fluorous silica gel until elution with a stronger solvent such as MeOH. Fluorous intermediate 2 was purified by SPE and collected from the MeOH fraction, while product 4 was collected from the MeOH/H$_2$O fraction. The DIPEA used for the reaction of 1a can be removed by acidic workup prior to SPE. The crude product containing cleaved tag, DIPEA, and excess nucleophile was purified by loading onto a FluoroFlash™ cartridge with a small amount of weak acidic ion exchange resin (Amberlite™ CG-50) on top of the fluorous silica and eluted with MeOH/H$_2$O (80/20).

TABLE 1

Structures, yields, and purities of disubstituted pyrimidinates 4a–j

| entry | nucleophile | equiv | product | yield (purity)[a] |
|---|---|---|---|---|
| 1 | morpholine | 2.5 | 4a | 96% (97%) |
| 2 | 1,2,3,4-tetrahydroisoquinoline | 2.0 | 4b | 91% (93%) |
| 3 | 1,4-dioxa-8-azaspiro[4.5]decane | 2.0 | 4c | 82% (92%) |
| 4 | 1-(2-pyridyl)piperazine | 2.5 | 4d | 93% (90%) |
| 5 | 1-phenylpiperazine | 2.5 | 4e | 79% (90%) |

TABLE 1-continued

Structures, yields, and purities of disubstituted pyrimidinates 4a–j

| entry | nucleophile | equiv | product | yield (purity)[a] |
|---|---|---|---|---|
| 6 | Me—C6H4—CH2—NH2 | 1.2 | 4f | 88% (89%) |
| 7 | 3-pyridyl-NH2 | 1.2 | 4g | 74% (93%) |
| 8 | pyrimidin-2-yl-SH | 1.0 | 4h | 76% (97%) |
| 9 | benzothiazol-2-yl-SH | 1.0 | 4i | 84% (92%) |
| 10 | 5-Me-1,3,4-thiadiazol-2-yl-SH | 1.0 | 4j | 77% (90%) |

[a]Purity was assesed by HPLC on a C18 column with a UV detector at 254 nm.

The cleaved tag was retained by the fluorous silica and amines were retained by the ionic exchange resin. It was found that $CF_3$ group of products 4 did not hold the molecules against elution with $MeOH/H_2O$. Most products had purities greater than 90% after SPE. The crude intermediate 2 was separated from the excess 3-(trifluoromethyl)pyrazole by collecting the MeOH fraction. The crude product 4e containing excess 4-phenylpiperazine, DIPEA, and cleaved fluorous tag was purified by collecting the $MeOH/H_2O$ fraction from a cartridge charged with fluorous silica and acidic ion exchange resin.

Synthesis of substituted pyrimidines exemplifies the unique characters of fluorous synthesis, including the use of tag strategy for quick SPE, analysis and separation of tagged-isomers by conventional tools, and adaptability of traditional solution-phase reaction conditions. The "beadless" and traceless fluorous thiol tag is complementary to corresponding thiol linkers in solid-phase synthesis. The "catch and release" method with the fluorous thiol can be applied to the synthesis of other substituted N-heterocycles.

In another example of the method of the present invention, wherein the fluorous compounds may be used as an alternative to a polymer resin to prepare libraries of organic compounds. Below is an example demonstrating the utility of a perfluoroalkylsulfanylphenol as a fluorous tag.

Described in this paper is the synthesis of fluorous version of Marshall resin, perfluoroalkylsulfanylphenol 5 (FluoMar™). FluoMar is now commercially available from Fluorous Technologies Inc. (Pittsburgh, Pa.). The utility of this compound is illustrated by the solution-phase synthesis of amides and diamides.

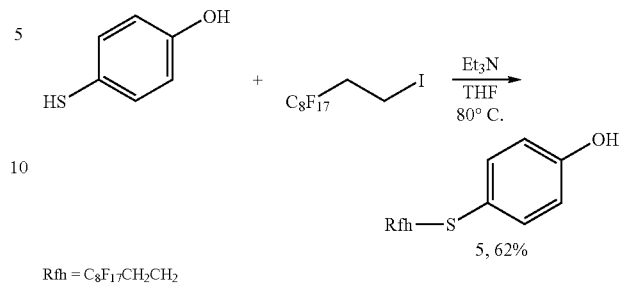

Scheme 32

Rfh = $C_8F_{17}CH_2CH_2$

The FluoMar™ 5 was readily prepared by S-alkylation of 4-mercaptophenol with $C_8F_{17}CH_2CH_2I$ and purified by flash column chromatography on normal silica gel (Scheme 32). The ethylene spacer between the $C_8F_{17}$ tag and the sulfur is expected to minimize the strong electron-withdrawing effect from the perfluoroalkyl group and maintain the nucleophilicity of the hydroxy group. This compound has the general features of organic molecules; it dissolves well in common solvents such as $CH_2Cl_2$, THF, and AcOEt, and can be analyzed by traditional chromatographic and spectroscopic methods.

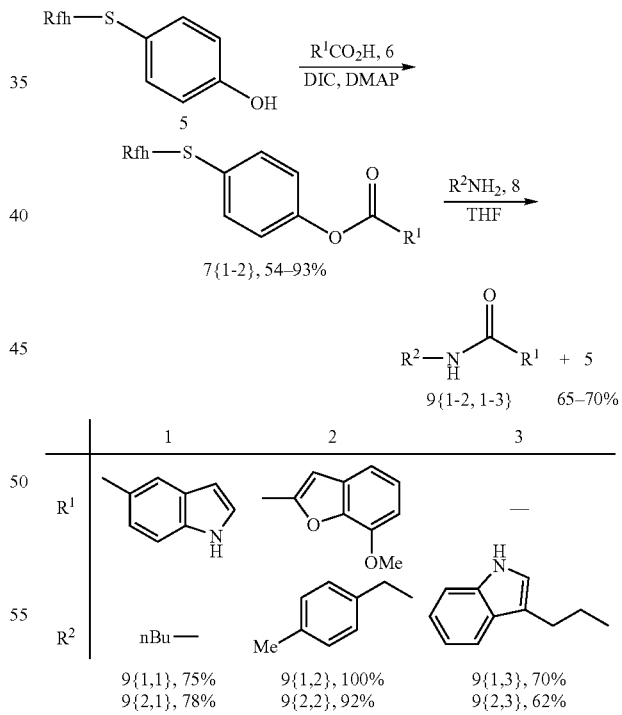

Scheme 33

With compound 5 in hand, we first validated the attachment to carboxylic acids 6 and the tag cleavage by the amine displacement (Scheme 33). The coupling of 5 with indole-5-carboxylic acid 6{1} (2.0 equiv) or 7-methoxy-2-benzofurancarboxylic acid 6{2} was carried out under a standard solution-phase conditions with 2.0 equiv of diisopropylcarbodiimide (DIC) and 1.0 equiv of dimethylaminopyridine (DMAP) in DMF. These intermediates were purified by regular flash column chromatography. Compounds 7{1} and 7{2} were each split to three portions and directly displaced with three primary amines 8{1–3} without oxidation of the sulfur to give the corresponding amides 9{1–2,1–3}. After a quick acidic workup with 1.0 N HCl to remove the unreacted amine, the crude product was loaded onto a FluoroFlash™ cartridge and the MeOH/H$_2$O fraction was collected to give analytically pure product. The FluoMar™ tag 5 was recovered in the MeOH fraction in 65–70% yield.

Encouraged by the preliminary results, the use of FluoMar™ 5 in a multi-step parallel synthesis of diamides was explored (Scheme 34). The N-Boc isonipecotic acid 10 was coupled with 5 followed by deprotection with TFA and N-acylation with three different acid halides. The resulting compounds 12{1–3} were each split into three portions and displaced by three amines resulting in a demonstration library of diamides 13{1–3,1–3}. The final products were purified by SPE and cleaved FluoMar™ 5 was recovered in an average yield of 65%.

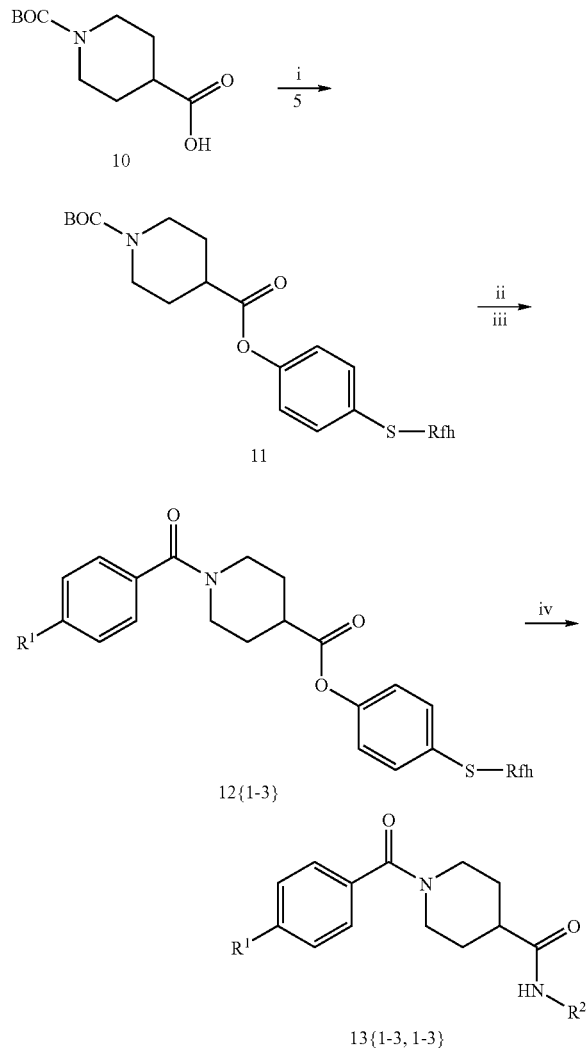

Scheme 34

| | 1 | 2 | 3 |
|---|---|---|---|
| R$^1$ | Cl | H | OMe |
| R$^2$ | nBu— | Me-C$_6$H$_4$-CH$_2$CH$_2$— | indol-3-yl-propyl |
| | 13{1,1}, 93% | 13{2,1}, 90% | 13{3,1}, 90% |
| | 13{1,2}, 100% | 13{2,2}, 95% | 13{3,2}, 100% |
| | 13{1,3}, 37% | 13{2,3}, 21% | 13{3,3}, 55% | i. 1.0 equiv of 5, 2.0 equiv of 10, 2.0 equiv DIC, 1.0 equiv DMAP, DMF, 25° C., 8 h, SPE, 71%.
ii. 9.0 eq. TFA, CH$_2$Cl$_2$, 8 h, SPE, 100%.
iii. 1.5 equiv R$^1$PhCO$_2$Cl, 1.5 equiv Et$_3$N, THF, 55° C., SPE, 73–78%.
iv. 1.5 equiv R$^2$NH$_2$, THF, 60° C., 5 h, SPE, 21–100%

Fluorous Compounds and Their Use as Fluorous Scavengers

In a further example of the method of the present invention, wherein the fluorous compounds described above may be used react with unreacted reaction components, thereby tagging the unreacted component. The tagged unreacted reaction component can then be readily removed or scavenged from the reaction mixture by a separation technique that may include a standard or fluorous separation technique known to those skilled in the art. A representative demonstration of the fluorous scavenging process is described below.

Introduced herebelow are two new fluorous electrophilic scavengers, isatoic anhydride 14 and isocyanate 15, that can be used to remove primary and secondary amines from the reaction mixtures.

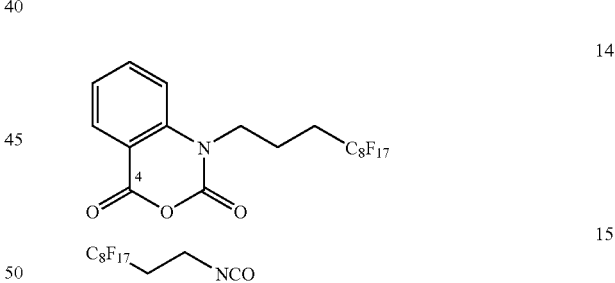

Compound 15 was readily prepared by N-alkylation of isatoic anhydride with C$_8$F$_{17}$CH$_2$CH$_2$CH$_2$I using sodium hydride as a deprotonation agent. The C-4 carbonyl is an active site for the nucleophilic attack. Fluorous isocyanate 15 was synthesized following a literature procedure. To demonstrate the utility of these two compounds as scavengers for amines, two substrates, phenyl isocyanate and phenyl isothiocyanate were reacted with various primary and secondary amines to produce corresponding ureas and thioureas (Scheme 35). In each case, 1.5 equiv of amine was used to ensure the consumption of the substrate.

Scheme 35

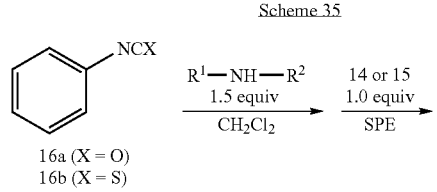

16a (X = O)
16b (X = S)

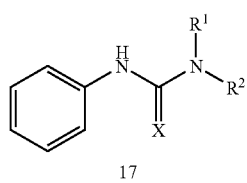

17

Upon completion of the reaction (as monitored by TLC or HPLC), 1.0 equiv of fluorous scavenger was added to react with the excess amine. The reaction mixture was then loaded onto a FluoroFlash® cartridge charged with fluorous silica. The cartridge was eluted with MeOH-$H_2O$ (80:20) to collect the product fraction and then with 100% MeOH to wash off the fluorous scavenged product and the unreacted scavenger. Results listed in Table 2 demonstrate that the product purity is greater than 95% after the scavenging. Use of fluorous isatoic anhydride 14 as scavenger usually give better yields (75–100%) than that of isocyanate 15 (34–100%).

Fluorous isatoic anhydride 14 was further evaluated in the reaction of epoxide 18 with amines (Scheme 36). In a high loading experiment using 2.0 equiv of amine and 3.0 equiv of scavenger 14, products 19a (42%) and 19b (67%) from primary amines had better yields than products 19d (15%) and 19e (29%) from secondary amines. It was hypothesized that the low yield might have been caused by the interaction of excess scavenger with the β-hydroxyamine product.

TABLE 2

Structures, yields, and purities of ureas and thioureas[a]

| substrate | amine | scavenger | product | X | yield | purity[b] |
|---|---|---|---|---|---|---|
| 16a | butylamine | 14 | | O | 100% | >95% |
| 16b | | 14 | | S | 75% | 95% |
| 16a | | 15 | | O | 52% | 95% |
| 16b | | 15 | | S | 98% | 95% |
| 16a | 4-methylbenzylamine | 14 | | O | 100% | >95% |
| 16b | | 14 | | S | 72% | >95% |
| 16a | | 15 | | O | 100% | >95% |
| 16b | | 15 | | S | 80% | >95% |
| 16a | tryptamine | 14 | | O | 100% | >95% |
| 16b | | 14 | | S | 95% | >95% |
| 16a | | 15 | | O | 100% | 95% |
| 16b | | 15 | | S | 34% | 95% |
| 16a | 1-(2-pyridyl)piperazine | 14 | | O | 100% | >95% |
| 16b | | 14 | | S | 100% | 95% |
| 16a | | 15 | | O | 100% | 95% |
| 16b | | 15 | | S | 68% | >95% |
| 16a | tetrahydroisoquinoline | 14 | | O | 100% | >95% |
| 16b | | 14 | | S | 100% | 95% |
| 16a | | 15 | | O | 100% | 95% |
| 16b | | 15 | | S | 96% | 95% |

[a]conditions: 1.0 equiv of substrate and 1.5 equiv of amine, $CH_2Cl_2$, 60° C., 6–12 h in a capped vial, then quenched with 1.0 equiv of a scavenger, 60° C., 2.5 h.
[b]purity was assessed by $^1H$ NMR.

To test this hypothesis, reactions with lower input of the secondary amine (1.5 equiv) and scavenger (0.7 equiv) were performed. Significant yield improvement was observed for 19d (62%) and 19e (58%) (Table 3). However, under both reaction conditions, no clean desired product 19c was isolated. It was contaminated with the di-N-alkylation product. All other cases listed in Table 3, the product yields may vary in a broad range under different reaction conditions, the purities were consistently between 90–95%.

-continued

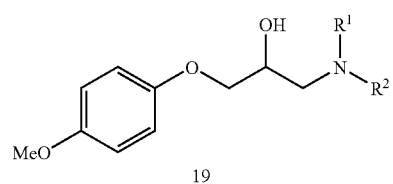
19

Scheme 36

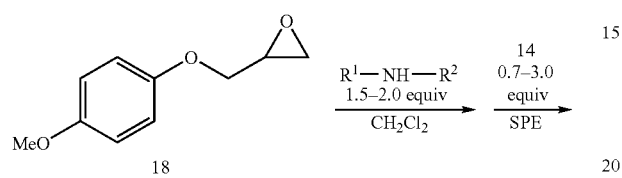

TABLE 3

Structures, yields, and purities of β-hydroxyamines[a]

| amine | (equiv) | scavenger 14 (equiv) | product | yield | purity[b] |
|---|---|---|---|---|---|
| ~~~NH₂ (butylamine) | 2.0 | 3.0 | 19a | 42% | 95% |
| 4-methylbenzylamine | 2.0 | 3.0 | 19b | 67% | 95% |
| tryptamine | 2.0 / 1.5 | 3.0 / 0.7 | 19c | 0% / 0% | — / — |
| 1-(2-pyridyl)piperazine | 2.0 / 1.5 | 3.0 / 0.7 | 19d | 15% / 62% | >95% / >95% |

TABLE 3-continued

Structures, yields, and purities of β-hydroxyamines[a]

| amine | (equiv) | scavenger 14 (equiv) | product | yield | purity[b] |
|---|---|---|---|---|---|
| 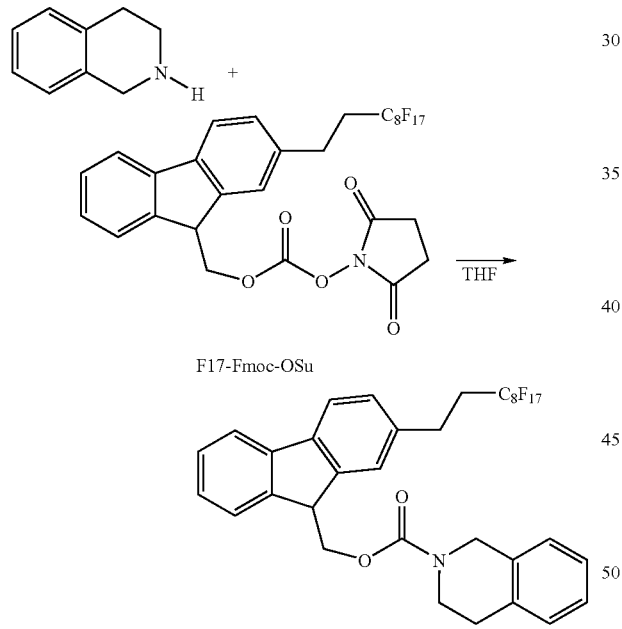 | 2.0 1.5 | 3.0 0.7 | 19e | 29% 58% | 90% 90% |

[a]condition: 18 and amine in $CH_2Cl_2$, 60° C., 6–12 h in a capped vial, then quenched with 14, 60° C., 2.5 h.
[b]purity was assessed by $^1H$ NMR.

Fluorous Compounds and Their Use as a Protecting Group: Tagging and Detagging of an Organic Compound The method of the present invention can further be demonstrated by the use of a fluorous compound as a protecting group for an organic functional group. The tagging (protection) and detagging (deprotection) of an organic compound is demonstrated below using an F-Fmoc tag.

Protection of Amine with of F17-Fmoc.

Deprotection of F17-Fmoc Group.

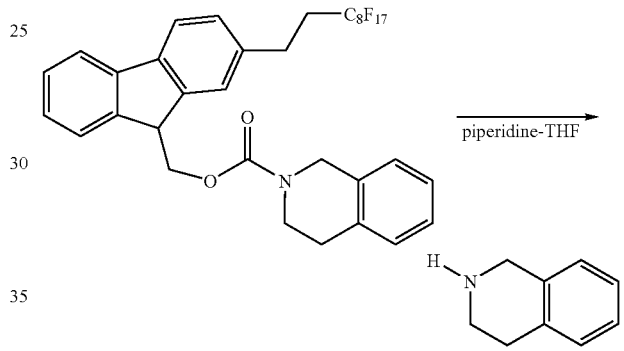

Deprotection of F17-Fmoc protected amine was performed according to standard conditions. (Morpholine-THF, 1:4). Reaction time is typically within 15 min at 23° C., affording 1,2,3,4-tetrahydroisoquinoline.

The present invention will be described further by reference to the following examples. The following examples are merely illustrative of the invention and are not intended to be limiting. Unless otherwise indicated, all parts are by weight.

EXAMPLES

Example I

N-[2-(1H,1H,2H,2H-Perfluorodecyl)fluorenyl-9-methoxycarbonyloxy]-1,2,3,4-tetrahydroquinoline: To a solution of N-[2-(1H,1H,2H,2H-Perfluorodecyl)fluorenyl-9-methoxycarbonyloxy]succinimide (F17-Fmoc-OSu) (78.3 mg, 0.1 mmol) in THF was added 1,2,3,4-tetrahydroisoquinoline (15.0 mg, 0.12 mmol) at 23° C. After 10 min, the solvent was removed under reduced pressure, and the residue was dissolve in THF (1 mL). The solution was loaded onto a FluoroFlash® SPE cartridge (5 g), and it was eluted with MeOH-H2O (80:20, 15 mL), and then with MeOH (20 mL). The methanol fraction was collected, and the solvent was removed under reduced pressure to give the title compound as white solid (69.4 mg, 84% yield). $^1H$ NMR (270 MHz, $CDCl_3$) δ 7.90–7.02 (11H, m), 7.64 (2H, d, J=13 Hz), 4.50 (2H, d, J=12 Hz), 4.27 (1H, t, J=7 Hz), 3.72 (2H, bd), 2.98 (2H, bs), 2.86 (2H, bs), 2.55–2.25 (2H, m); MS APCI positive, m/z=802 $[m^+H]^+$.

Preparation of N-[4-(1H,1H,2H,2H-perfluorodecyl)benzyloxycarbonyloxy]succinimide

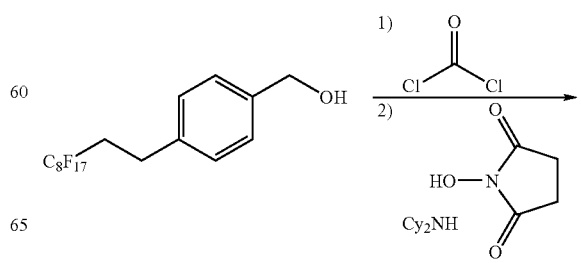

-continued

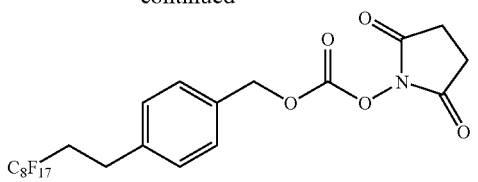

Under dry N$_2$ atmosphere at 0° C., phosgene (21.5 mL; 20% in toluene) was charged to a 250 mL 3-neck flask equipped with thermometer, N$_2$ gas inlet, and addition funnel. A solution of 4-(1H,1H,2H,2H-perfluorodecyl)benzyl alcohol (15.0 g) in anhydrous THF (75 mL) was added dropwise, keeping the temperature between 0–5° C. The mixture was stirred at 0–5° C. until the reaction was complete. The solvent and excess phosgene were removed in under vacuum and the product was dissolved in chloroform (200 mL). N-hydroxysuccinimide dicyclohexylamine salt (8.81 g) was added portionwise over 5–10 minutes. After the reaction was complete, water (100 mL) and 1 N HCl (100 mL) were added, and the product was extracted with chloroform (3×100 mL). The organic layers were dried over MgSO$_4$, filtered and concentrated. The crude product was recrystallized in hot methanol (900 mL). The solid was collected by filtration and dried under high vacuum for 5 h to give desired product (15.4 g, 82% yield). The structure of the product was characterized $^1$H NMR.

Example II

Preparation 4-[3-(perfluorooctyl)propyloxy]benzaldehyde

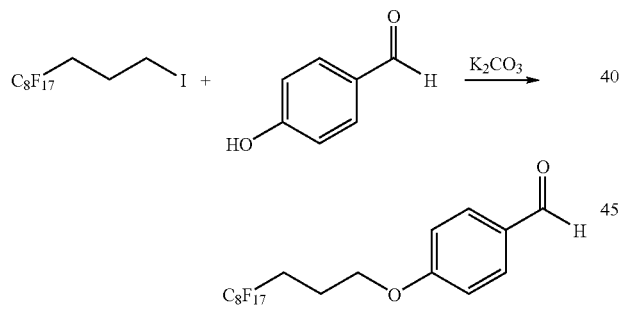

A 500 mL 2-neck flask equipped with thermometer and gas inlet charged with potassium carbonate (27.6 g), hydroxy benzaldehyde (13.4 g), and 3-(perfluorooctyl)propyl iodide (58.8 g) in DMF (200 mL) was heated to 65° C. (internal temperature). The mixture was stirred at 65° C. until the reaction was complete. The reaction mixture was cooled to room temperature. Water (300 mL) and ether (300 mL) were added and the mixture stirred vigorously for 5 min. The layers were separated and the organic layer retained. The aqueous layer was extracted with ether (3×200 mL). The combined organic layers were washed with water (2×100 mL), Na$_2$S$_2$O$_3$ (1×100 mL), 2.5 N NaOH (3×100 mL), and aqueous NaCl (1×100 mL). The organic layer was dried over MgSO$_4$, filtered and concentrated. The product was further dried under high vacuum for 5 h to give desired product (53 g, 91% yield). The structure of the product was characterized $^1$H NMR.

Example III

Preparation of Fluorous Fmoc-OSu

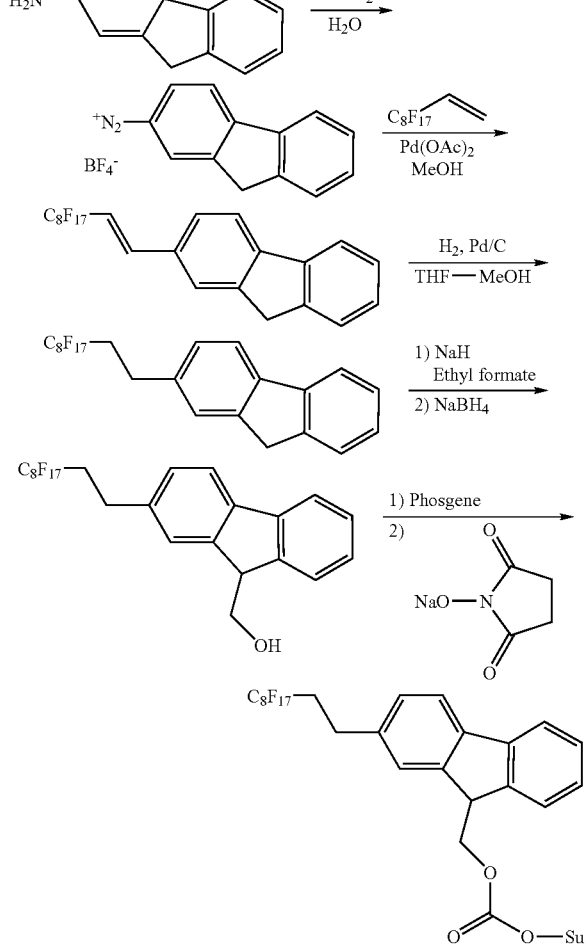

To a suspension of 2-aminofluorene (10.3 g) in fluoroboric acid (50% in water, 100 mL) was slowly added a solution of NaNO$_2$ (4.4 g) in water (15 mL) at below 10° C. The mixture was stirred for 6 h at below 10° C. The precipitate was collected by filtration, and was washed with ice-cooled water (3×), and was dried under air for 12 h to give yellow-green-brownish powder (17.0 g) that was used for the next step without purification.

To a suspension of crude fluorene-2-diazonium tetrafluoroborate (17.0 g) in MeOH (100 mL) was added Pd(OAc)$_2$ (0.14 g, 0.62 mmol) under an nitrogen atmosphere. The mixture was warmed to 30° C. (internal temperature), and then 1H,1H,2H-perfluorodec-1-ene (32.0 g) was added dropwise to keep the temperature below 45° C. The mixture was stirred at 45° C. for 2 h, and then it was refluxed for 1 h. After cooling to room temperature, Et$_2$O (200 mL) and H$_2$O (200 mL) were added. After the separation, the aqueous layer was extracted with Et$_2$O (2×100 mL). The ether layers were combined, and were washed with 1 N HCl (2×), water (2×), and brine (1×). The mixture was dried over MgSO$_4$. After filtration, it was treated with charcoal (2 scoops). The charcoal was filtered off by passing though a Celite® pad.

Celite® is commercially available from World Minerals Inc. (Lompoc, Calif.). After the removal of the solvent, light orange powder was obtained (31.5 g, 91% yield based on 2-aminofluorene).

Under an nitrogen atmosphere, Pd/C (10 wt % on active carbon, 1.0 g, loading=2 mol %) was added to a solution of 2-(1H,2H-perfluorodec-1-enyl)fluorine (31.5 g, 51.6 mmol) in THF (600 mL) and MeOH (100 mL). The mixture was stirred under a hydrogen (1 atm) for 1 day at 23° C. The catalyst was removed by filtration through a pad of Celite® under a nitrogen atmosphere, and the Celite® was rinsed with THF (4×50 mL). The filtrate was concentrated to give white powder (30.0 g, 95% yield).

To a suspension of NaH (60 wt % in mineral oil, 2.3 g) in Et$_2$O (200 mL) was added 2-(1H,1H,2H,2H-perfluorodecyl) fluorene (7.4 g) and ethyl form ate (19.0 mL) under an nitrogen atmosphere. The mixture was refluxed for 3 h, and then cooled on ice-water bath. Aquous HCl (1 N, 200 mL) was slowly added, and the two layers were separated. The aquous layer was extracted with Et$_2$O (1×50 mL). The ether layers were combined, and were washed with brine (2×). After being dried over MgSO$_4$, the solvent was removed to give yellow solid. The solid was dissolved in THF-MeOH (1:1, 200 mL), and NaBH$_4$ (1.2 g) was added in small portions over the period of 1.5 h at 6° C. After 2 h, aqueous HCl (1 N, 200 mL) and Et$_2$O (100 mL) were added. The aqueous layer was extracted with Et$_2$O (1×100 mL). The ether layers were combined, and were washed with 1 N HCl (1×) and brine (1×). After being dried over MgSO$_4$, the solvent was removed under reduced pressure. The product was purified by flash chromatography (SiO$_2$, eluent: hexanes/EtOAc=9:1–4:1) to give the title compound (6.2 g, 81% yield).

Phosgene (20 wt % solution in toluene, 2.3 mL, 4 mmol) was added to a solution of 9-[2-(1H,1H,2H,2H-perfluorodecyl)fluorenyl]methanol (1.3 g) in THF (60 mL) at 8° C. The mixture was stirred at 23° C. for 15 h, and the solvent was removed under reduced pressure to form pale yellow solid. The solid was dissolved in THF (30 mL), and NaOSu (0.54 g) was added in two portions over the period of 2 h. The mixture was vigorously stirred for 1 d at 23° C. Et$_2$O (50 mL) was added, and the mixture was filtered through a pad of Celite®. The Celite® pad was rinsed with Et$_2$O (3×10 mL). The filtrates were combined, and the solvent was removed under reduced pressure to give the product as white powder (1.5 g, 95% yield). 1H NMR (270 MHz, CDCl$_3$) δ 7.75 (2H, t, J=8.3 Hz), 7.62 (1H, d, J=7.4 Hz), 7.5 (1H, s), 7.44 (1H, t, J=7.5 Hz), 7.39–7.27 (2H, m), 4.67–4.50 (2H, m), 4.34 (1H, t, J=7.4 Hz), 3.10–2.95 (2H, m), 2.85 (s, 4H), 2.55–2.32 (2H, m); MS APCI negative, m/z=782 [m–H]–, 654, 641, 611.

Example IV

Preparation of p-(1H,1H,2H,2H-perfluorodecanesulfanyl) phenol.

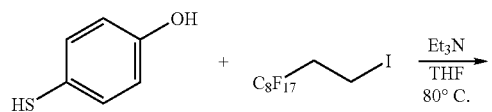

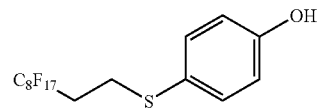

To a solution of 4-mercaptophenol (5.05 g) in THF (60 ml) was added Et$_3$N (11.1 mL) and 1H,1H,2H,2H-perfluorodecaneiodide (23.8 g). The reaction mixture was heated at 80° C. for 8 h. The reaction mixture was then poured into ice water. The precipitate was filtered off, washed with hexanes and dried under vacuum to provide the desired product 1 as a white solid (18.0 g, 78% yield), mp 85–87° C. $^1$H NMR (300 MHz, CDCl$_3$) δ 7.38 (d, J=8.8 Hz, 2H), 6.86 (d, J=8.8 Hz, 2H), 5.0 (br s, 1H), 3.06–3.00 (m, 2H), 2.56–2.39 (m, 2H). LC-MS (EI) m/z (rel. intensity) 572 (M$^+$), 553 (X), 169 (V), 139 (70), 125 (100), 97 (23), 81 (20), 69 (45), 58 (55). HRMS calc'd for C$_{16}$H$_9$OF$_{17}$S 572.0093; found 572.0093.

Fluorous Synthesis Using p-(1H,1H,2H,2H-perfluorodecanesulfanyl)phenol as a Tag.

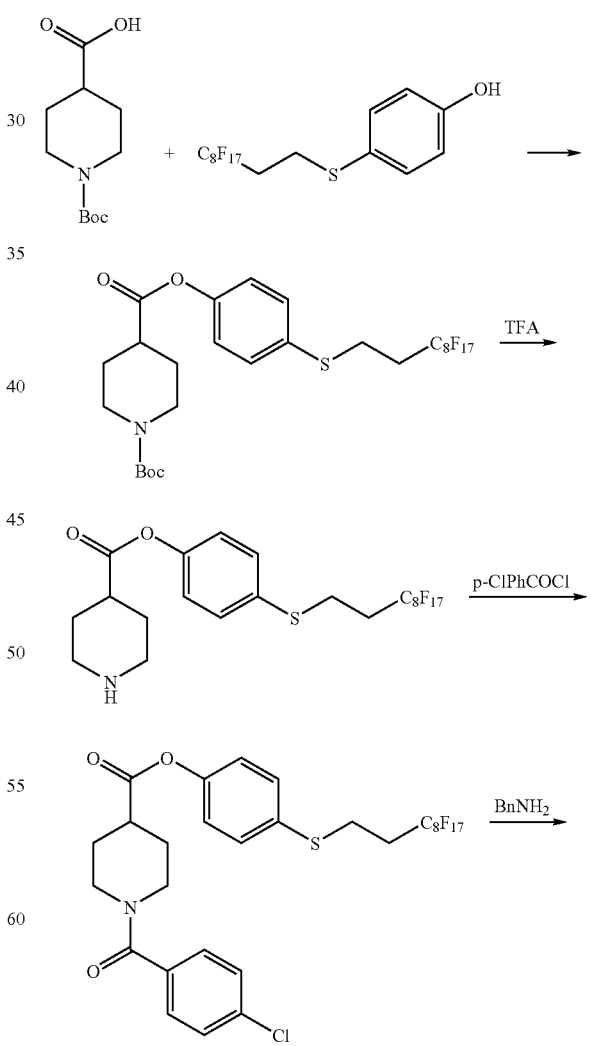

-continued

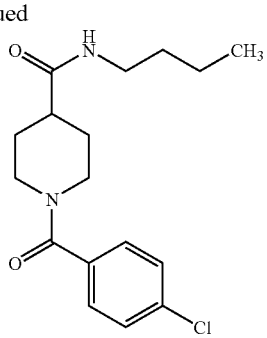

To a mixture of p-(1H,1H,2H,2H-perfluorodecanesulfanyl)phenol (2.2 g), N-Boc isonipecotic acid (1.76 g) in DMF (6 mL) was dissolved dimethylaminopyridine (DMAP) (0.05 g) and N,N'-diisopropylcarbodiimide (DIC) (1.2 ml). After stirring at room temperature for 1.5 h, the reaction mixture was poured into water and extracted with EtOAc. The organic layers was washed with brine, dried over $MgSO_4$, and filtered. The concentrated crude product was purified by flash column chromatography with EtOAc/hexanes (15/85) to give the fluorous bound N-Boc isonipecotic ester (2.13 g, 71% yield), mp 94–95° C. $^1$H NMR (300 MHz, $CDCl_3$) δ 7.39 (d, J=8.6 Hz, 2H), 7.07 (d, J=8.6 Hz, 2H), 4.13–4.06 (m, 2H)), 3.13–3.07 (m, 2H), 2.97–2.88 (m, 2H), 2.76–2.69 (m, 1H), 2.42–2.37 (m, 2H), 2.07–2.01 (m, 2H), 1.84–1.71 (m, 2H), 1.47 (s, 9H). LC-MS (EI) m/z (rel. intensity) 783 (M$^+$), 764 (VIII), 710 (35), 682 (40), 572 (60), 212 (50), 156 (100), 112 (32), 77 (IX). HRMS calc'd for $C_{27}H_{26}O_4F_{17}SN$ 783.1286; found 783.1286.

To a solution of fluorous bound N-Boc isonipecotic ester (7.22 g) in $CH_2Cl_2$ (15 mL) was added TFA (6.5 mL) in 2 portions of 3.25 ml in interval of 4 h. After 10 h, the reaction mixture was poured onto ice water (100 mL), aquous $NaHCO_3$ (200 mL) was added and the mixture was stirred for 20 min. The white precipitate was filtered, washed with water and dried under vacuum. Quantitative yield of fluorous bound isonipecotic ester was obtained (6.3 g, 100% yield), mp 147–148° C. This compound was used for next step without further purification. $^1$H NMR (300 MHz, $CD_3OD$) δ 7.47 (d, J=8.8 Hz, 2H), 7.13 (d, J=8.8 Hz, 2H), 3.48–3.41 (m, 2H), 3.31–3.29 (m, 1H), 3.19–3.16 (m, 4H); 3.10–2.98 (m, 1H); 2.54–2.27 (m, 4H); 2.07–1.93 (m, 2H). LC-MS (EI) m/z (rel. intensity) 682 (M$^+$, 25), 664 (30), 572 (22), 139 (VII), 112 (100), 84 (30). HRMS calc'd for $C_{24}H_{18}O_2F_{17}SN$ 682.0722; found 682.0722.

To a solution of fluorous bound isonipecotic ester (2.0 g) in THF (10 mL) was added $Et_3N$ (1.2 mL) followed by 4-chlorobenzoyl chloride (617 μL). The mixture was heated at 50–60° C. for 2.5 h. The reaction mixture was poured onto 1N HCl aq and extracted with EtOAc. The organic layer was washed with brine, dried over $MgSO_4$, and filtered. The concentrated crude product was purified by column chromatography with EtOAc/hexanes (30/70) to provide fluorous bound N-acylated isonipecotic ester 5 (1.9 g, 79%), mp 92–94° C. $^1$H NMR (300 MHz, acetone d-$_6$) δ 7.50 (d, J=8.5 Hz, 2H), 7.47 (s, 4H), 7.16 (d, J=8.5 Hz, 2H), 3.27–3.21 (m, 2H), 3.15 (br s, 1H), 3.02–2.93 (m, 1H), 2.62–2.47 (m, 2H); 1.85–1.73 (m, 2H). LC-MS (EI) m/z (rel. intensity) 821 (M$^+$, 33), 802 (16), 682 (15), 572 (25), 250 (35), 222 (15), 156 (16), 139 (85), 121 (100), 69 (23). HRMS calc'd for $C_{29}F_{17}H_{21}NSO_3Cl$ 821.0635, found 821.0635.

To a solution of fluorous N-acylated isonipecotic ester (0.11 g) in THF (1.0 mL) was added N-butylamine (0.02 mL). The mixture was heated at 50–60° C. for 5 h. The reaction mixture was poured onto 1N aq HCl and extracted with EtOAc in a small vial. The organic layer was washed with brine, dried over $MgSO_4$, and filtered. The concentrated oily residue (119 mg) was purified by solid-phase extraction on a 5 g FluoroFlash® fluorous silica gel cartridge eluted with $MeOH/H_2O$ (80/20). The first fraction (8 mL) contained the desired product was concentrated to give product (40 mg, 93%). $^1$H NMR (300 MHz, $CDCl_3$) δ 7.47 (d, J=8.7 Hz, 2H), 7.39 (d, J=8.7 Hz, 2H), 4.6 (br s, 1H), 3.70 (br s, 1H), 3.31–3.29 (m, 1H), 3.16 (t, J=6.8 Hz, 2H); 2.90 (t, J=7.3 Hz, 1H); 2.54–2.44 (m, 1H); 1.84 (br s, 2H), 1.67–1.60 (m, 2H), 1.50–1.28 (m, 4H), 0.99–0.89 (m, 4H). LC-MS (EI) m/z (rel. intensity) 322 (M$^+$, 30), 222 (22), 183 (63), 139 (100), 128 (95), 111 (51), 82 (51), 57 (25). HRMS calc'd for $C_{17}H_{23}N_2O_2Cl$ 322.1463, found 322.1463.

Following the general procedure described above. A 9-compound demonstration library was synthesized by reacting of N-Boc isonipecotic acid with 3 benzoyl chlorides and 3 amines (Table 4).

TABLE 4

Synthesis of isonipecotic acid derivatives

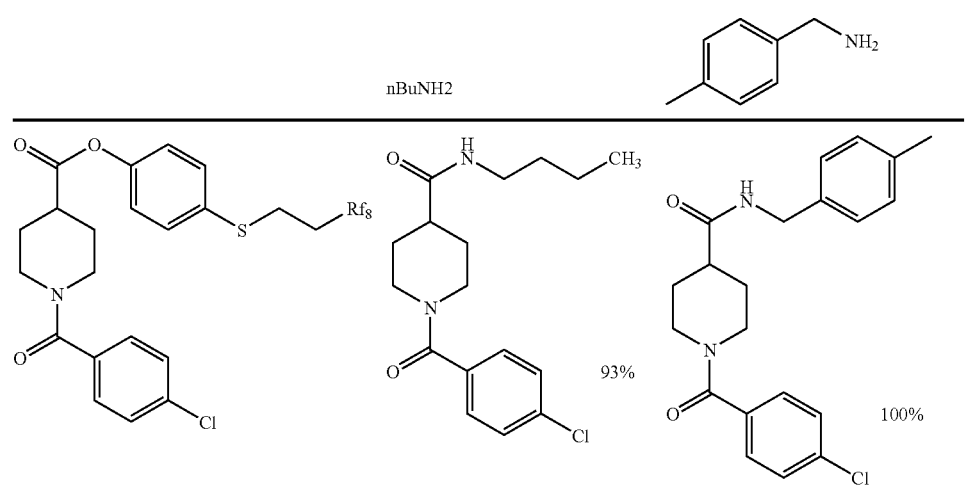

TABLE 4-continued
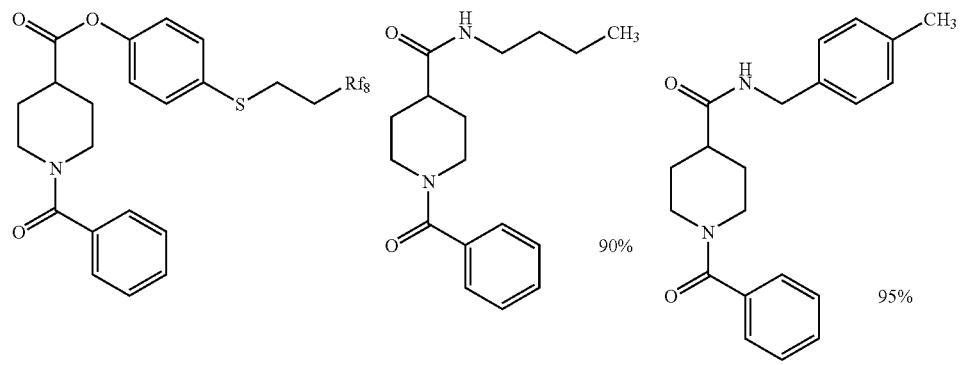
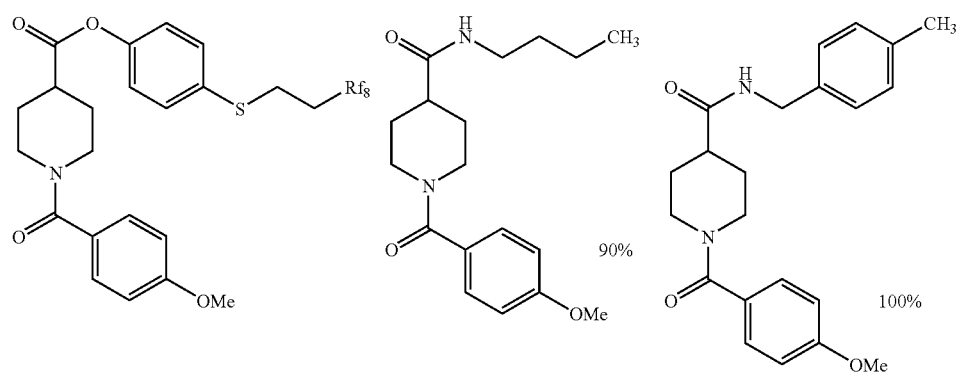
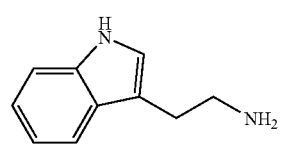
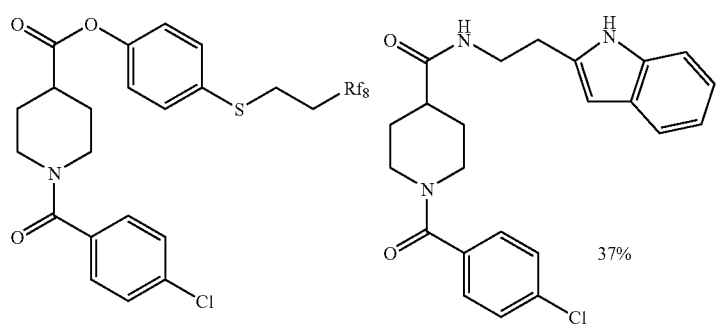
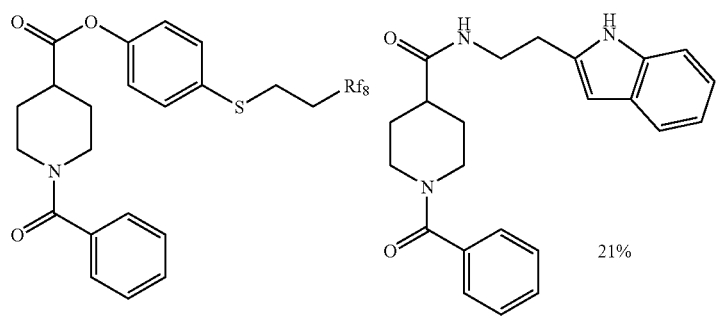

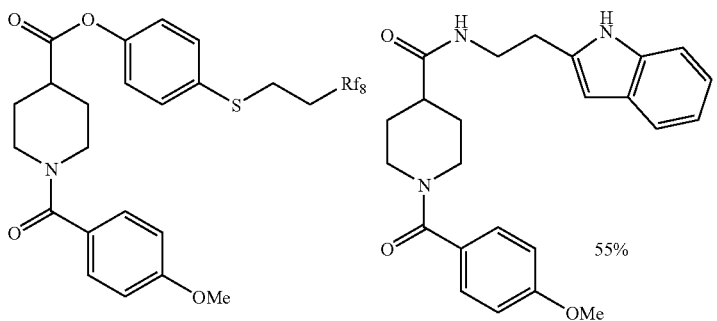

Example V

Fluorous Synthesis of Disubstituted Pyrimidines Using 1H,1H,2H,2H-perfluorodecanethiol as the Tag

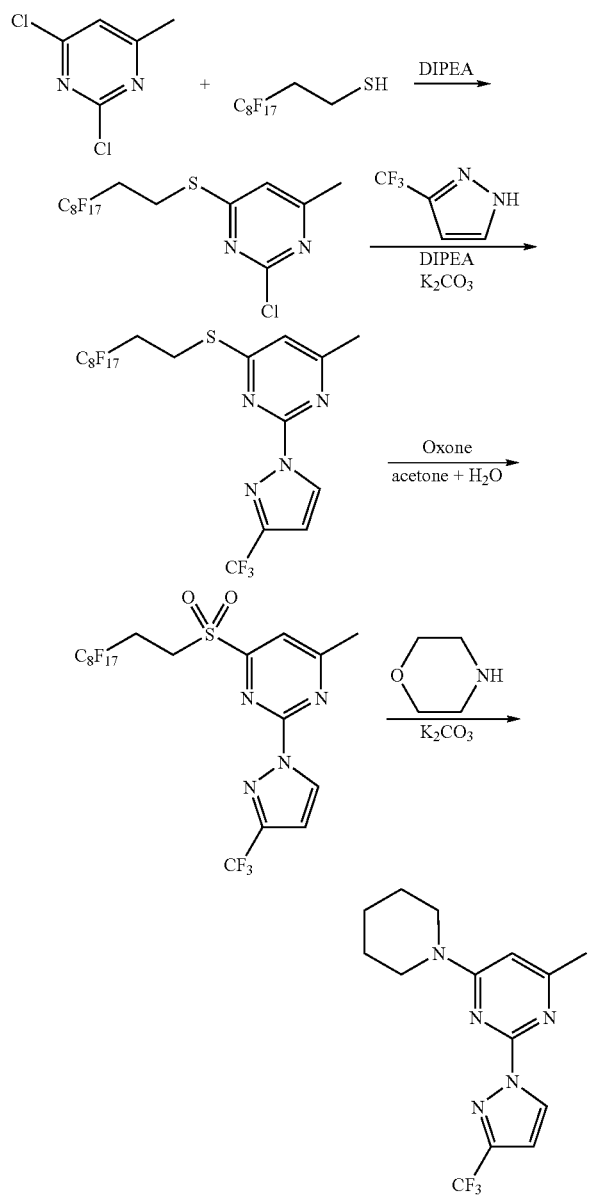

To a solution of 2,4-dichloro-6-methylpyrimidine (2.1 g) and fluorous thiol (available from Fluorous Technologies, Inc. and other commercial source, 6.1 g) in DMF (50 mL) was added diisopropylethylamine (DIPEA) (4.5 mL). After stirring at room temperature for 1 h, the reaction mixture was mixed with $H_2O$ and then extracted with EtOAc. The organic layer was washed with aqueous $NH_4Cl$, dried out $MaSO_4$, and concentrated. HPLC analysis of the crude product indicated 2-chloro-4-perfluoroalkylsulfanyl-6-methylpyrimidine and 4-chloro-2perfluoroalkylsulfanyl-6-methylpyrimidine (not show) in a ratio about 3:1. The major isomer was isolated as a desired product (4.3 g, 55% yield) using flash column chromatography on silica gel with hex:EtOAc (90:10). $^1$H NMR ($CDCl_3$) δ 2.45 (s, 3H), 2.63 (m, 2H), 3.42 (m, 2H), 6.98 (s, 1H). MS m/z (rel. intensity) 606 ($M^+$, 23), 368 (11), 236 (VI), 187 (100).

To a solution of 2-chloro-4-alkylthio-6-methylpyrimidine (0.50 g) and 3-trifluoromethylpyrazol (0.17 g) in DMF (40 mL) was added DIPEA (217 μL) and $K_2CO_3$ (113 mg). After heated at 80° C. for 12 h, the reaction mixture was extracted with EtOAc, washed with aqueous $NH_4Cl$, dried over $MgSO_4$, and concentrated. The crude product was purified by solid-phase extraction on a 5 g FluoroFlash® fluorous silica gel cartridge eluted with $MeOH/H_2O$ (80/20) and then MeOH. The MeOH fraction contained desired product was concentrated to give pyrozoyl-4-alkylthio-6-methylpyrimidine (0.49 g, 85%). $^1$H NMR ($CDCl_3$) δ 2.57 (s, 3H), 2.74 (m, 2H), 3.47 (m, 2H), 6.74 (d, 1H), 7.23 (s, 1H), 8.58 (br s, 1H). MS m/z (rel. intensity) 706 ($M^+$, 30), 687 (IX), 631 (X), 287 (100).

To a solution of pyrozoyl-4-alkylthio-6-methylpyrimidine (100 mg) in acetone (10 mL) was added a solution of Oxone® (350 mg) in $H_2O$ (3 mL) at room temperature. After heating at 60° C. for 12 h, the reaction mixture with white precipitate was filtrated. The filtrate was extracted with EtOAc, washed with brine. The organic layer was dried over $MgSO_4$ and concentrated to corresponding sulfone (94 mg, 91%). This compound was used for next step reaction without further purification. $^1$H NMR ($CDCl_3$) δ 2.83 (s, 3H), 2.93 (m, 2H), 3.75 (m, 2H), 6.81 (d, 1H), 7.81 (s, 1H), 8.66 (br s, 1H). MS m/z (rel. intensity) 739 ($M^++1$, 100).

To a solution of sulfone (15.0 mg) in DMF (1 mL) was added morpholine (5 mg). After heated at 80° C. for 10 h, the reaction mixture was extracted with EtOAc and then washed with aqueous $NH_4Cl$. Concentrated crude product was purified by SPE on a 2 g FluoroFlash® cartridge eluted with $MeOH/H_2O$ (80/20) and then MeOH. The $MeOH/H_2O$ fraction contained desired product was concentrated to give product (6 mg, 96%). $^1$H NMR ($CDCl_3$) δ 2.50 (s, 3H), 3.72 (br m, 4H), 3.83 (m, 4H), 6.33 (s, 1H), 6.69 (d, 1H), 8.61 (br s, 1H). MS m/z (rel. intensity) 314 ($M^++1$, 100).

Following the fluorous tag cleavage procedure described above, the sulfone was reacted with a series of nucleophilic reagents including primary and secondary amines, and thiols to afford 10 disubstituted pyrimidine analogs. The purities of the final products were greater than 90% by $^1$H NMR analysis.
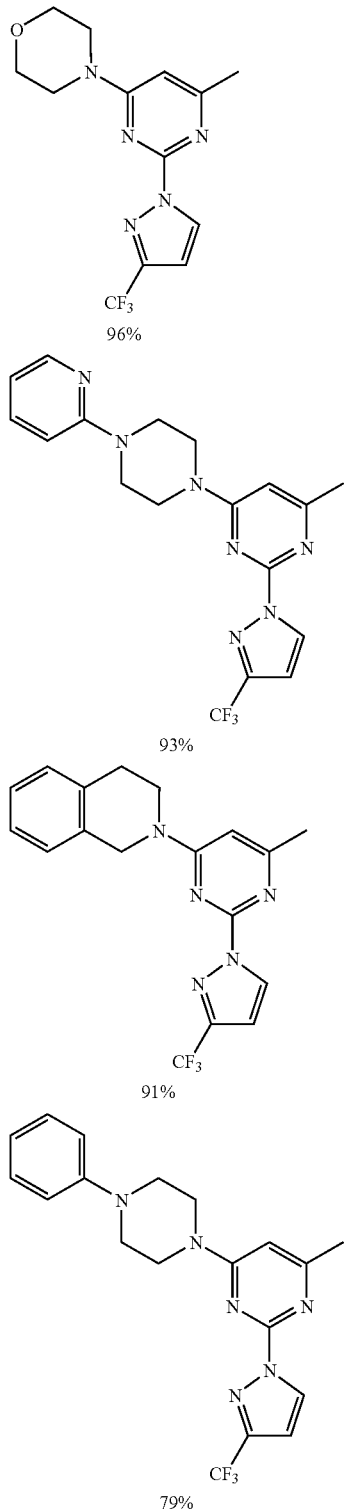
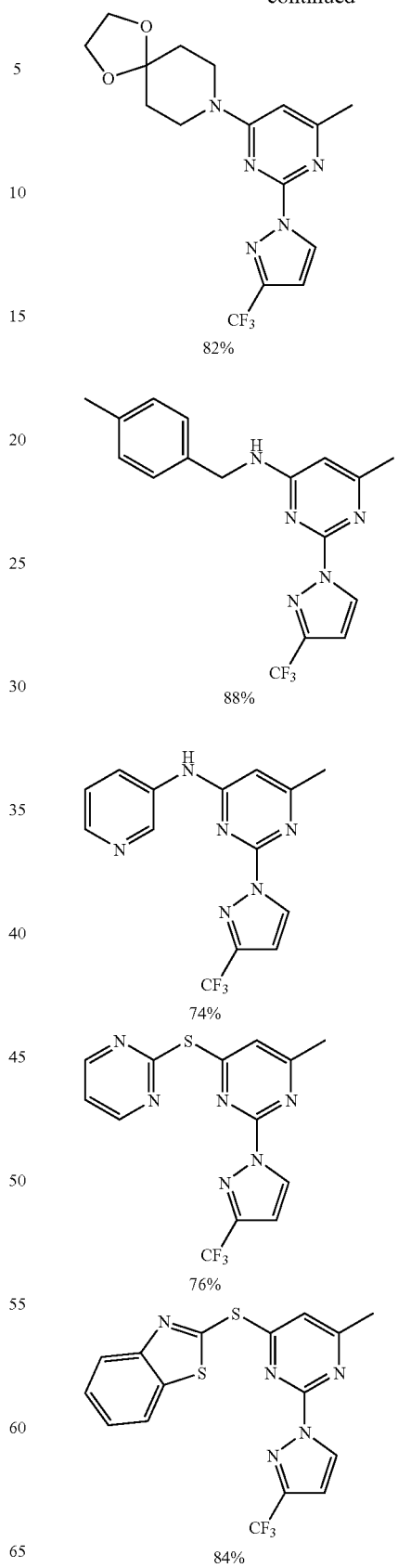

-continued

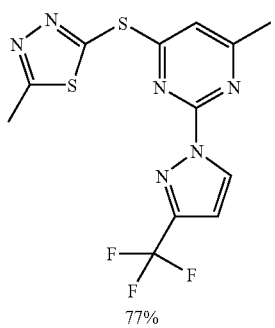

77%

Example VI

Preparation of Fluorous Isatoic Anhydride.

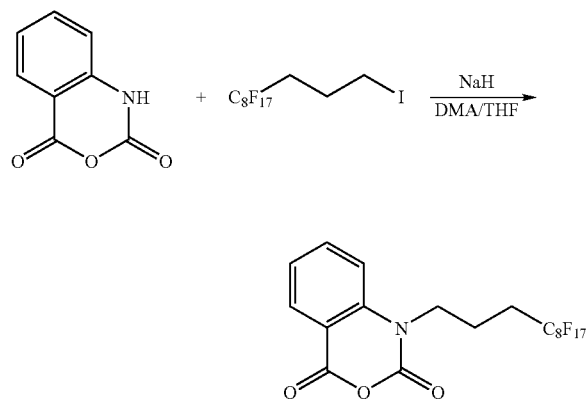

In a 2 L 3-neck flask equipped with N₂ gas inlet, mechanical stirbar, condenser, thermocouple and addition funnel, sodium hydride (7.8 g) was suspended in THF (140 ml) A solution of isatoic anhydride (29.1 g) in DMA (60 ml) and THF (100 ml) was added dropwise while maintaining the internal temperature below 40° C. After the addition was complete, DMA was added (60 ml), and the mixture was stirred at 50° C. for 45 minutes. A solution of 3-(perfluorooctyl)propyl iodide (100.0 g) in THF (100 ml) was added dropwise at 50° C. The mixture was stirred at 50° C. for 12 h. The reaction was quenched with NH₄Cl (~400 ml). An extraction was performed with ethyl acetate (2×200 ml). The organic layer was washed with H₂O (1×250 ml), dried over MgSO₄, filtered, and concentrated. The crude product was recrystallized in warm ethyl acetate (~250 ml), cooled slowly to room temperature, and then cooled further to 0° C. overnight. The product was collected by filtration and dried under high vacuum for 4 h to give product (57.0 g, 54% yield).

Use of Fluorous Isatoic Anhydride as an Electrophilic Scavenger in the Preparation of 1-butyl-3-phenyl-thiourea.

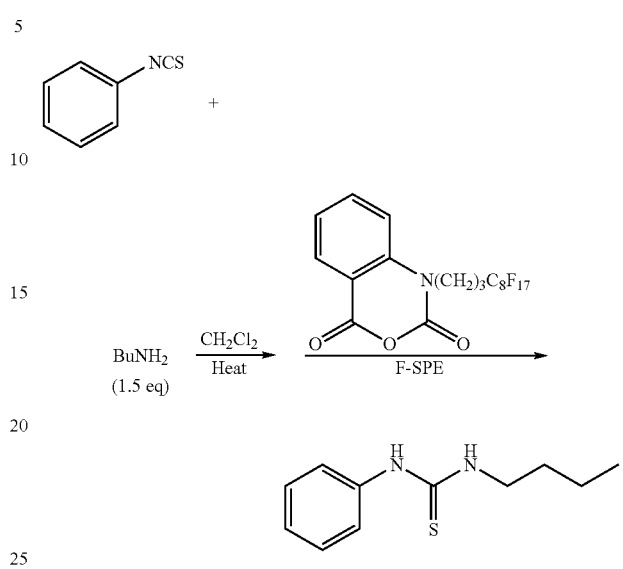

To a solution of phenyl isothiocyanate (22 μL) in CH₂Cl₂ (0.5 ml) was added excess amine (30 μL). The resulting solution was stirred at 60° C. on a sand bath overnight to ensure completion of the reaction. The reaction was monitored by TLC (30:70 EtOAc:hexanes). Upon completion of the reaction, Fluorous isatoic anhydride 6 was added (0.124 g) to the reaction mixture. Another 1.0 mL of CH₂Cl₂ was added to the reaction mixture to ensure complete dissolution of the solid. The reaction mixture was stirred for 2.5 h at 60° C. TLC showed the presence of the fluorous scavenger (that was added in excess), the scavenged product and the expected product. The mixture was concentrated under reduced pressure, and the residue was dissolved in a minimum amount of hot THF. This sample was loaded onto a 5 gm pre-moistened FluoroFlash® SPE cartridge with 80:20 MeOH:H₂O which is set on a vacuum manifold. The cartridge was eluted with 80:20 MeOH:H₂O, then 100% MeOH to wash off fluorous by-products from the cartridge. The first 2 fractions (2 times 8 ml) contained the desired product while the last 2 fractions that are eluted with 100% MeOH contained the fluorous by-products. The fractions were collected and the solvent evaporated under reduced pressure in a Speedvac overnight, giving the thiourea in 75% yield as a solid. $^1$H NMR, 300 MHz, CDCl₃: δ (ppm) 7.75 (br, 1H), 7.47–7.42 (m, 2H), 7.34–7.22 (m, 1H), 7.22–7.19 (m, 2H), 6.00 (br, 1H), 3.67–3.60 (m, 2H), 1.60–1.50 (m, 2H), 1.39–1.29 (m, 2H), 0.92 (t, J=7.28 Hz, 3H). HRMS: calc'd for $C_{11}H_{16}S$ (M+), 208.1034; found 208.1034 (M+).

Following the general procedure described above, three substrates (isothiocyanate, isocyanate, and epoxide) were reacted with five amines to generate a 15-compound library in parallel. The structures of the products are shown in Table 5. All product purities were greater than 90% by $^1$H NMR.

TABLE 5

Structures, Yields of Amination Products

| | PhNCS | PhNCO |
|---|---|---|
| n-BuNH₂ | PhNH-C(S)-NH-Bu, 75% | PhNH-C(O)-NH-Bu, 100% |
| 4-MeC₆H₄CH₂NH₂ | PhNH-C(S)-NH-CH₂-C₆H₄-4-Me, 72% | PhNH-C(O)-NH-CH₂-C₆H₄-4-Me, 100% |
| tryptamine | PhNH-C(S)-NH-CH₂CH₂-(indol-3-yl), 95% | PhNH-C(O)-NH-CH₂CH₂-(indol-3-yl), 100% |
| 1-(2-pyridyl)piperazine | PhNH-C(S)-N(piperazinyl-pyridyl), 100% | PhNH-C(O)-N(piperazinyl-pyridyl), 100% |
| 1,2,3,4-tetrahydroisoquinoline | PhNH-C(S)-N(tetrahydroisoquinolinyl), 100% | PhNH-C(O)-N(tetrahydroisoquinolinyl), 100% |

| | 4-MeO-C₆H₄-O-CH₂-(oxiranyl) |
|---|---|
| n-BuNH₂ | 4-MeO-C₆H₄-O-CH₂-CH(OH)-CH₂-NH-Bu, 42% |

TABLE 5-continued

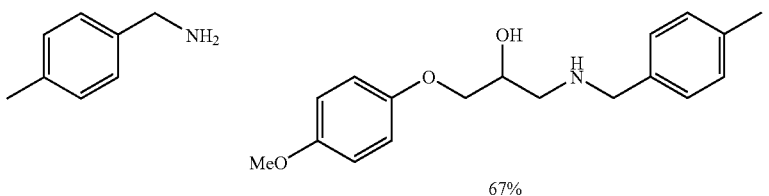

67%

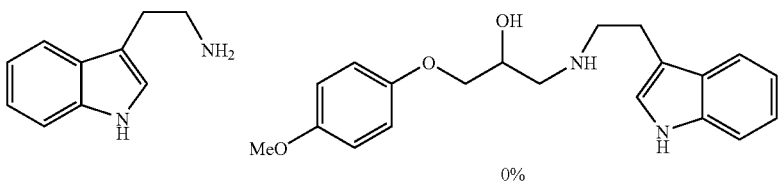

0%

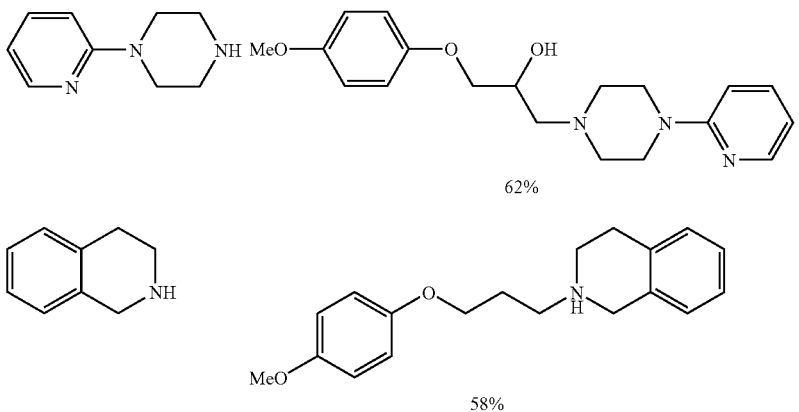

62%

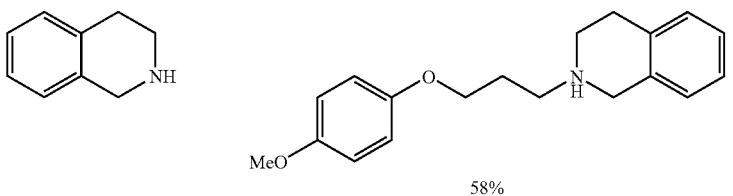

58%

Example VII

Synthesis of Fluorous Trityl

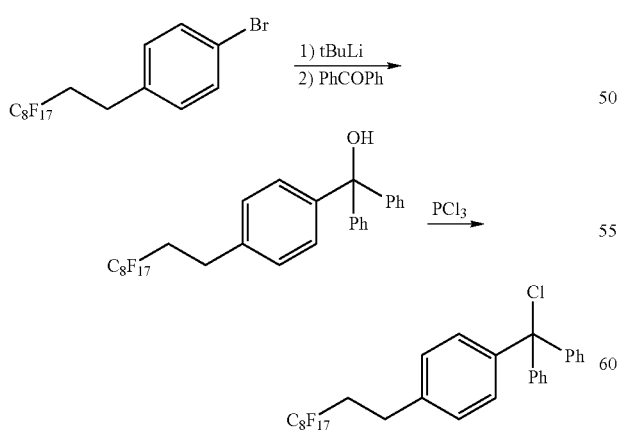

A solution of ⁱBuLi (1.7 M in pentane, 20.0 mL) in ether (75 mL) was cooled to −78° C. under inert atmosphere. 4-(1H,1H,2H,2H-perfluorodecyl)phenylbromide (10.0 g, 0.017 mol) in ether (25 mL) was added at a rate to maintain the internal temperature to below −45° C., then allowed to warm to ~−30° C. for 30 minutes, then cooled back down to −78° C. To the lithiate was added a solution of the benzophenone (3.10 g) in ether (25 mL) at a rate to maintain the internal temperature below −45° C. After complete addition, the reaction was allowed to come to room temperature overnight. The reaction was quenched with water (50 mL), then acidified to pH=3 with 2 N HCl (~25 mL) and separated. The aqueous layer was extracted with ether (2×100 mL), organics combined, washed with brine (100 mL) and dried over MgSO₄. The solvent was removed, the crude product was separated via flash chromatography (10% EtOAc in hexanes), and recrystallized from methanol/water to provide a white crystalline solid (3.0 g, 52%).

The trityl alcohol (1.0 g, 1.43 mmol) was dissolved in CHCl₃ (50 mL) and PCl₃ (4.5 g) was added. The reaction was checked by TLC (10% EtOAc in hexanes), and additional PCl₃ was added to complete the reaction as necessary, with the total reaction time being 8 hr at room temperature. The reaction was then quenched with water (5 mL), separated, organic layer dried with MgSO₄ and solvent removed to provide the pure product as an off white crystalline solid (0.84 g, 82% yield).

Example VIII

Preparation of Fluorous TBD

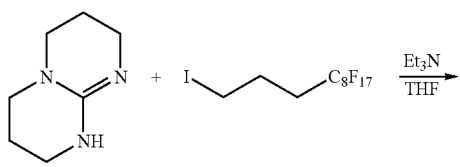

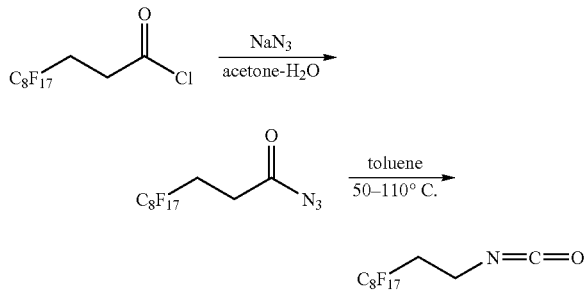

To a solution of 1,3,6,7,8-hexahydro-2H-pyrimido[1,2-a]pyrimidine (5.6 g) in 80 mL of THF was added 3-(perfluorooctyl)propyl iodide (11.8 g) and triethylamine (2.6 mL). The mixture was stirred at 25° C. for 12 h. The precipitate was collected by filtration. The solid was mixed with 50 mL of 30% NaOH, extracted with EtOAc. The organic layer was concentrated to give desired product as a semisolid (3.8 g, 32%).

Example IX

Preparation of Fluorous Isocyanate

Preparation of 3-(perfluorooctyl)propionyl Azide:

Sodium azide (6.0 g) was put in a 250 mL round-bottom flask (2-neck) equipped with a thermometer. $H_2O$ (20 mL) was added to dissolve sodium azide. It was cooled on an ice-water bath. A solution of 3-(perfluorooctyl)propionyl chloride (12.9 g) in acetone (25 mL) was added dropwise to keep the temperature below 12° C. The mixture was vigorously stirred for 2 h. Dimethyl ether (100 mL) and water (100 mL) are added, and the mixture was vigorously stirred for 1 min. After the separation of two layers, the aqueous layer was extracted with ether (2×50 mL). The ether layers were combined, and are washed with water (3×100 mL) and brine. After drying over $MgSO_4$, the solvent was removed under vacuum to give a mixture of white solid and liquid (12.0 g) that was immediately used for the next reaction.

Preparation of 3-(perfluorooctyl)ethyl Isocyanate.

A solution of crude 3-(perfluorooctyl)propionyl azide (12 g) in toluene was put in a 500 mL round-bottom flask equipped with a condenser and a thermometer. The mixture was gradually warmed to 50–55° C. over 1 h, and the temperature was maintained at around 55° C. for 2 h. The mixture was then refluxed for 1 h. After cooling, the solvent was removed by a rotavap, the residue was distilled under high-vac to give non-color liquid that solidifies at room temperature.

Use of Fluorous Isocyanate as an Electrophilic Scavenger in the Preparation of 1-(4-methylbenzyl)-3-phenyl-thiourea.

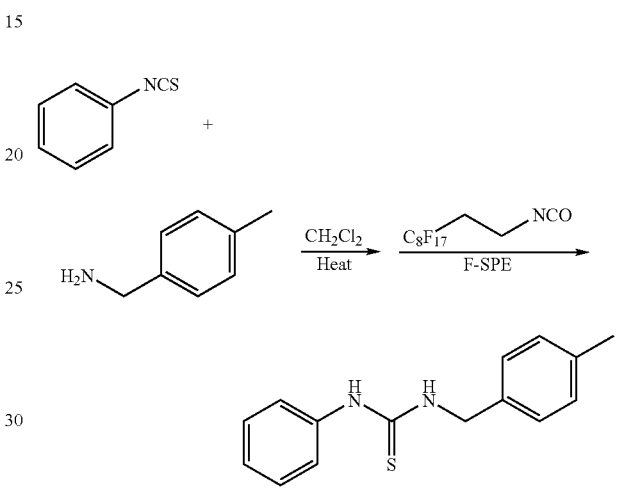

To a solution of phenyl isothiocyanate (24 μL) in $CH_2Cl_2$ (0.5 ml) was added excess amine (30 μL). The resulting solution was stirred at 55–60° C. on a sand bath overnight (8–12 h) to ensure completion of the reaction. The reaction was monitored by TLC (30:70 EtOAc:Hexanes). Upon completion of the reaction, fluorous isocyanate was added (0.10 g) to the reaction mixture. Another 1.0–2.0 ml of $CH_2Cl_2$ was added to the reaction mixture to ensure complete dissolution of the solid. The reaction mixture was stirred at 60° C. for 2.5 h. TLC showed the presence of the fluorous scavenger (that was added in excess), the scavenged product and the expected product. The mixture was concentrated under reduced pressure, and the residue was dissolved in a minimum amount of hot THF. This sample was loaded onto a 5 gm pre-moistened FluoroFlash® SPE cartridge with 80:20 MeOH:$H_2O$ which is set on a vacuum manifold. The cartridge was eluted with 80:20 MeOH:$H_2O$, then 100% MeOH to wash off fluorous by-products from the cartridge. The first 2 fractions (2 times 8 ml) contained the desired product while the last 2 fractions (2 times 8 ml) that are eluted with 100% MeOH contained the fluorous by-products. The fractions were collected and the solvent evaporated under reduced pressure in a Speedvac overnight, giving the thiourea in 80% yield as a solid. $^1$H NMR, 300 MHz, $CDCl_3$: δ 7.68 (br, 1H), 7.41 (t, J=7.94 Hz, 2H), 7.27 (t, J=7.45 Hz, 2H), 7.21–7.18 (m, 3H), 7.14 (d, J=7.77 Hz, 2H), 6.20 (br, 1H), 4.84 (d, J=5.34 Hz, 2H), 2.33 (s, 3H). HRMS: calc'd for $C_{15}H_{16}N_2S$ (M+), 256.1034; found 256.1029 (M+).

Following the general procedure described above, two substrates (isothiocyanate and isocyanate) were reacted with five amines to generate a 10-compound library in parallel. The structures of the products are shown in Table 6. All product purities were greater than 90% by $^1$H NMR.

TABLE 6

Structures, Yields of Amination Products

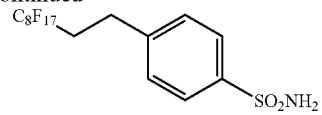

Example X

Preparation of 4-(1H,1H,2H,2H-Perfluorodecyl)benzene-sulfonamide

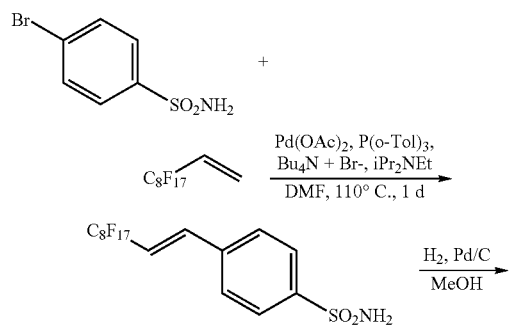

1H,1H,2H-perfluorodec-1-ene (8.5 g), 4-bromobenzenesulfoamide (3.0 g), Pd(OAc)$_2$ (0.13 g), tri-o-tolylphosphine (0.35 g), Bu$_4$NBr (2.4 g), $^i$Pr$_2$NEt (8.5 mL) were dissolved in DMF (60 mL), and the mixture was stirred at 110° C. for 1 d under an nitrogen atmosphere. It was then cooled to room temperature, and DMF was removed under reduced pressure. The crude material was passed through a silica gel column (eluent: hexanes/EtOAc=4:1). The filtrate was concentrated, and it was dissolved in Et$_2$O, and then it was treated with charcoal. The charcoal was removed by filtration through a pad of Celite®. The product was purified by fluorous solid-phase extraction with a 20 g FluoroFlash® cartridge (eluent: MeOH/H$_2$O=70:30 to 100% MeOH). The MeOH fraction was concentrated to give the product (1.8 g, 24% yield).

To a solution of 4-(1H,2H-perfluorodec-1-enyl)benzenesulfonamide (0.11 g) in MeOH (20 mL) was added Pd/C (5 wt % on activated carbon, 33 mg) under an nitrogen atmosphere. The mixture was then stirred under hydrogen atmosphere (1 atm) for 20 h at 23° C. The catalyst was removed by filtration through a Celite® pad, and the Celite® was rinsed with Et$_2$O (100 mL). The filtrate was concentrated to give the product as pale yellow solid (0.10 g, 90% yield). $^1$H NMR (270 MHz, CD$_3$OD) δ 7.85 (2H, d, J=8.3 Hz), 7.46 (2H, d, J=8.3 Hz), 4.90 (2H, br s), 3.05–2.98 (2H, m), 2.65–2.35 (2H, m); MS APCI negative m/z=632 [M−H].

Example XI

Preparation of Fluorous Triamine

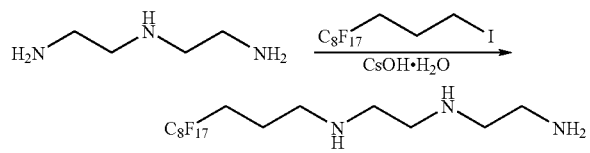

In a 50 ml 2-neck flask, 4 angstrom molecular sieves (activated powder) (0.10 g) was dried under N$_2$ flow with a heat gun for 5 min. Cesium hydroxide monohydrate (0.143 g) was added. DMF (15 ml) was added, and the mixture stirred vigorously for 10 min. Diethylenetriamine (0.91 ml) was added, and the mixture stirred vigorously for 10 min. Fluorous propyl iodide (0.50 g) was added portionwise. The mixture was stirred for under N$_2$ for 18 h at 25° C. The reaction mixture was extracted with ether (3×50 ml). The ether layers were washed with water (2×75 ml) and brine (1×75 ml). The organic layer was dried over MgSO$_4$, filtered, and concentrated. The crude product was taken up in ether. 1 M HCl in ether (1.5 ml) was added. Extracted with H$_2$O (3×50 ml). The aqueous layer was washed with 2 N NaOH (50 ml). The product was extracted with ether (3×30 ml). The ether layer was concentrated and dried under high vacuum to give product (0.21 g, 44% yield).

Although the forgoing description has necessarily presented a limited number of embodiments of the invention, those of ordinary skill in the relevant art will appreciate that various changes in the components, details, materials, and process parameters of the examples that have been herein described and illustrated in order to explain the nature of the invention may be made by those skilled in the art, and all such modifications will remain within the principle and scope of the invention as expressed herein in the appended claims. It will also be appreciated by those skilled in the art that changes could be made to the embodiments described above without departing from the broad inventive concept thereof. It is understood, therefore, that this invention is not limited to the particular embodiments disclosed, but it is intended to cover modifications that are within the principle and scope of the invention, as defined by the appended claims.

What is claimed is:

1. A compound for increasing the fluorous nature of an organic compound, said compound having the formula:

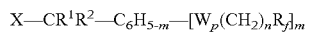

wherein R$_f$ is a fluorous group, X is selected from the group consisting of a leaving group, a nucleophilic group and an electrophilic group, R$^1$ and R$^2$ are independently, the same or different, one of a hydrogen, a linear alkyl, a branched alkyl, a phenyl, an aryl, C$_6$H$_{5-q}$(W')$_q$, C$_6$H$_{5-m'}$[W$_{p'}$(CH$_2$)$_n$R$_f$]$_{m'}$, and C$_6$H$_{5-m''}$[W$_{p''}$(CH$_2$)$_{n''}$R$_f$]$_{m''}$, m, m' and m'' are each integers from 1 to 5, n, n' and n'' are each integers from 0 to 5, p, p' and p'' each have a value of 0 or 1, q is an integer from 0 to 5, W is a grouping of atoms selected from the group consisting of O, S, NR$^3$, CR$^4$R$^5$, and SiR$^6$R$^7$, wherein when W is SiR$^6$R$^7$ and R$^1$ and R$^2$ are each hydrogen, X is not one of Br, N-imidazolyl —OC(O)—CI and —OH, and W' is a grouping of atoms selected from the group consisting of OR$^8$, SR$^9$, NR$^{10}$R$^{11}$, CR$^{12}$R$^{13}$R$^{14}$, and SiR$^{15}$R$^{16}$R$^{17}$, wherein R$^3$, R$^4$, R$^5$, R$^6$, R$^8$, R$^9$, R$^{10}$, R$^{11}$, R$^{12}$, R$^{13}$, and R$^{14}$ are independently, the same or different, one of hydrogen, linear alkyl, branched alkyl, aryl, benzyl and —(CH$_2$)$_{n'''}$R$_f$, and R$^6$, R$^7$, R$^{15}$, R$^{16}$, and R$^{17}$ are independently, the same or different, one of linear alkyl, branched alkyl, aryl, benzyl and —(CH$_2$)$_{n'''}$R$_f$, wherein n''' is an integer from 0 to 5, wherein when X is —OH, R$^1$ is one of hydrogen, a phenyl, C$_6$H$_{5-q}$(W')$_q$, C$_6$H$_{5-m'}$[W$_{p'}$(CH$_2$)$_n$R$_f$]$_{m'}$ and C$_6$H$_{5-m''}$[W$_{p''}$(CH$_2$)$_{n''}$R$_f$]$_{m''}$ and R$^2$ is one of a phenyl, C$_6$H$_{5-q}$(W')$_q$, C$_6$H$_{5-m'}$[W$_{p'}$(CH$_2$)$_n$R$_f$]$_{m'}$ and C$_6$H$_{5-m''}$[W$_{p''}$(CH$_2$)$_{n''}$R$_f$]$_{m''}$ and wherein when X is an electrophilic group, X is —NCZ, wherein Z is one of oxygen and sulfur.

2. The compound of claim 1 wherein X is a leaving group selected from the group consisting of a halide, a methane sulfonate, a p-toluenesulfonate, a trifluoromethanesulfonate and R$^{18}$SO$_3$—, wherein R$^{18}$ is one of linear alkyl, branched alkyl, aryl, benzyl, and (CH$_2$)$_{n''''}$R$_f$, wherein n'''' is an integer from 0 to 5.

3. The compound of claim 1 wherein X is a nucleophilic group selected from the group consisting of —OH, —OR$^{19}$, —NH$_2$, —NHR$^{19}$, —NR$^{19}$R$^{20}$, —NHC(=NH)NH$_2$, —SH, —SR$^{19}$, —NH(CH$_2$)$_{n''''}$NH$_2$, and —NH(CH$_2$)$_{n''''}$N((CH$_2$)$_{n''''}$NH$_2$)$_2$, wherein n'''' is an integer from 1 to 5, and R$^{19}$ and R$^{20}$ are independently, the same or different, one of a linear alkyl, a branched alkyl, an aryl and a benzyl group.

4. The compound of claim 1 wherein R$_f$ is a fluorous group selected from the group consisting of a perfluorocarbon, a fluorohydrocarbon, a fluorinated ether and a fluorinated amine.

5. The compound of claim 1 wherein X is a leaving group and R$^1$ and R$^2$ are each hydrogen.

6. The compound of claim 1 wherein X is a leaving group and R$^1$ and R$^2$ are independently, the same or different, one of C$_6$H$_{5-m'}$[W$_{p'}$(CH$_2$)$_n$R$_f$]$_{m'}$ and C$_6$H$_{5-m''}$[W$_{p''}$(CH$_2$)$_{n''}$R$_f$]$_{m''}$.

7. The compound of claim 1 wherein X is —SH.

8. The compound of claim 1 wherein X is one of NR$^{21}$R$^{22}$ and NR$^{21}$R$^{22}$R$^{23+}$Y$^−$, wherein R$^{21}$, R$^{22}$ and R$^{23}$ are independently, the same or different, one of a hydrogen, a linear alkyl, a branched alkyl and a benzyl group and Y is a counter anion selected from the group consisting of Cl$^−$, Br$^−$, I$^−$ and CO$_3^{2−}$.

9. The compound of claim 1 wherein X is —NH$_2$, R$^1$ is hydrogen and R$^2$ is C$_6$H$_{5-q}$(W')$_q$.

10. The compound of claim 1 wherein X is —NH(CH$_2$)$_{n''''}$NH$_2$, wherein n'''' is an integer from 1 to 5.

11. The compound of claim 1 wherein X is —NH(CH$_2$)$_{n''''}$N((CH$_2$)$_{n''''}$NH$_2$)$_2$, wherein n'''' is an integer from 1 to 5.

12. The compound of claim 1 wherein X is —NHC(=N)NH$_2$.

13. The compound of claim 1 wherein X is —SH and R$^1$ and R$^2$ are each hydrogen.

14. The compound of claim 1 wherein X is $SR^{24}$, wherein $R^{24}$ is one of a linear alkyl, a branched alkyl, an aryl, and a benzyl group.

15. The compound of claim 1 wherein X is —NCZ, wherein Z is one of O and S and $R^1$ and $R^2$ are each hydrogen.

16. A compound for increasing the fluorous nature of an organic compound, said compound having the formula:

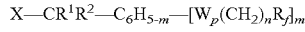

wherein $R_f$ is a fluorous group, X is one of a nucleophilic group and a leaving group, $_1$ is one of a hydrogen, a linear alkyl, a branched alkyl, a phenyl, an aryl, $C_6H_{5-q}(W')_q$, and $C_6H_{5-m'}[W_{p'}(CH_2)_{n'}R_f]_{m'}$, $R^2$ is one of a linear alkyl, a branched alkyl, a phenyl, an aryl, $C_6H_{5-q}(W')_q$, $C_6H_{5-m'}[W_{p'}(CH_2)_{n'}R_f]_{m'}$, and $C_6H_{5-m''}[W_{p''}(CH_2)_{n''}R_f]_{m''}$, m, m' and m'' are each integers from 1 to 5, n, n' and n'' are each integers from 0 to 5, p, p' and p'' each have a value of 0 or 1, q is an integer from 0 to 5, W is a grouping of atoms selected from the group consisting of O, S, $NR^3$, $CR^4R^5$, and $SiR^6R^7$, and W' is a grouping of atoms selected from the group consisting of $OR^8$, $SR^9$, $NR^{10}R^{11}$, $CR^{12}R^{13}R^{14}$, and $SiR^{15}R^{16}R^{17}$, wherein $R^3$, $R^4$, $R^5$, $R^6$, $R^8$, $R^9$, $R^{10}$, $R^{11}$, $R^{12}$, $R^{13}$, and $R^{14}$ are independently, the same or different, one of hydrogen, linear alkyl, branched alkyl, aryl, benzyl and —$(CH_2)_{n'''}R_f$ and $R^6$, $R^7$, $R^{15}$, $R^{16}$, and $R^{17}$ are independently, the same or different, one of linear alkyl, branched alkyl, aryl, benzyl and —$(CH_2)_{n'''}R_f$, wherein n''' is an integer from 0 to 5.

17. The compound of claim 16, wherein X is a leaving group selected from the group consisting of a halide, methane sulfonate, p-toluenesulfonate, trifluoromethanesulfonate and $R^{18}SO_3$—, wherein $R^{18}$ is one of linear alkyl, branched alkyl, aryl, benzyl, and —$(CH_2)_{n''''}R_f$, wherein n'''' is an integer from 0 to 5.

18. The compound of claim 16, wherein X is a nucleophilic group selected from the group consisting of —OH, —$NH_2$, —$NHR^{19}$, —$NR^{19}R^{20}$, wherein $R^{19}$ and $R^{20}$ are independently, the same or different, one of a linear alkyl, a branched alkyl, an aryl and a benzyl group.

19. The compound of claim 16, wherein X is one of —OH, —Cl, —Br, and —I.

20. A compound for increasing the fluorous nature of an organic compound, said compound having the formula:

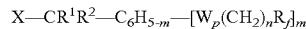

wherein $R_f$ is a fluorous group, X is one of a nucleophilic group and a leaving group, $R^1$ is one of a phenyl, an aryl, $C_6H_{5-q}(W')_q$, and $C_6H_{5-m}[W_p(CH_2)_nR_f]_m$, $R^2$ is one of a phenyl, an aryl, $C_6H_{5-q}(W')_q$, $C_6H_{5-m'}[W_{p'}(CH_2)_{n'}R_f]_{m'}$, and $C_6H_{5-m''}[W_{p''}(CH_2)_{n''}R_f]_{m''}$, m, m' and m'' are each integers from 1 to 5, n, n' and n'' are each integers from 0 to 5, p, p' and p'' each have a value of 0 or 1, q is an integer from 0 to 5, W is a grouping of atoms selected from the group consisting of O, S, $NR^3$, $CR^4R^5$, and $SiR^6R^7$, and W' is a grouping of atoms selected from the group consisting of $OR^8$, $SR^9$, $NR^{10}R^{11}$, $CR^{12}R^{13}R^{14}$, and $SiR^{15}R^{16}R^{17}$, wherein $R^3$, $R^4$, $R^5$, $R^6$, $R^8$, $R^9$, $R^{10}$, $R^{11}$, $R^{12}$, $R^{13}$, and $R^{14}$ are independently, the same or different, one of hydrogen, linear alkyl, branched alkyl, aryl, benzyl and —$(CH_2)_{n'''}R_f$ and $R^6$, $R^7$, $R^{15}$, $R^{16}$, and $R^{17}$ are independently, the same or different, one of linear alkyl, branched alkyl, aryl, benzyl and —$(CH_2)_{n'''}R_f$, wherein n''' is an integer from 0 to 5.

21. The compound of claim 20 wherein X is a leaving group selected from the group consisting of a halide, methane sulfonate, p-toluenesulfonate, trifluoromethanesulfonate and $R^{18}SO_3$—, wherein $R^{18}$ is one of linear alkyl, branched alkyl, aryl, benzyl, and —$(CH_2)_{n''''}R_f$, wherein n'''' is an integer from 0 to 5.

22. The compound of claim 20, wherein X is a nucleophilic group selected from the group consisting of —OH, —$NH_2$, —$NHR^{19}$, —$NR^{19}R^{20}$, wherein $R^{19}$ and $R^{20}$ are independently, the same or different, one of a linear alkyl, a branched alkyl, an aryl and a benzyl group.

23. The compound of claim 20, wherein X is one of —OH, —Cl, —Br, and —I.

* * * * *